(12) United States Patent
Sibinga et al.

(10) Patent No.: US 8,586,534 B2
(45) Date of Patent: Nov. 19, 2013

(54) INTRACELLULAR DOMAIN OF A MAMMALIAN FAT1 (FAT1IC)

(75) Inventors: Nicholas E. S. Sibinga, Chappaqua, NY (US); Rong Hou, Fenton, MO (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 0 days.

(21) Appl. No.: 12/150,176

(22) Filed: Apr. 25, 2008

(65) Prior Publication Data

US 2009/0117169 A1    May 7, 2009

Related U.S. Application Data

(60) Provisional application No. 60/928,216, filed on May 8, 2007.

(51) Int. Cl.
*A61K 38/16* (2006.01)
*C07K 14/00* (2006.01)

(52) U.S. Cl.
USPC .................................. 514/12; 530/350

(58) Field of Classification Search
None
See application file for complete search history.

(56) References Cited

U.S. PATENT DOCUMENTS

| | | | | |
|---|---|---|---|---|
| 6,429,232 B1 * | 8/2002 | Kinsella et al. | ............... | 514/449 |
| 2003/0129176 A1 * | 7/2003 | Jones et al. | .................. | 424/94.1 |

OTHER PUBLICATIONS

Dunne et al., Molecular Cloning and Tissue Expression of FAT, the Human Homologue of the *Drosophila* fat Gene That Is Located on Chromosome 4q34-q35 and Encodes a Putative Adhesion Molecule. Genomics 30: 207-223, 1995.*

Magg et al., Processing of the human protocadherin Fat1 and translocation of its cytoplasmic domain to the nucleus. Experimental Cell research 307: 100-108, 2005.*

Russell Ross, Atherosclerosis—an inflammatory disease. N. Engl. J. Med 340:115-126, 1999.*

LaFlamme et al., Single subunit chimeric integrins as mimics and inhibitors of endogenous integrin functions in receptor localization, cell spreading and migration, and matrix assembly. J. Cell Biol. 126:1287-1298, 1994.*

D.I. Axel, Paclitaxel inhibits arterial smooth muscle cell proliferation and migration in vitro and in vivo using local drug delivery, Circulation, Jul. 15, 1997; 96(2) :636-45 (Abstract).

Rong Hou, et al., The Fat1 cadherin integrates vascular smooth muscle cell growth and migration signals, The Journal of Cell Biology, vol. 173, No. 2, May 8, 2006, pp. 417-429.

Christian M. Matter, et al., Effects of Tacrolimus or Sirolimus on Proliferation of Vascular Smooth Muscle and Endothelial Cells, Cardiovasc Pharmacol, vol. 48, No. 6, Dec. 2006.

* cited by examiner

*Primary Examiner* — Ruixiang Li
(74) *Attorney, Agent, or Firm* — Amster, Rothstein & Ebenstein LLP

(57) ABSTRACT

Provided is an extracellular domain of a mammalian Fat1 ($Fat1_{EC}$). Also provided is an intracellular domain of a mammalian Fat1 ($Fat1_{IC}$). Additionally provided is a vector comprising a nucleic acid sequence encoding the $Fat1_{EC}$. A vector comprising a nucleic acid sequence encoding the $Fat1_{IC}$ is further provided. Also, a vascular stent coated with the $Fat1_{EC}$ is provided. Further provided is a vascular stent coated with a Fat1 ligand that activates Fat1. A method of treating a patient at risk for restenosis of a blood vessel is additionally provided. Further, methods of treating an injured blood vessel in a patient is provided. A method of treating a patient at risk for restenosis of a blood vessel or having an injured blood vessel is also provided.

5 Claims, 10 Drawing Sheets

SEQUENCE LISTING

```
<160> NUMBER OF SEQ ID NOS: 14

<210> SEQ ID NO 1
<211> LENGTH: 4598
<212> TYPE: PRT
<213> ORGANISM: mouse

<400> SEQUENCE: 1

Met Gly Arg His Leu Thr Leu Leu Leu Leu Leu Leu Phe Leu Gln
1               5                   10                  15

Gln Phe Gly Asp Ser Asp Gly Ser Gln Arg Leu Glu Pro Thr Pro Pro
                20                  25                  30

Ile Gln Phe Thr His Phe Gln Tyr Asn Val Thr Val His Glu Asn Ser
                35                  40                  45

Ala Ala Lys Thr Tyr Val Gly His Pro Arg Lys Met Gly Ile Tyr Ile
    50                  55                  60

Leu Asp Pro Ser Trp Glu Ile Arg Tyr Lys Ile Val Ser Gly Asp Ser
65                  70                  75                  80

Glu Asn Leu Phe Lys Ala Glu Glu Tyr Val Leu Gly Asp Phe Cys Phe
                85                  90                  95

Leu Arg Ile Arg Thr Lys Gly Gly Asn Thr Ala Ile Leu Asn Arg Glu
                100                 105                 110

Val Arg Asp His Tyr Thr Leu Ile Val Lys Ala Val Glu Lys Ala Thr
            115                 120                 125

Asp Ala Glu Ala Arg Ala Lys Val Arg Val Gln Val Leu Asp Thr Asn
    130                 135                 140

Asp Leu Arg Pro Leu Phe Ser Pro Thr Ser Tyr Ser Val Ser Leu Pro
145                 150                 155                 160

Glu Asn Thr Ala Ile Arg Thr Ser Ile Ala Arg Val Ser Ala Thr Asp
                165                 170                 175

Ala Asp Ile Gly Thr Asn Gly Glu Phe Tyr Tyr Ser Phe Lys Asp Arg
                180                 185                 190

Thr Asp Val Phe Ala Ile His Pro Thr Ser Gly Val Val Leu Thr
            195                 200                 205

Gly Arg Leu Asp Phe Leu Glu Thr Gln Leu Tyr Glu Leu Glu Ile Leu
        210                 215                 220

Ala Ala Asp Arg Gly Met Lys Leu Tyr Gly Ser Ser Gly Val Ser Ser
225                 230                 235                 240

Leu Ala Lys Leu Thr Val His Val Glu Gln Ala Asn Glu Cys Ala Pro
                245                 250                 255

Ile Ile Thr Ala Val Thr Leu Ser Pro Ser Glu Leu Asp Lys Asp Pro
                260                 265                 270
```

-continued

```
Thr Tyr Ala Ile Ile Thr Val Glu Asp Cys Asp Gln Gly Ala Asn Gly
            275                 280                 285

Glu Ile Ala Ser Leu Ser Ile Val Ala Gly Asp Leu Leu Gln Gln Phe
        290                 295                 300

Lys Thr Val Arg Ser Phe Pro Gly Ser Lys Ala Phe Lys Val Lys Ala
305                 310                 315                 320

Val Gly Ala Val Asp Trp Asp Ser His Pro Tyr Gly Tyr Asn Leu Thr
                325                 330                 335

Leu Gln Ala Lys Asp Lys Gly Thr Pro Pro Gln Phe Ser Pro Val Lys
            340                 345                 350

Val Val His Ile Ile Ser Pro Gln Phe Arg Ala Gly Pro Val Lys Phe
        355                 360                 365

Glu Met Asp Val Tyr Arg Ala Glu Ile Ser Glu Phe Ala Pro Pro His
    370                 375                 380

Thr Pro Val Val Leu Val Lys Ala Ile Pro Ser Tyr Ser His Leu Arg
385                 390                 395                 400

Tyr Val Phe Lys Ser Ala Pro Gly Lys Pro Lys Phe Gly Leu Asn His
                405                 410                 415

Asn Thr Gly Leu Ile Ser Ile Leu Glu Pro Ile Arg Arg Gln His Thr
            420                 425                 430

Ser His Phe Glu Leu Glu Val Thr Thr Ser Asp Lys Arg Ala Ser Ala
        435                 440                 445

Arg Val Val Lys Val Leu Gly Thr Asn Ser Asn Pro Pro Glu Phe
    450                 455                 460

Thr Gln Thr Ser Tyr Lys Ala Ser Ile Asp Glu Asn Ala Pro Ile Gly
465                 470                 475                 480

Ala Ala Val Thr Arg Val Ser Ala Met Asp Pro Asp Glu Gly Glu Asn
                485                 490                 495

Gly Tyr Val Thr Tyr Ser Ile Ala Asn Leu Asn His Val Pro Phe Val
            500                 505                 510

Ile Asp His Phe Thr Gly Thr Val Ser Thr Ser Glu Asn Leu Asp Tyr
        515                 520                 525

Glu Leu Met Pro Arg Val Tyr Thr Leu Arg Ile Arg Ala Ser Asp Trp
    530                 535                 540

Gly Leu Pro Tyr Arg Arg Glu Val Glu Val Leu Ala Thr Ile Thr Leu
545                 550                 555                 560

Asn Asn Leu Asn Asp Asn Thr Pro Leu Phe Glu Arg Ile Asn Cys Glu
                565                 570                 575

Gly Thr Ile Pro Arg Asp Leu Gly Val Gly Glu Gln Ile Thr Thr Val
            580                 585                 590

Ser Ala Ile Asp Ala Asp Glu Leu Gln Leu Val Arg Tyr Gln Ile Glu
        595                 600                 605

Ala Gly Asn Glu Leu Asp Leu Phe Gly Leu Asn Pro Ser Ser Gly Val
    610                 615                 620

Leu Ser Leu Lys His Ser Leu Thr Asp Gly Leu Gly Ala Lys Val Ser
625                 630                 635                 640

Phe His Ser Leu Arg Ile Thr Ala Thr Asp Gly Glu Asn Phe Ala Thr
                645                 650                 655

Pro Leu Tyr Ile Asn Leu Thr Val Ala Ala Ser Arg Lys Pro Val Asn
            660                 665                 670

Leu Gln Cys Glu Glu Thr Gly Val Ala Lys Met Leu Ala Glu Lys Leu
        675                 680                 685

Leu Gln Ala Asn Lys Leu His Ser Gln Gly Asp Val Glu Asp Ile Phe
```

-continued

```
                690                 695                 700
Phe Asp Ser Tyr Ser Val Asn Thr His Thr Pro Gln Phe Gly Val Thr
705                 710                 715                 720

Leu Pro Thr Gly Ile Glu Val Lys Glu Asn Leu Pro Val Gly Ala Asn
                725                 730                 735

Ile Leu Phe Met Asn Ala Thr Asp Leu Asp Ser Gly Phe Asn Gly Lys
                740                 745                 750

Leu Val Tyr Ala Ile Ser Gly Gly Asn Asp Asp Ser Cys Phe Thr Ile
                755                 760                 765

Asp Met Glu Thr Gly Val Leu Lys Val Leu Ser Pro Leu Asp Arg Glu
770                 775                 780

Val Met Asp Lys Tyr Thr Leu Asn Ile Thr Val Tyr Asp Leu Gly Ile
785                 790                 795                 800

Pro Gln Arg Ala Ala Trp Arg Leu Leu Asp Val Thr Val Leu Asp Ala
                805                 810                 815

Asn Asp Asn Ala Pro Glu Phe Leu Gln Glu Ser Tyr Phe Val Glu Val
                820                 825                 830

Ser Glu Asp Lys Glu Val Asn Ser Glu Ile Ile Gln Val Glu Ala Thr
                835                 840                 845

Asp Lys Asp Leu Gly Pro Ser Gly His Val Thr Tyr Ala Ile Leu Thr
                850                 855                 860

Asp Thr Glu Lys Phe Ser Ile Asp Ser Met Thr Gly Val Val Lys Ile
865                 870                 875                 880

Ile Gln Pro Leu Asp Arg Glu Val Gln Pro Val His Tyr Leu Lys Ile
                885                 890                 895

Glu Ala Arg Asp Gln Ala Thr Glu Glu Pro Arg Leu Phe Ser Thr Val
                900                 905                 910

Leu Leu Lys Val Ser Leu Asp Asp Val Asn Asp Asn Pro Pro Arg Phe
                915                 920                 925

Ile Pro Pro Asn Tyr Ser Val Lys Val Arg Glu Asp Leu Pro Glu Gly
                930                 935                 940

Thr Ile Ile Met Trp Leu Glu Ala Tyr Asp Pro Asp Val Gly Gln Ser
945                 950                 955                 960

Ser Gln Val Arg Tyr Ser Leu Leu Asp His Gly Glu Gly His Phe Asp
                965                 970                 975

Val Asp Lys Leu Ser Gly Ala Val Arg Ile Val Gln Gln Leu Asp Phe
                980                 985                 990

Glu Lys Lys Gln Leu Tyr Asn Leu Thr Val Arg Ala Lys Asp Lys Gly
                995                 1000                1005

Lys Pro Val Ser Leu Ser Ser Thr Cys Tyr Val Glu Val Glu Val
     1010                1015                1020

Val Asp Val Asn Glu Asn Leu His Thr Pro Val Phe Ser Ser Phe
     1025                1030                1035

Val Glu Lys Gly Val Val Lys Gly Asp Val Pro Thr Gly Ser Ser
     1040                1045                1050

Val Met Thr Val Ser Ala His Asp Glu Asp Thr Gly Arg Asp Gly
     1055                1060                1065

Glu Ile Arg Tyr Ser Ile Arg Asp Gly Ser Gly Ile Gly Val Phe
     1070                1075                1080

Arg Ile Asp Glu Glu Thr Gly Val Ile Glu Thr Ser Asp Arg Leu
     1085                1090                1095

Asp Arg Glu Ser Thr Ser His Tyr Trp Leu Thr Val Tyr Ala Thr
     1100                1105                1110
```

```
Asp Gln Gly Val Val Pro Leu Ser Ser Phe Ile Glu Val Tyr Ile
1115                1120                1125

Glu Val Glu Asp Val Asn Asp Asn Ala Pro Gln Thr Ser Glu Pro
1130                1135                1140

Val Tyr Tyr Pro Glu Ile Met Glu Asn Ser Pro Lys Asp Val Ser
1145                1150                1155

Val Val Gln Ile Glu Ala Phe Asp Pro Asp Ser Ser Asn Asp
1160                1165                1170

Lys Leu Thr Tyr Arg Ile Thr Ser Gly Asn Pro Gln Gly Phe Phe
1175                1180                1185

Ser Ile His Pro Lys Thr Gly Leu Ile Thr Thr Ser Arg Lys
1190                1195                1200

Leu Asp Arg Glu Gln Gln Asp Glu His Ile Leu Glu Val Thr Val
1205                1210                1215

Thr Asp Asn Gly Val Pro Pro Arg Ser Thr Ile Ala Arg Val Ile
1220                1225                1230

Val Lys Ile Leu Asp Glu Asn Asp Asn Arg Pro Gln Phe Leu Gln
1235                1240                1245

Lys Phe Tyr Lys Ile Arg Leu Pro Glu Arg Glu Lys Ala Asp Gly
1250                1255                1260

Asp Arg Ser Ala Ser Lys Arg Glu Pro Leu Tyr Arg Val Ile Ala
1265                1270                1275

Ala Asp Lys Asp Glu Gly Pro Asn Ala Glu Leu Ser Tyr Ser Ile
1280                1285                1290

Glu Glu Gly Asn Glu His Gly Arg Phe Ser Ile Glu Pro Lys Thr
1295                1300                1305

Gly Val Val Ser Ser Lys Lys Phe Ser Ala Ala Gly Glu Tyr Asp
1310                1315                1320

Ile Leu Ser Ile Lys Ala Val Asp Asn Gly Arg Pro Gln Lys Ser
1325                1330                1335

Ser Thr Thr Arg Leu His Ile Glu Trp Ile Ser Lys Pro Lys Pro
1340                1345                1350

Ser Ser Glu Pro Ile Ser Phe Glu Glu Ser Val Phe Ser Phe Thr
1355                1360                1365

Val Met Glu Ser Asp Pro Val Ala His Met Ile Gly Val Ile Ser
1370                1375                1380

Val Glu Pro Pro Gly Met Pro Leu Trp Phe Asp Ile Ile Gly Gly
1385                1390                1395

Asn Tyr Asp Ser His Phe Asp Val Asp Lys Gly Thr Gly Thr Ile
1400                1405                1410

Ile Val Ala Lys Pro Leu Asp Ala Glu Gln Lys Ser Ser Tyr Asn
1415                1420                1425

Leu Thr Val Glu Ala Thr Asp Gly Thr Thr Thr Ile Leu Thr Gln
1430                1435                1440

Val Leu Ile Lys Val Ile Asp Thr Asn Asp His Arg Pro Gln Phe
1445                1450                1455

Ser Thr Ser Lys Tyr Glu Val Ala Val Pro Glu Asp Thr Glu Pro
1460                1465                1470

Glu Val Glu Ile Leu Gln Ile Ser Ala Val Asp Arg Asp Glu Lys
1475                1480                1485

Asn Lys Leu Ile Tyr Thr Leu Gln Ser Ser Ile Asp Pro Ala Ser
1490                1495                1500

Leu Lys Lys Phe Arg Leu Asp Pro Ala Thr Gly Ala Leu Tyr Thr
1505                1510                1515
```

```
Ala Glu Lys Leu Asp His Glu Ala Ile His Gln His Val Leu Thr
    1520                1525                1530

Val Met Val Arg Asp Gln Asp Val Pro Val Lys Arg Asn Phe Ala
    1535                1540                1545

Arg Ile Val Val Asn Val Ser Asp Lys Asn Asp His Ala Pro Trp
    1550                1555                1560

Phe Thr Ser Pro Ser Tyr Asp Gly Arg Val Tyr Glu Ser Ala Ala
    1565                1570                1575

Val Gly Ser Val Val Leu Gln Val Thr Ala Leu Asp Lys Asp Lys
    1580                1585                1590

Gly Arg Asn Ala Glu Val Leu Tyr Ser Ile Glu Ser Gly Asn Ile
    1595                1600                1605

Gly Asn Ser Phe Thr Ile Asp Pro Ile Leu Gly Ser Ile Lys Thr
    1610                1615                1620

Ala Arg Glu Leu Asp Arg Ser His Gln Val Asp Tyr Asp Leu Met
    1625                1630                1635

Val Lys Ala Thr Asp Lys Gly Asp Pro Pro Met Ser Glu Met Thr
    1640                1645                1650

Ser Val Arg Ile Ala Val Thr Val Ala Asp Asn Ala Ser Pro Lys
    1655                1660                1665

Phe Thr Ser Lys Glu Tyr Ser Ala Glu Ile Ser Glu Ala Ile Arg
    1670                1675                1680

Ile Gly Ser Phe Val Gly Met Val Ser Ala His Ser Gln Ser Ser
    1685                1690                1695

Val Met Tyr Glu Ile Arg Asp Gly Asn Met Gly Asp Ala Phe Asn
    1700                1705                1710

Ile Asn Pro His Ser Gly Ser Ile Ile Thr Gln Arg Ala Leu Asp
    1715                1720                1725

Phe Glu Thr Leu Pro Met Tyr Ser Leu Thr Val Gln Gly Thr Asn
    1730                1735                1740

Met Ala Gly Leu Ser Thr Asn Thr Thr Val Val His Val Arg
    1745                1750                1755

Asp Glu Asn Asp Asn Pro Pro Val Phe Thr Gln Ala Glu Tyr Ser
    1760                1765                1770

Gly Phe Ile Ser Glu Ser Ala Ser Val Asn Ser Val Val Leu Thr
    1775                1780                1785

Asp Arg Asn Val Pro Leu Val Ile Arg Ala Thr Asp Ala Asp Arg
    1790                1795                1800

Glu Ser Asn Ala Leu Leu Val Tyr Gln Ile Val Glu Pro Ser Val
    1805                1810                1815

His Asn Tyr Phe Ala Ile Asp Pro Thr Thr Gly Ala Ile Arg Thr
    1820                1825                1830

Val Leu Ser Leu Asp Tyr Glu Glu Thr His Ala Phe His Phe Thr
    1835                1840                1845

Val Gln Val His Asp Met Gly Thr Pro Arg Leu Phe Ala Glu Tyr
    1850                1855                1860

Ala Ala Asn Val Thr Val His Val Ile Asp Ile Asn Asp Cys Pro
    1865                1870                1875

Pro Val Phe Ser Lys Ser Leu Tyr Glu Val Ser Leu Leu Leu Pro
    1880                1885                1890

Thr Tyr Arg Gly Val Asn Val Ile Thr Val Asn Ala Thr Asp Ala
    1895                1900                1905

Asp Ser Lys Ala Phe Ser Gln Val Met Tyr Ser Ile Thr Glu Gly
```

-continued

```
                1910                1915                1920

Asn Ile Gly Glu Lys Phe Ser Met Asp His Lys Thr Gly Thr Ile
    1925                1930                1935

Ala Ile Gln Asn Thr Thr Gln Leu Arg Ser Arg Tyr Glu Leu Thr
    1940                1945                1950

Val Arg Ala Ser Asp Gly Arg Phe Thr Ser Met Ala Ser Val Lys
    1955                1960                1965

Ile Asn Val Lys Glu Ser Arg Glu Ser Pro Leu Lys Phe Thr Gln
    1970                1975                1980

Asp Ala Tyr Ser Ala Val Val Lys Glu Asn Ser Thr Glu Ala Arg
    1985                1990                1995

Thr Leu Ala Val Ile Thr Ala Ile Gly Asn Pro Leu Asn Glu Pro
    2000                2005                2010

Leu Phe Tyr Arg Ile Leu Asn Pro Asp Arg Arg Phe Lys Ile Ser
    2015                2020                2025

His Thr Ser Gly Val Leu Ser Thr Thr Gly Ile Pro Phe Asp Arg
    2030                2035                2040

Glu Gln Gln Glu Thr Phe Asp Val Val Val Glu Val Thr Lys Glu
    2045                2050                2055

His Glu Pro Ser Ala Val Ala His Val Val Lys Val Thr Val
    2060                2065                2070

Glu Asp Gln Asn Asp Asn Ala Pro Val Phe Val Asn Leu Pro Tyr
    2075                2080                2085

Tyr Ala Val Val Lys Val Asp Ala Glu Val Gly His Val Ile Arg
    2090                2095                2100

Tyr Val Thr Ala Ile Asp Arg Asp Ser Gly Arg Asn Gly Asp Ile
    2105                2110                2115

His Tyr Tyr Leu Lys Glu His His Asp His Phe Gln Ile Gly Pro
    2120                2125                2130

Ser Gly Asp Ile Ser Leu Lys Lys Gln Phe Glu His Asp Thr Leu
    2135                2140                2145

Asn Lys Glu Tyr Leu Val Thr Val Val Ala Lys Asp Gly Gly Ser
    2150                2155                2160

Pro Ala Phe Ser Ala Glu Val Leu Val Pro Ile Thr Val Met Asn
    2165                2170                2175

Lys Ala Met Pro Val Phe Glu Lys Ala Phe Tyr Ser Ala Glu Ile
    2180                2185                2190

Pro Glu Asn Ile Gln Met His Ser Pro Val Val His Ile Gln Ala
    2195                2200                2205

Asn Ser Pro Glu Gly Leu Lys Val Phe Tyr Ser Ile Thr Asp Gly
    2210                2215                2220

Asp Pro Phe Ser Gln Phe Thr Ile Asn Phe Asn Thr Gly Val Val
    2225                2230                2235

Asn Val Ile Ala Pro Leu Asp Phe Glu Ser His Pro Ala Tyr Lys
    2240                2245                2250

Leu Ser Val Arg Ala Thr Asp Ser Leu Thr Gly Ala His Ala Glu
    2255                2260                2265

Val Phe Val Asp Ile Ile Val Glu Asp Ile Asn Asp Asn Pro Pro
    2270                2275                2280

Val Phe Val Gln Pro Ser Tyr Ser Thr Thr Leu Ser Glu Ala Ser
    2285                2290                2295

Val Ile Gly Thr Pro Val Leu Gln Val Arg Ala Thr Asp Ser Asp
    2300                2305                2310
```

-continued

Ser Glu Pro Asn Arg Gly Ile Ser Tyr Gln Leu Ile Gly Asn His
2315                2320                2325

Ser Lys Ser His Asp His Phe His Ile Asp Ser Asn Thr Gly Leu
2330                2335                2340

Ile Ser Leu Val Arg Ala Leu Asp Tyr Glu Gln Ser Gln Gln His
2345                2350                2355

Arg Ile Phe Val Arg Ala Val Asp Gly Gly Met Pro Ala Leu Ser
2360                2365                2370

Ser Asp Val Val Val Thr Val Ala Val Thr Asp Leu Asn Asp Asn
2375                2380                2385

Pro Pro Leu Phe Glu Gln Gln Val Tyr Glu Ala Arg Ile Ser Glu
2390                2395                2400

His Ala Ala His Gly His Phe Val Met Cys Val Arg Ala Cys Asp
2405                2410                2415

Ala Asp Ser Ser Asp Leu Asp Lys Leu Glu Tyr Ser Ile Leu Ser
2420                2425                2430

Gly Asn Asp His Lys Ser Phe Ile Ile Asp Arg Glu Thr Gly Ile
2435                2440                2445

Ile Thr Leu Ser Asn Leu Arg Arg His Thr Leu Lys Pro Phe Tyr
2450                2455                2460

Ser Leu Asn Val Ser Val Ser Asp Gly Val Phe Arg Ser Ser Ala
2465                2470                2475

Arg Val Asn Val Thr Val Met Gly Gly Asn Leu His Ser Pro Val
2480                2485                2490

Phe His Gln Asn Glu Tyr Glu Val Glu Leu Ala Glu Asn Ala Pro
2495                2500                2505

Leu His Thr Leu Val Val Gln Val Lys Ala Ser Asp Arg Asp Ser
2510                2515                2520

Gly Ile Tyr Ser His Val Thr Tyr His Ile Val Asn Asp Phe Ala
2525                2530                2535

Lys Asp Arg Phe Tyr Val Asn Asp Arg Gly Gln Ile Phe Thr Leu
2540                2545                2550

Glu Lys Leu Asp Arg Glu Thr Pro Ala Glu Lys Val Ile Ser Ile
2555                2560                2565

Arg Leu Met Ala Lys Asp Ala Gly Gly Lys Val Ala Phe Cys Thr
2570                2575                2580

Val Asn Val Ile Leu Thr Asp Asp Asn Asp Asn Ala Pro Gln Phe
2585                2590                2595

Arg Ser Thr Lys Tyr Glu Val Asn Ile Gly Ser Ser Ala Ala Lys
2600                2605                2610

Gly Thr Ser Val Val Lys Val Phe Ala Ser Asp Ala Asp Glu Gly
2615                2620                2625

Ser Asn Ala Asp Val Thr Tyr Ala Ile Glu Ala Asp Ser Glu Ser
2630                2635                2640

Val Lys Glu Asn Leu Glu Ile Asn Lys Leu Thr Gly Leu Ile Thr
2645                2650                2655

Thr Lys Glu Ser Leu Ile Gly Leu Glu Asn Glu Phe Phe Thr Phe
2660                2665                2670

Phe Val Arg Ala Val Asp Ser Gly Ser Pro Arg Glu Ser Val
2675                2680                2685

Val Pro Val Tyr Ile Lys Ile Leu Pro Pro Glu Val Gln Leu Pro
2690                2695                2700

Arg Phe Ser Glu Pro Phe Tyr Thr Tyr Thr Ile Ser Glu Asp Thr
2705                2710                2715

-continued

```
Pro Ile Gly Thr Glu Ile Asp Leu Ile Arg Val Glu His Gly Gly
    2720            2725                2730
Ala Val Leu Tyr Ile Leu Val Lys Gly Asn Thr Pro Glu Ser Asn
    2735            2740                2745
Arg Asp Glu Phe Phe Val Ile Asp Arg Gln Asn Gly Arg Leu Lys
    2750            2755                2760
Leu Glu Lys Ser Leu Asp His Glu Thr Thr Lys Trp Tyr Gln Phe
    2765            2770                2775
Ser Ile Leu Ala Arg Cys Thr Leu Asp Asp Tyr Glu Val Val Ala
    2780            2785                2790
Ser Ile Asp Val Ser Ile Gln Val Lys Asp Ala Asn Asp Asn Ser
    2795            2800                2805
Pro Val Leu Glu Ser Ser Pro Tyr Glu Ala Phe Ile Val Glu Asn
    2810            2815                2820
Leu Pro Gly Gly Ser Arg Val Ile Gln Ile Arg Ala Ser Asp Leu
    2825            2830                2835
Asp Ser Gly Ala Asn Gly Gln Val Met Tyr Ser Leu Asp Gln Ser
    2840            2845                2850
Gln Asp Ala Asp Ile Ile Glu Ser Phe Ala Ile Asn Met Glu Thr
    2855            2860                2865
Gly Trp Ile Thr Thr Leu Lys Glu Leu Asp His Glu Glu Arg Ala
    2870            2875                2880
Ser Tyr Gln Ile Lys Val Val Ala Ser Asp His Gly Glu Lys Val
    2885            2890                2895
Gln Leu Ser Ser Thr Ala Ile Val Gly Val Thr Val Thr Asp Val
    2900            2905                2910
Asn Asp Ser Pro Pro Arg Phe Thr Ala Glu Ile Tyr Lys Gly Thr
    2915            2920                2925
Val Ser Glu Asp Asp Pro Pro Gly Gly Val Ile Ala Ile Leu Ser
    2930            2935                2940
Thr Thr Asp Ala Asp Thr Glu Glu Ile Asn Arg Gln Val Ser Tyr
    2945            2950                2955
Phe Ile Thr Gly Gly Asp Ala Leu Gly Gln Phe Ala Val Glu Asn
    2960            2965                2970
Val Gln Ser Asp Trp Arg Val Tyr Val Lys Lys Pro Leu Asp Arg
    2975            2980                2985
Glu Gln Lys Asp Ser Tyr Leu Leu Thr Val Thr Ala Thr Asp Gly
    2990            2995                3000
Thr Phe Ser Ser Lys Ala Arg Val Glu Val Lys Val Leu Asp Ala
    3005            3010                3015
Asn Asp Asn Ser Pro Val Cys Glu Lys Thr Ser Tyr Ser Asp Thr
    3020            3025                3030
Ile Pro Glu Asp Ala Leu Pro Gly Lys Leu Val Met Gln Val Ser
    3035            3040                3045
Ala Thr Asp Ala Asp Ile Arg Ser Asn Ala Glu Ile Thr Tyr Thr
    3050            3055                3060
Leu Phe Gly Ser Gly Ala Glu Lys Phe Lys Leu Asn Pro Asp Thr
    3065            3070                3075
Gly Glu Leu Arg Thr Leu Ala Leu Leu Asp Arg Glu Glu Gln Ala
    3080            3085                3090
Val Tyr Asn Leu Leu Val Lys Ala Thr Asp Gly Gly Gly Arg Ser
    3095            3100                3105
Cys Gln Ala Ala Ile Val Leu Thr Leu Glu Asp Val Asn Asp Asn
```

```
                3110                3115                3120
Ala Pro Glu Phe Thr Ala Glu Pro Tyr Thr Ile Thr Val Phe Glu
    3125                3130                3135

Asn Thr Glu Pro Gly Thr Pro Leu Thr Arg Val Gln Ala Thr Asp
    3140                3145                3150

Ala Asp Thr Gly Leu Asn Arg Lys Ile Ser Tyr Ser Leu Val Glu
    3155                3160                3165

Ser Ala Asp Gly Gln Phe Ser Ile Asn Glu Arg Ser Gly Ile Ile
    3170                3175                3180

Gln Leu Glu Lys His Leu Asp Arg Glu Leu Gln Ala Val Tyr Thr
    3185                3190                3195

Leu Thr Leu Lys Ala Val Asp Gln Gly Leu Pro Arg Arg Leu Thr
    3200                3205                3210

Ala Thr Gly Thr Val Val Val Ser Val Leu Asp Ile Asn Asp Asn
    3215                3220                3225

Pro Pro Val Phe Glu Tyr Arg Glu Tyr Gly Ala Ser Val Ser Glu
    3230                3235                3240

Asp Ile Val Ile Gly Thr Glu Val Leu Gln Val Tyr Ala Ala Ser
    3245                3250                3255

Arg Asp Ile Glu Ala Asn Ala Glu Ile Thr Tyr Ala Ile Ile Ser
    3260                3265                3270

Gly Asn Glu His Gly Lys Phe Ser Ile Asp Ser Lys Thr Gly Ala
    3275                3280                3285

Ile Phe Ile Ile Glu Ser Leu Asp Tyr Glu Ser Ser His Glu Tyr
    3290                3295                3300

Tyr Leu Thr Val Glu Ala Thr Asp Gly Gly Thr Pro Ser Leu Ser
    3305                3310                3315

Asp Val Ala Thr Val Asn Ile Asn Val Thr Asp Ile Asn Asp Asn
    3320                3325                3330

Ser Pro Val Phe Ser Gln Asp Thr Tyr Thr Thr Val Val Ser Glu
    3335                3340                3345

Asp Ala Ala Leu Glu Gln Pro Val Ile Thr Ile Met Ala Asp Asp
    3350                3355                3360

Ala Asp Gly Pro Ser Asn Ser His Ile His Tyr Ser Ile Ile Glu
    3365                3370                3375

Gly Asn Gln Gly Ser Pro Phe Thr Ile Asp Pro Val Arg Gly Glu
    3380                3385                3390

Val Lys Val Thr Lys Pro Leu Asp Arg Glu Thr Ile Ser Gly Tyr
    3395                3400                3405

Thr Leu Thr Val Gln Ala Ala Asp Asn Gly Asn Pro Pro Arg Val
    3410                3415                3420

Asn Thr Thr Thr Val Asn Ile Asp Val Ser Asp Val Asn Asp Asn
    3425                3430                3435

Ala Pro Leu Phe Ser Arg Asp Asn Tyr Ser Val Ile Ile Gln Glu
    3440                3445                3450

Asn Lys Pro Val Gly Phe Ser Val Leu Lys Leu Val Val Thr Asp
    3455                3460                3465

Lys Asp Ser Ser His Asn Gly Pro Pro Phe Phe Phe Thr Ile Val
    3470                3475                3480

Ser Gly Asn Asp Glu Asn Ala Phe Glu Val Asn Gln His Gly Val
    3485                3490                3495

Leu Leu Thr Ala Ala Thr Ile Lys Arg Lys Val Lys Asp His Tyr
    3500                3505                3510
```

-continued

| | | | | | | | | | | | |
|---|---|---|---|---|---|---|---|---|---|---|---|
| Leu | Leu | His | Val | Lys | Val | Ala | Asp | Ser | Gly | Lys | Pro | Gln | Leu | Ser |
| 3515 | | | | 3520 | | | | | 3525 | | | | | |
| Ser | Met | Thr | His | Ile | Asp | Ile | Arg | Val | Ile | Glu | Glu | Ser | Ile | His |
| 3530 | | | | | 3535 | | | | | 3540 | | | | |
| Pro | Pro | Ala | Ile | Leu | Pro | Leu | Glu | Ile | Phe | Ile | Thr | Ala | Phe | Gly |
| 3545 | | | | | 3550 | | | | | 3555 | | | | |
| Glu | Glu | Tyr | Ser | Gly | Gly | Val | Ile | Gly | Lys | Ile | His | Ala | Thr | Asp |
| 3560 | | | | | 3565 | | | | | 3570 | | | | |
| Gln | Asp | Val | Tyr | Asp | Thr | Leu | Met | Tyr | Ser | Leu | Asp | Pro | His | Met |
| 3575 | | | | | 3580 | | | | | 3585 | | | | |
| Asp | Gly | Leu | Phe | Ser | Val | Ser | Ser | Thr | Gly | Gly | Lys | Leu | Ile | Ala |
| 3590 | | | | | 3595 | | | | | 3600 | | | | |
| His | Arg | Lys | Leu | Asp | Ile | Gly | Gln | Tyr | Leu | Leu | Asn | Val | Ser | Val |
| 3605 | | | | | 3610 | | | | | 3615 | | | | |
| Thr | Asp | Gly | Lys | Phe | Thr | Thr | Val | Ala | Asp | Ile | Thr | Val | His | Ile |
| 3620 | | | | | 3625 | | | | | 3630 | | | | |
| Gln | Gln | Val | Thr | Gln | Glu | Met | Leu | Asn | His | Thr | Val | Ala | Ile | Arg |
| 3635 | | | | | 3640 | | | | | 3645 | | | | |
| Phe | Ala | Asn | Leu | Thr | Pro | Glu | Glu | Phe | Val | Gly | Asp | Tyr | Trp | Arg |
| 3650 | | | | | 3655 | | | | | 3660 | | | | |
| Asn | Phe | Gln | Arg | Ala | Leu | Arg | Asn | Ile | Leu | Gly | Val | Arg | Lys | Asn |
| 3665 | | | | | 3670 | | | | | 3675 | | | | |
| Asp | Ile | Gln | Ile | Val | Ser | Leu | Gln | Pro | Ser | Glu | Pro | His | Ser | His |
| 3680 | | | | | 3685 | | | | | 3690 | | | | |
| Leu | Asp | Val | Leu | Leu | Phe | Val | Glu | Arg | Ser | Gly | Gly | Thr | His | Val |
| 3695 | | | | | 3700 | | | | | 3705 | | | | |
| Ser | Thr | Lys | Gln | Leu | Leu | His | Lys | Ile | Asn | Ser | Ser | Val | Thr | Asp |
| 3710 | | | | | 3715 | | | | | 3720 | | | | |
| Val | Glu | Glu | Ile | Ile | Gly | Val | Arg | Ile | Leu | Glu | Val | Phe | Gln | Lys |
| 3725 | | | | | 3730 | | | | | 3735 | | | | |
| Leu | Cys | Ala | Gly | Leu | Asp | Cys | Pro | Trp | Lys | Phe | Cys | Asp | Glu | Lys |
| 3740 | | | | | 3745 | | | | | 3750 | | | | |
| Val | Ser | Val | Asp | Glu | Asn | Val | Met | Ser | Thr | His | Ser | Thr | Ala | Arg |
| 3755 | | | | | 3760 | | | | | 3765 | | | | |
| Leu | Ser | Phe | Val | Thr | Pro | Arg | His | His | Arg | Thr | Ala | Val | Cys | Leu |
| 3770 | | | | | 3775 | | | | | 3780 | | | | |
| Cys | Lys | Asp | Gly | Thr | Cys | Pro | Pro | Val | His | His | Gly | Cys | Glu | Asp |
| 3785 | | | | | 3790 | | | | | 3795 | | | | |
| Asn | Pro | Cys | Pro | Ala | Gly | Ser | Glu | Cys | Val | Ala | Asp | Pro | Arg | Glu |
| 3800 | | | | | 3805 | | | | | 3810 | | | | |
| Glu | Lys | Tyr | Ser | Cys | Val | Cys | Pro | Gly | Gly | Gly | Phe | Gly | Lys | Cys |
| 3815 | | | | | 3820 | | | | | 3825 | | | | |
| Pro | Gly | Ser | Ser | Ser | Ile | Thr | Phe | Thr | Gly | Asn | Ser | Phe | Val | Lys |
| 3830 | | | | | 3835 | | | | | 3840 | | | | |
| Tyr | Arg | Leu | Leu | Glu | Asn | Glu | Asn | Arg | Leu | Glu | Met | Lys | Leu | Ser |
| 3845 | | | | | 3850 | | | | | 3855 | | | | |
| Met | Arg | Leu | Arg | Thr | Tyr | Ser | Ser | His | Ala | Val | Val | Met | Tyr | Ala |
| 3860 | | | | | 3865 | | | | | 3870 | | | | |
| Arg | Gly | Thr | Asp | Tyr | Ser | Ile | Pro | Gly | Ile | Val | Ser | Val | Gln | Ser |
| 3875 | | | | | 3880 | | | | | 3885 | | | | |
| Ile | Gln | Val | Asn | Asp | Gly | Gln | Trp | His | Ala | Val | Ser | Leu | Glu | Val |
| 3890 | | | | | 3895 | | | | | 3900 | | | | |
| Glu | Gly | Asn | Tyr | Ala | Lys | Leu | Val | Leu | Asp | Glu | Val | His | Thr | Ala |
| 3905 | | | | | 3910 | | | | | 3915 | | | | |

-continued

Ser Gly Thr Ala Pro Gly Ala Leu Lys Thr Leu Asn Leu Asp Asn
3920             3925                3930

Tyr Val Phe Phe Gly Gly His Leu Arg Gln Gln Gly Thr Lys His
3935             3940                3945

Gly Arg Gly Ala Gln Val Ala Ser Gly Phe Arg Gly Cys Met Asp
3950             3955                3960

Ser Ile Tyr Leu Asn Gly Gln Glu Leu Pro Leu Asn Asn Lys Pro
3965             3970                3975

Arg Ala Tyr Ala His Ile Glu Glu Trp Val Asp Leu Ser His Gly
3980             3985                3990

Cys Leu Leu Thr Ala Thr Glu Asp Cys Ser Ser Pro Cys Gln
3995             4000                4005

Asn Gly Gly Val Cys Asn Pro Ser Pro Thr Gly Gly Tyr Tyr Cys
4010             4015                4020

Lys Cys Ser Ala Leu Tyr Val Gly Thr Phe Cys Glu Val Ser Val
4025             4030                4035

Asn Pro Cys Ser Ser Asn Pro Cys Leu Tyr Gly Gly Thr Cys Met
4040             4045                4050

Val Asp Asn Gly Gly Phe Val Cys Gln Cys Arg Gly Leu Tyr Thr
4055             4060                4065

Gly Leu Val Leu Phe Phe Ser Phe Cys Met Cys Phe Ser Leu Phe
4070             4075                4080

Arg Cys Gln Leu Ser Pro Tyr Cys Lys Asp Asp Pro Cys Lys Asn
4085             4090                4095

Gly Gly Thr Cys Phe Asp Ser Leu Asp Gly Ala Val Cys Gln Cys
4100             4105                4110

Asp Ser Gly Phe Arg Gly Glu Arg Cys Gln Ser Asp Ile Asp Glu
4115             4120                4125

Cys Ala Gly Asn Pro Cys Arg Asn Gly Ala Leu Cys Glu Asn Thr
4130             4135                4140

His Gly Ser Tyr His Cys Asn Cys Ser Gln Glu Tyr Arg Gly Lys
4145             4150                4155

His Cys Glu Asp Ala Ser Pro Asn His Tyr Val Ser Thr Pro Trp
4160             4165                4170

Asn Ile Gly Leu Ala Glu Gly Ile Gly Ile Ile Val Phe Ile Ala
4175             4180                4185

Gly Ile Val Leu Leu Val Met Val Phe Val Leu Cys Arg Lys Met
4190             4195                4200

Ile Ser Arg Lys Lys Lys Arg Gln Ala Glu Pro Glu Asp Lys Arg
4205             4210                4215

Leu Gly Pro Thr Thr Ala Phe Leu Gln Arg Pro Tyr Phe Asp Ser
4220             4225                4230

Lys Leu Asn Lys Asn Ile Tyr Ser Asp Ile Pro Pro Gln Val Pro
4235             4240                4245

Val Arg Pro Ile Ser Tyr Thr Pro Ser Ile Pro Ser Asp Ser Arg
4250             4255                4260

Asn Asn Leu Asp Arg Asn Ser Phe Glu Gly Ser Ala Ile Pro Glu
4265             4270                4275

His Pro Glu Phe Ser Thr Phe Asn Pro Glu Ser Met His Gly His
4280             4285                4290

Arg Lys Ala Val Ala Val Cys Ser Val Ala Pro Asn Leu Pro Pro
4295             4300                4305

Pro Pro Pro Ser Asn Ser Pro Ser Asp Ser Asp Ser Ile Gln Lys

```
                 4310                4315                4320

Pro Ser Trp Asp Phe Asp Tyr Asp Ala Lys Val Val Asp Leu Asp
    4325                4330                4335

Pro Cys Leu Ser Lys Lys Pro Leu Glu Glu Lys Pro Ser Gln Pro
    4340                4345                4350

Tyr Ser Ala Arg Glu Ser Leu Ser Glu Val Gln Ser Leu Ser Ser
    4355                4360                4365

Phe Gln Ser Glu Ser Cys Asp Asp Asn Glu Ser Leu Ala Ala Pro
    4370                4375                4380

Asp Leu Ser Lys Pro Arg Gly Tyr His Trp Asp Thr Ser Asp Trp
    4385                4390                4395

Met Pro Ser Val Pro Leu Pro Asp Ile Gln Glu Phe Pro Asn Tyr
    4400                4405                4410

Glu Ala Ile Asp Glu His Thr Pro Leu Tyr Ser Ala Asp Pro Asn
    4415                4420                4425

Ala Ile Asp Thr Asp Tyr Tyr Pro Gly Gly Tyr Asp Ile Glu Ser
    4430                4435                4440

Asp Phe Pro Pro Pro Glu Asp Phe Pro Ala Pro Asp Glu Leu
    4445                4450                4455

Pro Pro Leu Pro Pro Glu Phe Ser Asp Gln Phe Glu Ser Ile His
    4460                4465                4470

Pro Pro Arg Asp Met Pro Ala Ala Gly Ser Leu Gly Ser Ser Ser
    4475                4480                4485

Arg Ser Arg Gln Arg Phe Asn Leu Asn Gln Tyr Leu Pro Asn Phe
    4490                4495                4500

Tyr Pro Ala Asp Met Ser Glu Pro Gln Lys Gln Gly Ala Gly Glu
    4505                4510                4515

Asn Ser Pro Cys Arg Glu Pro Tyr Thr Pro Tyr Pro Pro Gly Tyr
    4520                4525                4530

Gln Arg Asn Phe Glu Ala Pro Thr Ile Glu Asn Met Pro Met Ser
    4535                4540                4545

Val Tyr Ala Ser Thr Ala Ser Cys Ser Asp Val Ser Ala Cys Cys
    4550                4555                4560

Glu Val Glu Ser Glu Val Met Met Ser Asp Tyr Glu Ser Gly Asp
    4565                4570                4575

Asp Gly His Phe Glu Glu Val Thr Ile Pro Pro Leu Asp Ser Gln
    4580                4585                4590

Gln His Thr Glu Val
    4595

<210> SEQ ID NO 2
<211> LENGTH: 4588
<212> TYPE: PRT
<213> ORGANISM: Homo sapiens

<400> SEQUENCE: 2

Met Gly Arg His Leu Ala Leu Leu Leu Leu Leu Leu Leu Phe Gln
1               5                   10                  15

His Phe Gly Asp Ser Asp Gly Ser Gln Arg Leu Glu Gln Thr Pro Leu
                20                  25                  30

Gln Phe Thr His Leu Glu Tyr Asn Val Thr Val Gln Glu Asn Ser Ala
        35                  40                  45

Ala Lys Thr Tyr Val Gly His Pro Val Lys Met Gly Val Tyr Ile Thr
    50                  55                  60

His Pro Ala Trp Glu Val Arg Tyr Lys Ile Val Ser Gly Asp Ser Glu
```

```
                 65                  70                  75                  80
Asn Leu Phe Lys Ala Glu Glu Tyr Ile Leu Gly Asp Phe Cys Phe Leu
                 85                  90                  95

Arg Ile Arg Thr Lys Gly Gly Asn Thr Ala Ile Leu Asn Arg Glu Val
                100                 105                 110

Lys Asp His Tyr Thr Leu Ile Val Lys Ala Leu Glu Lys Asn Thr Asn
                115                 120                 125

Val Glu Ala Arg Thr Lys Val Arg Val Gln Val Leu Asp Thr Asn Asp
            130                 135                 140

Leu Arg Pro Leu Phe Ser Pro Thr Ser Tyr Ser Val Ser Leu Pro Glu
145                 150                 155                 160

Asn Thr Ala Ile Arg Thr Ser Ile Ala Arg Val Ser Ala Thr Asp Ala
                165                 170                 175

Asp Ile Gly Thr Asn Gly Glu Phe Tyr Tyr Ser Phe Lys Asp Arg Thr
                180                 185                 190

Asp Met Phe Ala Ile His Pro Thr Ser Gly Val Ile Val Leu Thr Gly
                195                 200                 205

Arg Leu Asp Tyr Leu Glu Thr Lys Leu Tyr Glu Met Glu Ile Leu Ala
            210                 215                 220

Ala Asp Arg Gly Met Lys Leu Tyr Gly Ser Ser Gly Ile Ser Ser Met
225                 230                 235                 240

Ala Lys Leu Thr Val His Ile Glu Gln Ala Asn Glu Cys Ala Pro Val
                245                 250                 255

Ile Thr Ala Val Thr Leu Ser Pro Ser Glu Leu Asp Arg Asp Pro Ala
                260                 265                 270

Tyr Ala Ile Val Thr Val Asp Asp Cys Asp Gln Gly Ala Asn Gly Asp
            275                 280                 285

Ile Ala Ser Leu Ser Ile Val Ala Gly Asp Leu Leu Gln Gln Phe Arg
                290                 295                 300

Thr Val Arg Ser Phe Pro Gly Ser Lys Glu Tyr Lys Val Lys Ala Ile
305                 310                 315                 320

Gly Gly Ile Asp Trp Asp Ser His Pro Phe Gly Tyr Asn Leu Thr Leu
                325                 330                 335

Gln Ala Lys Asp Lys Gly Thr Pro Pro Gln Phe Ser Ser Val Lys Val
                340                 345                 350

Ile His Val Thr Ser Pro Gln Phe Lys Ala Gly Pro Val Lys Phe Glu
            355                 360                 365

Lys Asp Val Tyr Arg Ala Glu Ile Ser Glu Phe Ala Pro Pro Asn Thr
            370                 375                 380

Pro Val Val Met Val Lys Ala Ile Pro Ala Tyr Ser His Leu Arg Tyr
385                 390                 395                 400

Val Phe Lys Ser Thr Pro Gly Lys Ala Lys Phe Ser Leu Asn Tyr Asn
                405                 410                 415

Thr Gly Leu Ile Ser Ile Leu Glu Pro Val Lys Arg Gln Gln Ala Ala
                420                 425                 430

His Phe Glu Leu Glu Val Thr Thr Ser Asp Arg Lys Ala Ser Thr Lys
            435                 440                 445

Val Leu Val Lys Val Leu Gly Ala Asn Ser Asn Pro Pro Glu Phe Thr
450                 455                 460

Gln Thr Ala Tyr Lys Ala Ala Phe Asp Glu Asn Val Pro Ile Gly Thr
465                 470                 475                 480

Thr Val Met Ser Leu Ser Ala Val Asp Pro Asp Glu Gly Glu Asn Gly
                485                 490                 495
```

-continued

Tyr Val Thr Tyr Ser Ile Ala Asn Leu Asn His Val Pro Phe Ala Ile
            500                 505                 510

Asp His Phe Thr Gly Ala Val Ser Thr Ser Glu Asn Leu Asp Tyr Glu
            515                 520                 525

Leu Met Pro Arg Val Tyr Thr Leu Arg Ile Arg Ala Ser Asp Trp Gly
            530                 535                 540

Leu Pro Tyr Arg Arg Glu Val Glu Val Leu Ala Thr Ile Thr Leu Asn
545                 550                 555                 560

Asn Leu Asn Asp Asn Thr Pro Leu Phe Glu Lys Ile Asn Cys Glu Gly
                565                 570                 575

Thr Ile Pro Arg Asp Leu Gly Val Gly Glu Gln Ile Thr Val Ser
            580                 585                 590

Ala Ile Asp Ala Asp Glu Leu Gln Leu Val Gln Tyr Gln Ile Glu Ala
            595                 600                 605

Gly Asn Glu Leu Asp Phe Phe Ser Leu Asn Pro Asn Ser Gly Val Leu
            610                 615                 620

Ser Leu Lys Arg Ser Leu Met Asp Gly Leu Gly Ala Lys Val Ser Phe
625                 630                 635                 640

His Ser Leu Arg Ile Thr Ala Thr Asp Gly Glu Asn Phe Ala Thr Pro
                645                 650                 655

Leu Tyr Ile Asn Ile Thr Val Ala Ala Ser His Lys Leu Val Asn Leu
            660                 665                 670

Gln Cys Glu Glu Thr Gly Val Ala Lys Met Leu Ala Glu Lys Leu Leu
            675                 680                 685

Gln Ala Asn Lys Leu His Asn Gln Gly Glu Val Glu Asp Ile Phe Phe
            690                 695                 700

Asp Ser His Ser Val Asn Ala His Ile Pro Gln Phe Arg Ser Thr Leu
705                 710                 715                 720

Pro Thr Gly Ile Gln Val Lys Glu Asn Gln Pro Val Gly Ser Ser Val
                725                 730                 735

Ile Phe Met Asn Ser Thr Asp Leu Asp Thr Gly Phe Asn Gly Lys Leu
            740                 745                 750

Val Tyr Ala Val Ser Gly Gly Asn Glu Asp Ser Cys Phe Met Ile Asp
            755                 760                 765

Met Glu Thr Gly Met Leu Lys Ile Leu Ser Pro Leu Asp Arg Glu Thr
            770                 775                 780

Thr Asp Lys Tyr Thr Leu Asn Ile Thr Val Tyr Asp Leu Gly Ile Pro
785                 790                 795                 800

Gln Lys Ala Ala Trp Arg Leu Leu His Val Val Val Asp Ala Asn
                805                 810                 815

Asp Asn Pro Pro Glu Phe Leu Gln Glu Ser Tyr Phe Val Glu Val Ser
            820                 825                 830

Glu Asp Lys Glu Val His Ser Glu Ile Ile Gln Val Glu Ala Thr Asp
            835                 840                 845

Lys Asp Leu Gly Pro Asn Gly His Val Thr Tyr Ser Ile Val Thr Asp
            850                 855                 860

Thr Asp Thr Phe Ser Ile Asp Ser Val Thr Gly Val Val Asn Ile Ala
865                 870                 875                 880

Arg Pro Leu Asp Arg Glu Leu Gln His Glu His Ser Leu Lys Ile Glu
                885                 890                 895

Ala Arg Asp Gln Ala Arg Glu Glu Pro Gln Leu Phe Ser Thr Val Val
            900                 905                 910

Val Lys Val Ser Leu Glu Asp Val Asn Asp Asn Pro Pro Thr Phe Ile
            915                 920                 925

```
Pro Pro Asn Tyr Arg Val Lys Val Arg Glu Asp Leu Pro Glu Gly Thr
    930                 935                 940

Val Ile Met Trp Leu Glu Ala His Asp Pro Asp Leu Gly Gln Ser Gly
945                 950                 955                 960

Gln Val Arg Tyr Ser Leu Leu Asp His Gly Glu Gly Asn Phe Asp Val
            965                 970                 975

Asp Lys Leu Ser Gly Ala Val Arg Ile Val Gln Gln Leu Asp Phe Glu
        980                 985                 990

Lys Lys Gln Val Tyr Asn Leu Thr Val Arg Ala Lys Asp Lys Gly Lys
    995                 1000                1005

Pro Val Ser Leu Ser Ser Thr Cys Tyr Val Glu Val Glu Val Val
    1010                1015                1020

Asp Val Asn Glu Asn Leu His Pro Pro Val Phe Ser Ser Phe Val
    1025                1030                1035

Glu Lys Gly Thr Val Lys Glu Asp Ala Pro Val Gly Ser Leu Val
    1040                1045                1050

Met Thr Val Ser Ala His Asp Glu Asp Ala Arg Arg Asp Gly Glu
    1055                1060                1065

Ile Arg Tyr Ser Ile Arg Asp Gly Ser Gly Val Gly Val Phe Lys
    1070                1075                1080

Ile Gly Glu Glu Thr Gly Val Ile Glu Thr Ser Asp Arg Leu Asp
    1085                1090                1095

Arg Glu Ser Thr Ser His Tyr Trp Leu Thr Val Phe Ala Thr Asp
    1100                1105                1110

Gln Gly Val Val Pro Leu Ser Ser Phe Ile Glu Ile Tyr Ile Glu
    1115                1120                1125

Val Glu Asp Val Asn Asp Asn Ala Pro Gln Thr Ser Glu Pro Val
    1130                1135                1140

Tyr Tyr Pro Glu Ile Met Glu Asn Ser Pro Lys Asp Val Ser Val
    1145                1150                1155

Val Gln Ile Glu Ala Phe Asp Pro Asp Ser Ser Asn Asp Lys
    1160                1165                1170

Leu Met Tyr Lys Ile Thr Ser Gly Asn Pro Gln Gly Phe Phe Ser
    1175                1180                1185

Ile His Pro Lys Thr Gly Leu Ile Thr Thr Thr Ser Arg Lys Leu
    1190                1195                1200

Asp Arg Glu Gln Gln Asp Glu His Ile Leu Glu Val Thr Val Thr
    1205                1210                1215

Asp Asn Gly Ser Pro Pro Lys Ser Thr Ile Ala Arg Val Ile Val
    1220                1225                1230

Lys Ile Leu Asp Glu Asn Asp Asn Lys Pro Gln Phe Leu Gln Lys
    1235                1240                1245

Phe Tyr Lys Ile Arg Leu Pro Glu Arg Glu Lys Pro Asp Arg Glu
    1250                1255                1260

Arg Asn Ala Arg Arg Glu Pro Leu Tyr His Val Ile Ala Thr Asp
    1265                1270                1275

Lys Asp Glu Gly Pro Asn Ala Glu Ile Ser Tyr Ser Ile Glu Asp
    1280                1285                1290

Gly Asn Glu His Gly Lys Phe Phe Ile Gly Pro Lys Thr Gly Val
    1295                1300                1305

Val Ser Ser Lys Arg Phe Ser Ala Ala Gly Glu Tyr Asp Ile Leu
    1310                1315                1320

Ser Ile Lys Ala Val Asp Asn Gly Arg Pro Gln Lys Ser Ser Thr
```

```
                   1325                1330                1335

Thr Arg Leu His Ile Glu Trp Ile Ser Lys Pro Lys Pro Ser Leu
    1340                1345                1350

Glu Pro Ile Ser Phe Glu Glu Ser Phe Thr Phe Thr Val Met
    1355                1360                1365

Glu Ser Asp Pro Val Ala His Met Ile Gly Val Ile Ser Val Glu
    1370                1375                1380

Pro Pro Gly Ile Pro Leu Trp Phe Asp Ile Thr Gly Gly Asn Tyr
    1385                1390                1395

Asp Ser His Phe Asp Val Asp Lys Gly Thr Gly Thr Ile Ile Val
    1400                1405                1410

Ala Lys Pro Leu Asp Ala Glu Gln Lys Ser Asn Tyr Asn Leu Thr
    1415                1420                1425

Val Glu Ala Thr Asp Gly Thr Thr Thr Ile Leu Thr Gln Val Phe
    1430                1435                1440

Ile Lys Val Ile Asp Thr Asn Asp His Arg Pro Gln Phe Ser Thr
    1445                1450                1455

Ser Lys Tyr Glu Val Val Ile Pro Glu Asp Thr Ala Pro Glu Thr
    1460                1465                1470

Glu Ile Leu Gln Ile Ser Ala Val Asp Gln Asp Glu Lys Asn Lys
    1475                1480                1485

Leu Ile Tyr Thr Leu Gln Ser Ser Arg Asp Pro Leu Ser Leu Lys
    1490                1495                1500

Lys Phe Arg Leu Asp Pro Ala Thr Gly Ser Leu Tyr Thr Ser Glu
    1505                1510                1515

Lys Leu Asp His Glu Ala Val His Gln His Thr Leu Thr Val Met
    1520                1525                1530

Val Arg Asp Gln Asp Val Pro Val Lys Arg Asn Phe Ala Arg Ile
    1535                1540                1545

Val Val Asn Val Ser Asp Thr Asn Asp His Ala Pro Trp Phe Thr
    1550                1555                1560

Ala Ser Ser Tyr Lys Gly Arg Val Tyr Glu Ser Ala Ala Val Gly
    1565                1570                1575

Ser Val Val Leu Gln Val Thr Ala Leu Asp Lys Asp Lys Gly Lys
    1580                1585                1590

Asn Ala Glu Val Leu Tyr Ser Ile Glu Ser Gly Asn Ile Gly Asn
    1595                1600                1605

Ser Phe Met Ile Asp Pro Val Leu Gly Ser Ile Lys Thr Ala Lys
    1610                1615                1620

Glu Leu Asp Arg Ser Asn Gln Ala Glu Tyr Asp Leu Met Val Lys
    1625                1630                1635

Ala Thr Asp Lys Gly Ser Pro Pro Met Ser Glu Ile Thr Ser Val
    1640                1645                1650

Arg Ile Phe Val Thr Ile Ala Asp Asn Ala Ser Pro Lys Phe Thr
    1655                1660                1665

Ser Lys Glu Tyr Ser Val Glu Leu Ser Glu Thr Val Ser Ile Gly
    1670                1675                1680

Ser Phe Val Gly Met Val Thr Ala His Ser Gln Ser Ser Val Val
    1685                1690                1695

Tyr Glu Ile Lys Asp Gly Asn Thr Gly Asp Ala Phe Asp Ile Asn
    1700                1705                1710

Pro His Ser Gly Thr Ile Ile Thr Gln Lys Ala Leu Asp Phe Glu
    1715                1720                1725
```

-continued

Thr Leu Pro Ile Tyr Thr Leu Ile Ile Gln Gly Thr Asn Met Ala
    1730            1735                1740

Gly Leu Ser Thr Asn Thr Thr Val Leu Val His Leu Gln Asp Glu
    1745            1750                1755

Asn Asp Asn Ala Pro Val Phe Met Gln Ala Glu Tyr Thr Gly Leu
    1760            1765                1770

Ile Ser Glu Ser Ala Ser Ile Asn Ser Val Val Leu Thr Asp Arg
    1775            1780                1785

Asn Val Pro Leu Val Ile Arg Ala Ala Asp Ala Asp Lys Asp Ser
    1790            1795                1800

Asn Ala Leu Leu Val Tyr His Ile Val Glu Pro Ser Val His Thr
    1805            1810                1815

Tyr Phe Ala Ile Asp Ser Ser Thr Gly Ala Ile His Thr Val Leu
    1820            1825                1830

Ser Leu Asp Tyr Glu Glu Thr Ser Ile Phe His Phe Thr Val Gln
    1835            1840                1845

Val His Asp Met Gly Thr Pro Arg Leu Phe Ala Glu Tyr Ala Ala
    1850            1855                1860

Asn Val Thr Val His Val Ile Asp Ile Asn Asp Cys Pro Pro Val
    1865            1870                1875

Phe Ala Lys Pro Leu Tyr Glu Ala Ser Leu Leu Leu Pro Thr Tyr
    1880            1885                1890

Lys Gly Val Lys Val Ile Thr Val Asn Ala Thr Asp Ala Asp Ser
    1895            1900                1905

Ser Ala Phe Ser Gln Leu Ile Tyr Ser Ile Thr Glu Gly Asn Ile
    1910            1915                1920

Gly Glu Lys Phe Ser Met Asp Tyr Lys Thr Gly Ala Leu Thr Val
    1925            1930                1935

Gln Asn Thr Thr Gln Leu Arg Ser Arg Tyr Glu Leu Thr Val Arg
    1940            1945                1950

Ala Ser Asp Gly Arg Phe Ala Gly Leu Thr Ser Val Lys Ile Asn
    1955            1960                1965

Val Lys Glu Ser Lys Glu Ser His Leu Lys Phe Thr Gln Asp Val
    1970            1975                1980

Tyr Ser Ala Val Val Lys Glu Asn Ser Thr Glu Ala Glu Thr Leu
    1985            1990                1995

Ala Val Ile Thr Ala Ile Gly Asn Pro Ile Asn Glu Pro Leu Phe
    2000            2005                2010

Tyr His Ile Leu Asn Pro Asp Arg Arg Phe Lys Ile Ser Arg Thr
    2015            2020                2025

Ser Gly Val Leu Ser Thr Thr Gly Thr Pro Phe Asp Arg Glu Gln
    2030            2035                2040

Gln Glu Ala Phe Asp Val Val Glu Val Thr Glu Glu His Lys
    2045            2050                2055

Pro Ser Ala Val Ala His Val Val Lys Val Ile Val Glu Asp
    2060            2065                2070

Gln Asn Asp Asn Ala Pro Val Phe Val Asn Leu Pro Tyr Tyr Ala
    2075            2080                2085

Val Val Lys Val Asp Thr Glu Val Gly His Val Ile Arg Tyr Val
    2090            2095                2100

Thr Ala Val Asp Arg Asp Ser Gly Arg Asn Gly Glu Val His Tyr
    2105            2110                2115

Tyr Leu Lys Glu His His Glu His Phe Gln Ile Gly Pro Leu Gly
    2120            2125                2130

```
Glu Ile Ser Leu Lys Lys Gln Phe Glu Leu Asp Thr Leu Asn Lys
2135                2140                2145

Glu Tyr Leu Val Thr Val Val Ala Lys Asp Gly Gly Asn Pro Ala
2150                2155                2160

Phe Ser Ala Glu Val Ile Val Pro Ile Thr Val Met Asn Lys Ala
2165                2170                2175

Met Pro Val Phe Glu Lys Pro Phe Tyr Ser Ala Glu Ile Ala Glu
2180                2185                2190

Ser Ile Gln Val His Ser Pro Val Val His Val Gln Ala Asn Ser
2195                2200                2205

Pro Glu Gly Leu Lys Val Phe Tyr Ser Ile Thr Asp Gly Asp Pro
2210                2215                2220

Phe Ser Gln Phe Thr Ile Asn Phe Asn Thr Gly Val Ile Asn Val
2225                2230                2235

Ile Ala Pro Leu Asp Phe Glu Ala His Pro Ala Tyr Lys Leu Ser
2240                2245                2250

Ile Arg Ala Thr Asp Ser Leu Thr Gly Ala His Ala Glu Val Phe
2255                2260                2265

Val Asp Ile Ile Val Asp Asp Ile Asn Asp Asn Pro Pro Val Phe
2270                2275                2280

Ala Gln Gln Ser Tyr Ala Val Thr Leu Ser Glu Ala Ser Val Ile
2285                2290                2295

Gly Thr Ser Val Val Gln Val Arg Ala Thr Asp Ser Asp Ser Glu
2300                2305                2310

Pro Asn Arg Gly Ile Ser Tyr Gln Met Phe Gly Asn His Ser Lys
2315                2320                2325

Ser His Asp His Phe His Val Asp Ser Ser Thr Gly Leu Ile Ser
2330                2335                2340

Leu Leu Arg Thr Leu Asp Tyr Glu Gln Ser Arg Gln His Thr Ile
2345                2350                2355

Phe Val Arg Ala Val Asp Gly Gly Met Pro Thr Leu Ser Ser Asp
2360                2365                2370

Val Ile Val Thr Val Asp Val Thr Asp Leu Asn Asp Asn Pro Pro
2375                2380                2385

Leu Phe Glu Gln Gln Ile Tyr Glu Ala Arg Ile Ser Glu His Ala
2390                2395                2400

Pro His Gly His Phe Val Thr Cys Val Lys Ala Tyr Asp Ala Asp
2405                2410                2415

Ser Ser Asp Ile Asp Lys Leu Gln Tyr Ser Ile Leu Ser Gly Asn
2420                2425                2430

Asp His Lys His Phe Val Ile Asp Ser Ala Thr Gly Ile Ile Thr
2435                2440                2445

Leu Ser Asn Leu His Arg His Ala Leu Lys Pro Phe Tyr Ser Leu
2450                2455                2460

Asn Leu Ser Val Ser Asp Gly Val Phe Arg Ser Ser Thr Gln Val
2465                2470                2475

His Val Thr Val Ile Gly Gly Asn Leu His Ser Pro Ala Phe Leu
2480                2485                2490

Gln Asn Glu Tyr Glu Val Glu Leu Ala Glu Asn Ala Pro Leu His
2495                2500                2505

Thr Leu Val Met Glu Val Lys Thr Thr Asp Gly Asp Ser Gly Ile
2510                2515                2520

Tyr Gly His Val Thr Tyr His Ile Val Asn Asp Phe Ala Lys Asp
```

```
              2525                2530                2535

Arg  Phe  Tyr  Ile  Asn  Glu  Arg  Gly  Gln  Ile  Phe  Thr  Leu  Glu  Lys
         2540                2545                2550

Leu  Asp  Arg  Glu  Thr  Pro  Ala  Glu  Lys  Val  Ile  Ser  Val  Arg  Leu
         2555                2560                2565

Met  Ala  Lys  Asp  Ala  Gly  Gly  Lys  Val  Ala  Phe  Cys  Thr  Val  Asn
         2570                2575                2580

Val  Ile  Leu  Thr  Asp  Asp  Asn  Asp  Asn  Ala  Pro  Gln  Phe  Arg  Ala
         2585                2590                2595

Thr  Lys  Tyr  Glu  Val  Asn  Ile  Gly  Ser  Ser  Ala  Ala  Lys  Gly  Thr
         2600                2605                2610

Ser  Val  Val  Lys  Val  Leu  Ala  Ser  Asp  Ala  Asp  Glu  Gly  Ser  Asn
         2615                2620                2625

Ala  Asp  Ile  Thr  Tyr  Ala  Ile  Glu  Ala  Asp  Ser  Glu  Ser  Val  Lys
         2630                2635                2640

Glu  Asn  Leu  Glu  Ile  Asn  Lys  Leu  Ser  Gly  Val  Ile  Thr  Thr  Lys
         2645                2650                2655

Glu  Ser  Leu  Ile  Gly  Leu  Glu  Asn  Glu  Phe  Phe  Thr  Phe  Phe  Val
         2660                2665                2670

Arg  Ala  Val  Asp  Asn  Gly  Ser  Pro  Ser  Lys  Glu  Ser  Val  Val  Leu
         2675                2680                2685

Val  Tyr  Val  Lys  Ile  Leu  Pro  Pro  Glu  Met  Gln  Leu  Pro  Lys  Phe
         2690                2695                2700

Ser  Glu  Pro  Phe  Tyr  Thr  Phe  Thr  Val  Ser  Glu  Asp  Val  Pro  Ile
         2705                2710                2715

Gly  Thr  Glu  Ile  Asp  Leu  Ile  Arg  Ala  Glu  His  Ser  Gly  Thr  Val
         2720                2725                2730

Leu  Tyr  Ser  Leu  Val  Lys  Gly  Asn  Thr  Pro  Glu  Ser  Asn  Arg  Asp
         2735                2740                2745

Glu  Ser  Phe  Val  Ile  Asp  Arg  Gln  Ser  Gly  Arg  Leu  Lys  Leu  Glu
         2750                2755                2760

Lys  Ser  Leu  Asp  His  Glu  Thr  Thr  Lys  Trp  Tyr  Gln  Phe  Ser  Ile
         2765                2770                2775

Leu  Ala  Arg  Cys  Thr  Gln  Asp  Asp  His  Glu  Met  Val  Ala  Ser  Val
         2780                2785                2790

Asp  Val  Ser  Ile  Gln  Val  Lys  Asp  Ala  Asn  Asp  Asn  Ser  Pro  Val
         2795                2800                2805

Phe  Glu  Ser  Ser  Pro  Tyr  Glu  Ala  Phe  Ile  Val  Glu  Asn  Leu  Pro
         2810                2815                2820

Gly  Gly  Ser  Arg  Val  Ile  Gln  Ile  Arg  Ala  Ser  Asp  Ala  Asp  Ser
         2825                2830                2835

Gly  Thr  Asn  Gly  Gln  Val  Met  Tyr  Ser  Leu  Asp  Gln  Ser  Gln  Ser
         2840                2845                2850

Val  Glu  Val  Ile  Glu  Ser  Phe  Ala  Ile  Asn  Met  Glu  Thr  Gly  Trp
         2855                2860                2865

Ile  Thr  Thr  Leu  Lys  Glu  Leu  Asp  His  Glu  Lys  Arg  Asp  Asn  Tyr
         2870                2875                2880

Gln  Ile  Lys  Val  Val  Ala  Ser  Asp  His  Gly  Glu  Lys  Ile  Gln  Leu
         2885                2890                2895

Ser  Ser  Thr  Ala  Ile  Val  Asp  Val  Thr  Val  Thr  Asp  Val  Asn  Asp
         2900                2905                2910

Ser  Pro  Pro  Arg  Phe  Thr  Ala  Glu  Ile  Tyr  Lys  Gly  Thr  Val  Ser
         2915                2920                2925
```

-continued

```
Glu Asp Asp Pro Gln Gly Gly Val Ile Ala Ile Leu Ser Thr Thr
2930                2935                2940

Asp Ala Asp Ser Glu Glu Ile Asn Arg Gln Val Thr Tyr Phe Ile
2945                2950                2955

Thr Gly Gly Asp Pro Leu Gly Gln Phe Ala Val Glu Thr Ile Gln
2960                2965                2970

Asn Glu Trp Lys Val Tyr Val Lys Lys Pro Leu Asp Arg Glu Lys
2975                2980                2985

Arg Asp Asn Tyr Leu Leu Thr Ile Thr Ala Thr Asp Gly Thr Phe
2990                2995                3000

Ser Ser Lys Ala Ile Val Glu Val Lys Val Leu Asp Ala Asn Asp
3005                3010                3015

Asn Ser Pro Val Cys Glu Lys Thr Leu Tyr Ser Asp Thr Ile Pro
3020                3025                3030

Glu Asp Val Leu Pro Gly Lys Leu Ile Met Gln Ile Ser Ala Thr
3035                3040                3045

Asp Ala Asp Ile Arg Ser Asn Ala Glu Ile Thr Tyr Thr Leu Leu
3050                3055                3060

Gly Ser Gly Ala Glu Lys Phe Lys Leu Asn Pro Asp Thr Gly Glu
3065                3070                3075

Leu Lys Thr Ser Thr Pro Leu Asp Arg Glu Glu Gln Ala Val Tyr
3080                3085                3090

His Leu Leu Val Arg Ala Thr Asp Gly Gly Gly Arg Phe Cys Gln
3095                3100                3105

Ala Ser Ile Val Leu Thr Leu Glu Asp Val Asn Asp Asn Ala Pro
3110                3115                3120

Glu Phe Ser Ala Asp Pro Tyr Ala Ile Thr Val Phe Glu Asn Thr
3125                3130                3135

Glu Pro Gly Thr Leu Leu Thr Arg Val Gln Ala Thr Asp Ala Asp
3140                3145                3150

Ala Gly Leu Asn Arg Lys Ile Leu Tyr Ser Leu Ile Asp Ser Ala
3155                3160                3165

Asp Gly Gln Phe Ser Ile Asn Glu Leu Ser Gly Ile Ile Gln Leu
3170                3175                3180

Glu Lys Pro Leu Asp Arg Glu Leu Gln Ala Val Tyr Thr Leu Ser
3185                3190                3195

Leu Lys Ala Val Asp Gln Gly Leu Pro Arg Arg Leu Thr Ala Thr
3200                3205                3210

Gly Thr Val Ile Val Ser Val Leu Asp Ile Asn Asp Asn Pro Pro
3215                3220                3225

Val Phe Glu Tyr Arg Glu Tyr Gly Ala Thr Val Ser Glu Asp Ile
3230                3235                3240

Leu Val Gly Thr Glu Val Leu Gln Val Tyr Ala Ala Ser Arg Asp
3245                3250                3255

Ile Glu Ala Asn Ala Glu Ile Thr Tyr Ser Ile Ile Ser Gly Asn
3260                3265                3270

Glu His Gly Lys Phe Ser Ile Asp Ser Lys Thr Gly Ala Val Phe
3275                3280                3285

Ile Ile Glu Asn Leu Asp Tyr Glu Ser Ser His Glu Tyr Tyr Leu
3290                3295                3300

Thr Val Glu Ala Thr Asp Gly Gly Thr Pro Ser Leu Ser Asp Val
3305                3310                3315

Ala Thr Val Asn Val Asn Val Thr Asp Ile Asn Asp Asn Thr Pro
3320                3325                3330
```

-continued

Val Phe Ser Gln Asp Thr Tyr Thr Thr Val Ile Ser Glu Asp Ala
3335                3340                3345

Val Leu Glu Gln Ser Val Ile Thr Val Met Ala Asp Asp Ala Asp
3350                3355                3360

Gly Pro Ser Asn Ser His Ile His Tyr Ser Ile Ile Asp Gly Asn
3365                3370                3375

Gln Gly Ser Ser Phe Thr Ile Asp Pro Val Arg Gly Glu Val Lys
3380                3385                3390

Val Thr Lys Leu Leu Asp Arg Glu Thr Ile Ser Gly Tyr Thr Leu
3395                3400                3405

Thr Val Gln Ala Ser Asp Asn Gly Ser Pro Pro Arg Val Asn Thr
3410                3415                3420

Thr Thr Val Asn Ile Asp Val Ser Asp Val Asn Asp Asn Ala Pro
3425                3430                3435

Val Phe Ser Arg Gly Asn Tyr Ser Val Ile Ile Gln Glu Asn Lys
3440                3445                3450

Pro Val Gly Phe Ser Val Leu Gln Leu Val Val Thr Asp Glu Asp
3455                3460                3465

Ser Ser His Asn Gly Pro Pro Phe Phe Phe Thr Ile Val Thr Gly
3470                3475                3480

Asn Asp Glu Lys Ala Phe Glu Val Asn Pro Gln Gly Val Leu Leu
3485                3490                3495

Thr Ser Ser Ala Ile Lys Arg Lys Glu Lys Asp His Tyr Leu Leu
3500                3505                3510

Gln Val Lys Val Ala Asp Asn Gly Lys Pro Gln Leu Ser Ser Leu
3515                3520                3525

Thr Tyr Ile Asp Ile Arg Val Ile Glu Glu Ser Ile Tyr Pro Pro
3530                3535                3540

Ala Ile Leu Pro Leu Glu Ile Phe Ile Thr Ser Ser Gly Glu Glu
3545                3550                3555

Tyr Ser Gly Gly Val Ile Gly Lys Ile His Ala Thr Asp Gln Asp
3560                3565                3570

Val Tyr Asp Thr Leu Thr Tyr Ser Leu Asp Pro Gln Met Asp Asn
3575                3580                3585

Leu Phe Ser Val Ser Ser Thr Gly Gly Lys Leu Ile Ala His Lys
3590                3595                3600

Lys Leu Asp Ile Gly Gln Tyr Leu Leu Asn Val Ser Val Thr Asp
3605                3610                3615

Gly Lys Phe Thr Thr Val Ala Asp Ile Thr Val His Ile Arg Gln
3620                3625                3630

Val Thr Gln Glu Met Leu Asn His Thr Ile Ala Ile Arg Phe Ala
3635                3640                3645

Asn Leu Thr Pro Glu Glu Phe Val Gly Asp Tyr Trp Arg Asn Phe
3650                3655                3660

Gln Arg Ala Leu Arg Asn Ile Leu Gly Val Arg Arg Asn Asp Ile
3665                3670                3675

Gln Ile Val Ser Leu Gln Ser Ser Glu Pro His Pro His Leu Asp
3680                3685                3690

Val Leu Leu Phe Val Glu Lys Pro Gly Ser Ala Gln Ile Ser Thr
3695                3700                3705

Lys Gln Leu Leu His Lys Ile Asn Ser Ser Val Thr Asp Ile Glu
3710                3715                3720

Glu Ile Ile Gly Val Arg Ile Leu Asn Val Phe Gln Lys Leu Cys

```
                3725                3730                3735

Ala Gly Leu Asp Cys Pro Trp Lys Phe Cys Asp Glu Lys Val Ser
        3740                3745                3750

Val Asp Glu Ser Val Met Ser Thr His Ser Thr Ala Arg Leu Ser
        3755                3760                3765

Phe Val Thr Pro Arg His His Arg Ala Ala Val Cys Leu Cys Lys
        3770                3775                3780

Glu Gly Arg Cys Pro Pro Val His His Gly Cys Glu Asp Asp Pro
        3785                3790                3795

Cys Pro Glu Gly Ser Glu Cys Val Ser Asp Pro Trp Glu Glu Lys
        3800                3805                3810

His Thr Cys Val Cys Pro Ser Gly Arg Phe Gly Gln Cys Pro Gly
        3815                3820                3825

Ser Ser Ser Met Thr Leu Thr Gly Asn Ser Tyr Val Lys Tyr Arg
        3830                3835                3840

Leu Thr Glu Asn Glu Asn Lys Leu Glu Met Lys Leu Thr Met Arg
        3845                3850                3855

Leu Arg Thr Tyr Ser Thr His Ala Val Val Met Tyr Ala Arg Gly
        3860                3865                3870

Thr Asp Tyr Ser Ile Leu Glu Ile His His Gly Arg Leu Gln Tyr
        3875                3880                3885

Lys Phe Asp Cys Gly Ser Gly Pro Gly Ile Val Ser Val Gln Ser
        3890                3895                3900

Ile Gln Val Asn Asp Gly Gln Trp His Ala Val Ala Leu Glu Val
        3905                3910                3915

Asn Gly Asn Tyr Ala Arg Leu Val Leu Asp Gln Val His Thr Ala
        3920                3925                3930

Ser Gly Thr Ala Pro Gly Thr Leu Lys Thr Leu Asn Leu Asp Asn
        3935                3940                3945

Tyr Val Phe Phe Gly Gly His Ile Arg Gln Gln Gly Thr Arg His
        3950                3955                3960

Gly Arg Ser Pro Gln Val Gly Asn Gly Phe Arg Gly Cys Met Asp
        3965                3970                3975

Ser Ile Tyr Leu Asn Gly Gln Glu Leu Pro Leu Asn Ser Lys Pro
        3980                3985                3990

Arg Ser Tyr Ala His Ile Glu Glu Ser Val Asp Val Ser Pro Gly
        3995                4000                4005

Cys Phe Leu Thr Ala Thr Glu Asp Cys Ala Ser Asn Pro Cys Gln
        4010                4015                4020

Asn Gly Gly Val Cys Asn Pro Ser Pro Ala Gly Gly Tyr Tyr Cys
        4025                4030                4035

Lys Cys Ser Ala Leu Tyr Ile Gly Thr His Cys Glu Ile Ser Val
        4040                4045                4050

Asn Pro Cys Ser Ser Lys Pro Cys Leu Tyr Gly Gly Thr Cys Val
        4055                4060                4065

Val Asp Asn Gly Gly Phe Val Cys Gln Cys Arg Gly Leu Tyr Thr
        4070                4075                4080

Gly Gln Arg Cys Gln Leu Ser Pro Tyr Cys Lys Asp Glu Pro Cys
        4085                4090                4095

Lys Asn Gly Gly Thr Cys Phe Asp Ser Leu Asp Gly Ala Val Cys
        4100                4105                4110

Gln Cys Asp Ser Gly Phe Arg Gly Glu Arg Cys Gln Ser Asp Ile
        4115                4120                4125
```

```
Asp Glu Cys Ser Gly Asn Pro Cys Leu His Gly Ala Leu Cys Glu
4130                4135                4140

Asn Thr His Gly Ser Tyr His Cys Asn Cys Ser His Glu Tyr Arg
4145                4150                4155

Gly Arg His Cys Glu Asp Ala Ala Pro Asn Gln Tyr Val Ser Thr
4160                4165                4170

Pro Trp Asn Ile Gly Leu Ala Glu Gly Ile Gly Ile Val Val Phe
4175                4180                4185

Val Ala Gly Ile Phe Leu Leu Val Val Val Phe Val Leu Cys Arg
4190                4195                4200

Lys Met Ile Ser Arg Lys Lys Lys His Gln Ala Glu Pro Lys Asp
4205                4210                4215

Lys His Leu Gly Pro Ala Thr Ala Phe Leu Gln Arg Pro Tyr Phe
4220                4225                4230

Asp Ser Lys Leu Asn Lys Asn Ile Tyr Ser Asp Ile Pro Pro Gln
4235                4240                4245

Val Pro Val Arg Pro Ile Ser Tyr Thr Pro Ser Ile Pro Ser Asp
4250                4255                4260

Ser Arg Asn Asn Leu Asp Arg Asn Ser Phe Glu Gly Ser Ala Ile
4265                4270                4275

Pro Glu His Pro Glu Phe Ser Thr Phe Asn Pro Glu Ser Val His
4280                4285                4290

Gly His Arg Lys Ala Val Ala Val Cys Ser Val Ala Pro Asn Leu
4295                4300                4305

Pro Pro Pro Pro Pro Ser Asn Ser Pro Ser Asp Ser Asp Ser Ile
4310                4315                4320

Gln Lys Pro Ser Trp Asp Phe Asp Tyr Asp Thr Lys Val Val Asp
4325                4330                4335

Leu Asp Pro Cys Leu Ser Lys Pro Leu Glu Glu Lys Pro Ser
4340                4345                4350

Gln Pro Tyr Ser Ala Arg Glu Ser Leu Ser Glu Val Gln Ser Leu
4355                4360                4365

Ser Ser Phe Gln Ser Glu Ser Cys Asp Asp Asn Gly Tyr His Trp
4370                4375                4380

Asp Thr Ser Asp Trp Met Pro Ser Val Pro Leu Pro Asp Ile Gln
4385                4390                4395

Glu Phe Pro Asn Tyr Glu Val Ile Asp Glu Gln Thr Pro Leu Tyr
4400                4405                4410

Ser Ala Asp Pro Asn Ala Ile Asp Thr Asp Tyr Tyr Pro Gly Gly
4415                4420                4425

Tyr Asp Ile Glu Ser Asp Phe Pro Pro Pro Pro Glu Asp Phe Pro
4430                4435                4440

Ala Ala Asp Glu Leu Pro Pro Leu Pro Pro Glu Phe Ser Asn Gln
4445                4450                4455

Phe Glu Ser Ile His Pro Pro Arg Asp Met Pro Ala Ala Gly Ser
4460                4465                4470

Leu Gly Ser Ser Ser Arg Asn Arg Gln Arg Phe Asn Leu Asn Gln
4475                4480                4485

Tyr Leu Pro Asn Phe Tyr Pro Leu Asp Met Ser Glu Pro Gln Thr
4490                4495                4500

Lys Gly Thr Gly Glu Asn Ser Thr Cys Arg Glu Pro His Ala Pro
4505                4510                4515

Tyr Pro Pro Gly Tyr Gln Arg His Phe Glu Ala Pro Ala Val Glu
4520                4525                4530
```

```
Ser  Met  Pro  Met  Ser  Val  Tyr  Ala  Ser  Thr  Ala  Ser  Cys  Ser  Asp
     4535                4540                     4545

Val  Ser  Ala  Cys  Cys  Glu  Val  Glu  Ser  Glu  Val  Met  Met  Ser  Asp
     4550                4555                     4560

Tyr  Glu  Ser  Gly  Asp  Asp  Gly  His  Phe  Glu  Glu  Val  Thr  Ile  Pro
     4565                4570                     4575

Pro  Leu  Asp  Ser  Gln  Gln  His  Thr  Glu  Val
     4580                4585

<210> SEQ ID NO 3
<211> LENGTH: 20
<212> TYPE: DNA
<213> ORGANISM: artificial
<220> FEATURE:
<223> OTHER INFORMATION: Rat Fat1-specific forward primer

<400> SEQUENCE: 3 cccettccaa ctctccctca                                                  20

<210> SEQ ID NO 4
<211> LENGTH: 20
<212> TYPE: DNA
<213> ORGANISM: artificial
<220> FEATURE:
<223> OTHER INFORMATION: Rat Fat1-specific reverse primer

<400> SEQUENCE: 4
caggctctcc cgggcactgt                                                  20

<210> SEQ ID NO 5
<211> LENGTH: 19
<212> TYPE: DNA
<213> ORGANISM: artificial
<220> FEATURE:
<223> OTHER INFORMATION: Mouse Fat1 siRNA template

<400> SEQUENCE: 5
ggaccgaagt caccaagta                                                   19

<210> SEQ ID NO 6
<211> LENGTH: 19
<212> TYPE: DNA
<213> ORGANISM: artificial
<220> FEATURE:
<223> OTHER INFORMATION: Mouse Fat1 siRNA template 2

<400> SEQUENCE: 6
gcgacgcatt taacattaa                                                   19

<210> SEQ ID NO 7
<211> LENGTH: 19
<212> TYPE: DNA
<213> ORGANISM: artificial
<220> FEATURE:
<223> OTHER INFORMATION: Mouse Fat1 siRNA template 3

<400> SEQUENCE: 7
gcatgacact ttaaataaa                                                   19

<210> SEQ ID NO 8
<211> LENGTH: 19
<212> TYPE: DNA
<213> ORGANISM: artificial
<220> FEATURE:
<223> OTHER INFORMATION: Mouse Fat1 siRNA template
```

```
<400> SEQUENCE: 8
gtctggcaat gatcataaa                                              19

<210> SEQ ID NO 9
<211> LENGTH: 19
<212> TYPE: DNA
<213> ORGANISM: artificial
<220> FEATURE:
<223> OTHER INFORMATION: control siRNA.  Scrambled derivative of the
      7296 sequence

<400> SEQUENCE: 9
gtaaccataa acaggcatt                                              19

<210> SEQ ID NO 10
<211> LENGTH: 19
<212> TYPE: DNA
<213> ORGANISM: artificial
<220> FEATURE:
<223> OTHER INFORMATION: control siRNA.  Mismatched derivative of the
      7296 sequence.

<400> SEQUENCE: 10
gtctgataat gcgcataaa                                              19

<210> SEQ ID NO 11
<211> LENGTH: 30
<212> TYPE: DNA
<213> ORGANISM: artificial
<220> FEATURE:
<223> OTHER INFORMATION: Mouse Fat1IC RT-PCR forward primer

<400> SEQUENCE: 11
aagcttctct gccggaagat gatcagtcgg                                  30

<210> SEQ ID NO 12
<211> LENGTH: 27
<212> TYPE: DNA
<213> ORGANISM: artificial
<220> FEATURE:
<223> OTHER INFORMATION: Mouse Fat1IC RT-PCR reverse primer

<400> SEQUENCE: 12
tctagacact tccgtatgct gctggga                                     27

<210> SEQ ID NO 13
<211> LENGTH: 29
<212> TYPE: DNA
<213> ORGANISM: artificial
<220> FEATURE:
<223> OTHER INFORMATION: forward primer for generating Fat 4189-4587

<400> SEQUENCE: 13
ccatgggcct ctgccggaag atgatcagt                                   29

<210> SEQ ID NO 14
<211> LENGTH: 30
<212> TYPE: DNA
<213> ORGANISM: artificial
<220> FEATURE:
<223> OTHER INFORMATION: forward primer for generating  Fat14201-4587

<400> SEQUENCE: 14
ccatgggcca ggctgaacct gaagacaaac                                  30
```

US 8,586,534 B2

INTRACELLULAR DOMAIN OF A MAMMALIAN FAT1 (FAT1IC)

CROSS REFERENCE TO RELATED APPLICATION

This application claims the benefit of U.S. Provisional Application No. 60/928,216, filed May 8, 2007, the contents of which are hereby incorporated by reference in its entirety.

STATEMENT REGARDING FEDERALLY SPONSORED RESEARCH OR DEVELOPMENT

The invention was made with government support under grant number R01 HL67944-01 awarded by the National Institutes of Health. The government has certain rights in the invention.

BACKGROUND OF THE INVENTION (1) Field of the Invention

The present invention generally relates to compositions and treatments for vascular disorders. More specifically, the invention provides compositions comprising Fat1 or isolated domains thereof, and methods of using these and other compositions with methods of vascular repair such as angioplasty and coronary bypass surgery.

(2) Description of the Related Art

Vascular remodeling is a critical part of the pathogenesis of clinically important vascular disorders such as atherosclerosis, restenosis after angioplasty, and saphenous vein graft disease (Shanahan and Weissberg, 1998; Owens et al., 2004). Despite considerable study, the molecular mechanisms that control vascular smooth muscle cell (VSMC) activities during vascular remodeling are not fully understood. Recent reports linking cadherins to VSMC regulation (Jones et al., 2002; Slater et al., 2004; Uglow et al., 2003) suggest that these transmembrane adhesion proteins, characterized extensively as major mediators of epithelial cell homeostasis, may also be important in vascular remodeling.

Cadherins are involved in $Ca^{2+}$-dependent cell-cell adhesion, intracellular junction assembly, and tissue morphogenesis during development (Yap et al., 1997; Angst et al., 2001; Wheelock and Johnson, 2003b). Major subdivisions of the large cadherin superfamily include the classical cadherins and the protocadherins (Gallin, 1998; Yagi and Takeichi, 2000; Angst et al., 2001). The extracellular domains of these proteins share a unique structure, the cadherin motif, which is repeated in tandem in variable numbers. Classical cadherins function as homophilic adhesive molecules, and both extracellular and cytoplasmic domains contribute to this function. Classical cadherin cytoplasmic domains interact with β-catenin and plakoglobin (Huber and Weis, 2001; Takeichi, 1995), members of the armadillo gene family of transcription factors. This interaction effectively sequesters β-catenin away from the nucleus, limits its transcriptional activity (Sadot et al., 1998; Kaplan et al., 2001; Simcha et al., 2001), and thus links cadherins to the canonical Wnt signaling pathway, a major determinant of cellular activity during development (Bhanot et al., 1999; Jamora et al., 2003; Nelson and Nusse, 2004).

Like classical cadherins, protocadherins have extracellular domains capable of $Ca^{2+}$-dependent, homophilic interaction (Suzuki, 2000). Protocadherin cytoplasmic domains, on the other hand, are structurally divergent from those of the classical cadherins, and less is known about their function. Sequestration and inhibition of β-catenin by protocadherins has not been described.

Although mammalian Fat1 genes (Dunne et al., 1995; Ponassi et al., 1999; Cox et al., 2000) were initially characterized as homologues of the *Drosophila* protein Fat (Mahoney et al., 1991), recent bioinformatics analysis indicates that Fat1 is more closely related to *Drosophila* Fat-like (Ftl) (Castillejo-Lopez et al., 2004). In *Drosophila*, Ftl is expressed apically in luminal tissues such as trachea, salivary glands, proventriculus, and hindgut (Castillejo-Lopez et al., 2004). Silencing of ftl results in the collapse of tracheal epithelia, and it has been suggested that Ftl is required for morphogenesis and maintenance of tubular structures of ectodermal origin.

Like *Drosophila* Fat and Ftl, mammalian Fat1 is remarkable for its very large size (~4600 aa). It has a huge extracellular domain that contains 34 cadherin repeats, 5 EGF-like repeats, and 1 laminin A-G motif, a single transmembrane region, and a cytoplasmic tail of ~400 aa (Dunne et al., 1995). Sequences within the Fat1 cytoplasmic domain ($Fat1_{IC}$) show limited similarity to β-catenin binding regions of classical cadherins (Dunne et al., 1995).

SUMMARY OF THE INVENTION

The inventors have discovered that Fat1 regulates growth and migration of vascular smooth muscle cells (VSMCs).

The invention is directed to an extracellular domain of a mammalian Fat1 ($Fat1_{EC}$), the extracellular domain comprising amino acids equivalent to amino acids 22-4174 of a wild-type mouse Fat1 having the amino acid sequence of SEQ ID NO:1, where the extracellular domain does not comprise the entire mammalian Fat1.

The invention is also directed to an intracellular domain of a mammalian Fat1 ($Fat1_{IC}$), the intracellular domain comprising amino acids equivalent to amino acids 4199-4598 of a wild-type mouse Fat1 having the amino acid sequence of SEQ ID NO:1, where the extracellular domain does not comprise the entire mammalian Fat1.

The invention is additionally directed to a vector comprising a nucleic acid sequence encoding the above-described $Fat1_{EC}$, wherein the vector is capable of expressing the $Fat1_{EC}$ in a mammalian cell.

Additionally, the invention is directed to a vector comprising a nucleic acid sequence encoding the above-described $Fat1_{IC}$, wherein the vector is capable of expressing the $Fat1_{IC}$ in a mammalian cell.

The invention is further directed to a vascular stent coated with the above-described $Fat1_{EC}$.

Also, the invention is directed to vascular stents coated with a Fat1 ligand that activates Fat1.

Further, the invention is directed to a method of treating a patient at risk for restenosis of a blood vessel, the method comprising inserting the above-described vascular stent into the blood vessel at the site of the risk.

The invention is also directed to a method of treating an injured blood vessel in a patient. The method comprises administering the above-described $Fat1_{IC}$ or the above-described $Fat1_{IC}$ vector to the injured blood vessel in a manner sufficient to treat the injured blood vessel.

The invention is additionally directed to a method of treating a patient at risk for restenosis of a blood vessel or having an injured blood vessel. The method comprises administering to the patient a vector encoding a Fat1 having an amino acid sequence at least 90% identical to SEQ ID NO:1 or SEQ ID NO:2, where the vector is capable of expressing the Fat1 in cells of the patient, and wherein the Fat1 is capable of inhibiting growth and promoting migration of vascular smooth muscle cells (VSMC).

The invention is further directed to a method of treating an injured blood vessel in a patient. The method comprises administering a compound to the injured blood vessel, where the compound specifically binds to Fat1 and prevents the ability of the Fat1 to promote migration of vascular smooth muscle cells (VSMC).

DETAILED DESCRIPTION OF THE INVENTION

Figure 1:
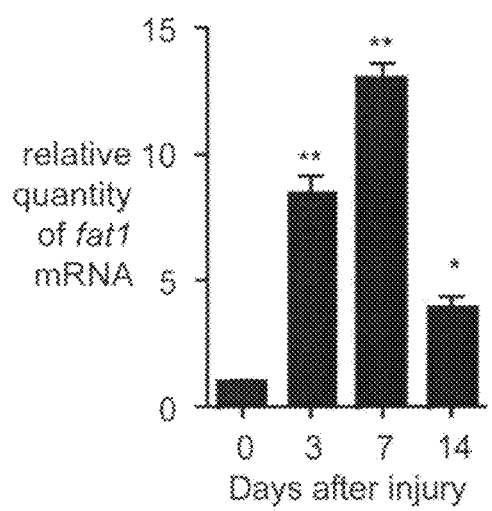
FIG. 1 is a graph, a photograph of a western blot, and micrographs of stained tissue sections showing expression of Fat1 in normal and balloon-injured rat carotid arteries. Panel B shows results of a qPCR analysis of fat1 mRNA expression. Fat1 mRNA levels were corrected relative to gapdh mRNA levels, with day 0 (no injury) set=1. *, $P<0.05$, **, $P<0.01$ vs. day 0. Panel B shows the specificity of anti-Fat1 antiserum. Preimmune and anti-Fat1 immune rabbit sera (1:5000 dilutions) were tested by immunoblotting of replicate total RASMC protein extracts (20 μg/lane). The arrow indicates the Fat1 signal. Panel C shows an immunohistochemical analysis of Fat1 expression in arteries 0, 3, 7, and 14 days after injury, as indicated. Arrowheads indicate the internal elastic lamina, and double-ended arrows, the extent of the media. The neointima is the space between arrowhead and arrow. The orientation of all samples is similar, with an asterisk in the day 0 panel indicating the vessel lumen. The upper right panel shows a day 7 sample co-stained for Fat1 and PCNA; areas of increased Fat1 (arrow) and increased PCNA (arrowhead) staining are indicated. The lower right panel shows a day 7 sample in which Fat1 antiserum was omitted (no 1° ab). Scale bar, 100 μm.
Figure 1:
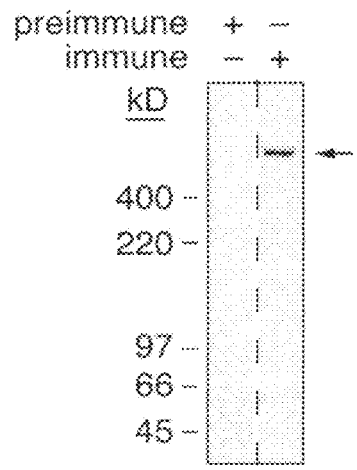
Figure 1:
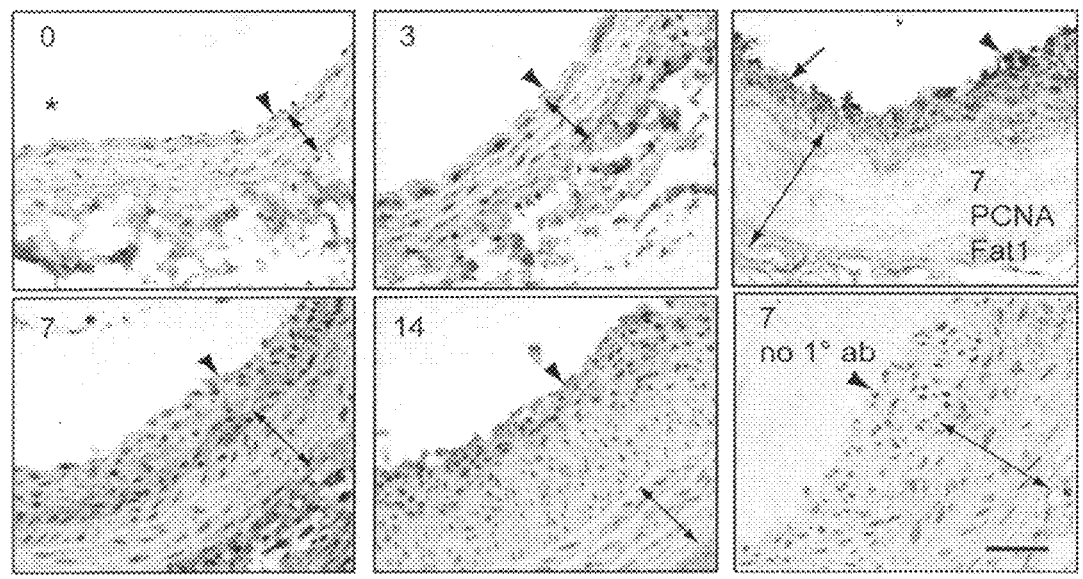

The inventors have discovered that Fat1 regulates growth and migration of vascular smooth muscle cells (VSMCs). See Example. In particular, it was discovered that the complete Fat1 protein inhibits proliferation (i.e., growth) and promotes migration of VSMCs and the intracellular domain (i.e., cytoplasmic fragment) of Fat1 inhibits both proliferation and migration of VSMCs. These discoveries make useful various invention compositions and enable various therapeutic methods.

The invention is directed to an extracellular domain of a mammalian Fat1 (Fat1$_{EC}$), the extracellular domain comprising amino acids equivalent to amino acids 22-4174 of a wild-type mouse Fat1 having the amino acid sequence of SEQ ID NO:1, where the extracellular domain does not comprise the entire mammalian Fat1.

As used herein, a Fat1 is FAT tumor suppressor homolog 1 (Drosophila) having UniProtKB/TrEMBL entry Q9QXA3. The mouse Fat1 wild-type amino acid sequence is provided herein as SEQ ID NO:1 and the mouse wild-type Fat1 mRNA sequence is provided in Genbank accession no. NM_00_001081286. The human wild-type Fat1 amino acid sequence is provided herein as SEQ ID NO:2 and the human wild-type Fat1 in RNA sequence is provided in Genbank accession no. NM_005245.3. It is expected that any other wild-type mammalian Fat1 amino acid sequence could be determined by the skilled artisan. Such an amino acid sequence would be expected to be at least 85% identical to SEQ ID NO:1 and/or SEQ ID NO:2.

The Fat1 protein is made up of a signal peptide consisting of residues 1-21 of both SEQ ID NO:1 and SEQ ID NO:2; an extracellular domain consisting of resides 22-4174 of SEQ ID NO: 1 and 22-4181 of SEQ ID NO:2; a transmembrane domain consisting of residues 4175-4198 of SEQ ID NO:1 and 4182-4201 of SEQ ID NO:2; and an intracellular domain consisting of residues 4199-4598 of SEQ ID NO:1 and 4202-4588 of SEQ ID NO:2.

The Fat1 or fragments thereof claimed herein or used in the methods claimed herein includes mutants comprising amino acid deletions, substitutions or additions, provided the mutant inhibits proliferation (i.e., growth) and promotes migration of VSMCs and the intracellular domain (i.e., cytoplasmic fragment) of the mutant inhibits both proliferation and migration of VSMCs. Methods for determining these characteristics are provided, e.g., in the Example.

The invention Fat1$_{EC}$ can further comprise other amino acids or other compounds. Examples of additional amino acids includes the signal sequence, or a portion of the transmembrane domain. Examples of another compound that can usefully be bound to the invention Fat1$_{EC}$ is a fluorescent dye.

The invention Fat1$_{EC}$ is preferably a mouse Fat1 having an amino acid sequence at least 95% identical to SEQ ID NO:1. More preferably, the invention Fat1$_{EC}$ is a human Fat1 having an amino acid sequence at least 95% identical to SEQ ID NO:2. Most preferably, the invention Fat1$_{EC}$ is capable of inhibiting growth and promoting migration of vascular smooth muscle cells (VSMC).

When used for therapeutic purposes, the invention Fat1$_{EC}$ is preferably in a pharmaceutically acceptable carrier.

By "pharmaceutically acceptable" it is meant a material that (i) is compatible with the other ingredients of the composition without rendering the composition unsuitable for its intended purpose, and (ii) is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable carriers include, without limitation, any of the standard pharmaceutical carriers such as phosphate buffered saline solutions, water, emulsions such as oil/water emulsions, microemulsions, and the like.

The above-described mutant Fat1$_{EC}$ can be formulated without undue experimentation for administration to a mammal, including humans, as appropriate for the particular application. Additionally, proper dosages of the compositions can be determined without undue experimentation using standard dose-response protocols.

Although the Fat1$_{EC}$ can be easily formulated for oral, lingual, sublingual, buccal, intrabuccal, rectal, or nasal administration, it is preferred that they be formulated for parenteral administration, such as for example, by intravenous, intramuscular, intrathecal or subcutaneous injection, since that is the most preferred route of administration of these proteins. Parenteral administration can be accomplished by incorporating the compounds into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

The invention is also directed to an intracellular domain of a mammalian Fat1 ($Fat1_{IC}$), the intracellular domain comprising amino acids equivalent to amino acids 4199-4598 of a wild-type mouse Fat1 having the amino acid sequence of SEQ ID NO:1, where the extracellular domain does not comprise the entire mammalian Fat1.

Preferably, the invention $Fat1_{IC}$ is a mouse Fat1 having an amino acid sequence at least 95% identical to SEQ ID NO:1. More preferably, the Fat1 is a human Fat1 having an amino acid sequence at least 95% identical to SEQ ID NO:2. Most preferably, the $Fat1_{IC}$ is capable of inhibiting both growth and migration of vascular smooth muscle cells (VSMC).

The $Fat1_{IC}$ here can further usefully be fused to an amino acid sequence to make a fusion protein capable of localizing the $Fat1_{IC}$ to a cell membrane. See Example. Preferably, the fusion amino acid sequence is a transmembrane region of an interleukin 2 receptor α-chain.

When used for therapeutic purposes, the invention $Fat1_{EC}$ is preferably in a pharmaceutically acceptable carrier, as described above.

The above-described invention $Fat1_{EC}$ and $Fat1_{IC}$ can also be provided as a vector for transfection of mammalian cells. Thus, the invention is additionally directed to a vector comprising a nucleic acid sequence encoding the above-described $Fat1_{EC}$, where the vector is capable of expressing the $Fat1_{EC}$ in a mammalian cell.

Also, the invention is directed to a vector comprising a nucleic acid sequence encoding the above-described $Fat1_{IC}$, wherein the vector is capable of expressing the $Fat1_{IC}$ in a mammalian cell.

The above $Fat1_{EC}$ can be applied to a vascular stent. Such a stent is useful for therapeutic applications (further discussed below). The ability to inhibit growth of VSMCs but not endothelial cells is useful for insertion into a blood vessel or vein where there is a risk for restenosis, since having an intact endothelium reduces the risk for thrombosis when compared to the common drug-eluting stents, which also inhibit endothelial cells. Thus, the invention is further directed to a vascular stent coated with the above-described $Fat1_{EC}$ that is capable of inhibiting growth and promoting migration of VSMC.

The benefits of the $Fat_{EC}$-coated stents discussed immediately above can also be achieved by instead coating the stent with a Fat1 ligand that activates Fat1. Thus, the invention is also directed to vascular stents coated with a Fat1 ligand that activates Fat1. The Fat1-activating ligand can be identified by, e.g., screening a library of compounds for the ability to activate Fat1. Preferably the library comprises antibodies (e.g., monoclonal antibodies or phage display antibodies). A preferred Fat1 ligand is an antibody, e.g., identified by that screening procedure.

The above compositions are particularly useful in methods of treating patients that have undergone angioplasty, bypass surgery or other similar procedures. In one aspect of therapeutic methods, the invention is directed to a method of treating a patient at risk for restenosis of a blood vessel, the method comprising inserting the above-described vascular stent coated with the $Fat1_{EC}$ into the blood vessel at the site of the risk. Preferably here, the blood vessel is an artery, most preferably a coronary artery.

The invention is also directed to a method of treating an injured blood vessel in a patient. The method comprises administering the above-described $Fat1_{IC}$ or the above-described $Fat1_{IC}$ vector to the injured blood vessel in a manner sufficient to treat the injured blood vessel. Where the vector is used, it is administered such that it can transfect VSMC cells in the blood vessel. In these methods, the administered $Fat1_{IC}$, or the $Fat1_{IC}$ synthesized from the vector, is useful in preventing restenosis due to the ability of the $Fat1_{IC}$ to inhibit VSMC proliferation. Optionally, the $Fat1_{IC}$ can further comprise the above-described amino acid sequence that targets the $Fat1_{IC}$ to the cell membrane. Preferably, the blood vessel is an artery or vein used in a coronary artery bypass surgery.

The invention is additionally directed to a method of treating a patient at risk for restenosis of a blood vessel or having an injured blood vessel. The method comprises administering to the patient a vector encoding a Fat1 having an amino acid sequence at least 90% identical to SEQ ID NO:1 or SEQ ID NO:2, where the vector is capable of expressing the Fat1 in cells of the patient, and wherein the Fat1 is capable of inhibiting growth and promoting migration of vascular smooth muscle cells (VSMC). The Fat1 expressed from the vector would inhibit growth and facilitate migration of VSMCs. Preferably here the Fat1 is a human Fat1 having an amino acid sequence at least 95% identical to SEQ ID NO:2. More preferably, the Fat1 is a human Fat1 having an amino acid sequence at least 99% identical to SEQ ID NO:2. The vector is also preferably administered to the patient during or after coronary artery bypass surgery. Alternatively, the vector is administered to the patient during or after angioplasty.

The invention is further directed to a method of treating an injured blood vessel in a patient. The method comprises administering a compound to the injured blood vessel, where the compound specifically binds to Fat1 and prevents the ability of the Fat1 to promote migration of vascular smooth muscle cells (VSMC). Such an application is useful to limit migration and oppose VSMC accumulation in arterial neointima.

In some aspects of these methods, the compound comprises an antibody binding site. Preferably, the compound is an antibody that has previously been shown to inhibit Fat1 activity. Such antibodies can be prepared without undue experimentation. Alternatively, the compound is an aptamer. These methods are most preferably used where the blood vessel is an artery or vein used in a coronary artery bypass surgery.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

Example

The Fat1 cadherin integrates vascular smooth muscle cell growth and migration signals.

Example Summary

This Example is based on the publication Hou et al., 2006.

The significance of cadherin superfamily proteins in vascular smooth muscle cell (VSMC) biology is undefined. Described here are recent studies of the Fat1 protocadherin. Fat1 expression in VSMCs increases significantly after arterial injury or growth factor stimulation. Fat1 knockdown decreases VSMC migration in vitro, but surprisingly, enhances cyclin D1 expression and proliferation. Despite limited similarity to classical cadherins, the Fat1 cytoplasmic domain (Fat1$_{IC}$) interacts with β-catenin, inhibiting both its nuclear localization and transcriptional activity. Fat1 undergoes cleavage and Fat1$_{IC}$ species localize to the nucleus; however, inhibition of the cyclin D1 promoter by truncated Fat1$_{IC}$ proteins corresponds to their presence outside the nucleus, which argues against repression of β-catenin-dependent transcription by nuclear Fat1$_{IC}$. These findings extend recent observations about Fat1 and migration in other cell types, and demonstrate for the first time its anti-proliferative activity and interaction with O-catenin. Because it is induced after arterial injury, Fat1 may control VSMC functions central to vascular remodeling by facilitating migration and limiting proliferation.

Introduction

These studies show that Fat1 expression increases after injury of the rat carotid artery, and is positively regulated in cultured VSMCs by several factors that promote cell proliferation and migration. Interestingly, knockdown of Fat1 expression limits VSMC migration, but enhances VSMC growth. This anti-proliferative effect of Fat1 appears to be mediated by Fat1$_{IC}$ sequences, since expression of a fusion protein containing the Fat1$_{IC}$ inhibits cyclin D1 expression and cell growth. Moreover, the Fat1$_{IC}$ can interact with O-catenin, prevent its nuclear translocation, and limit its transcriptional activity on both synthetic and native β-catenin-responsive promoters, including that of cyclin D1, a known target of canonical Wnt signaling. These findings point to an integrative role for Fat1 in regulation of critical VSMC activities, in which it promotes migration and limits both canonical Wnt signaling and VSMC growth in the remodeling artery.

Results

Expression of Fat1 Increases after Arterial Injury.

fat1 mRNA expression was quantified by quantitative PCR (qPCR) of cDNA samples from normal and injured rat carotid arteries. Compared to uninjured arteries, fat1 mRNA expression was ~8.5-, 13.0-, and 3.9-fold higher than control at 3, 7, and 14 days after injury, respectively (FIG. 1A).

Figure 3:
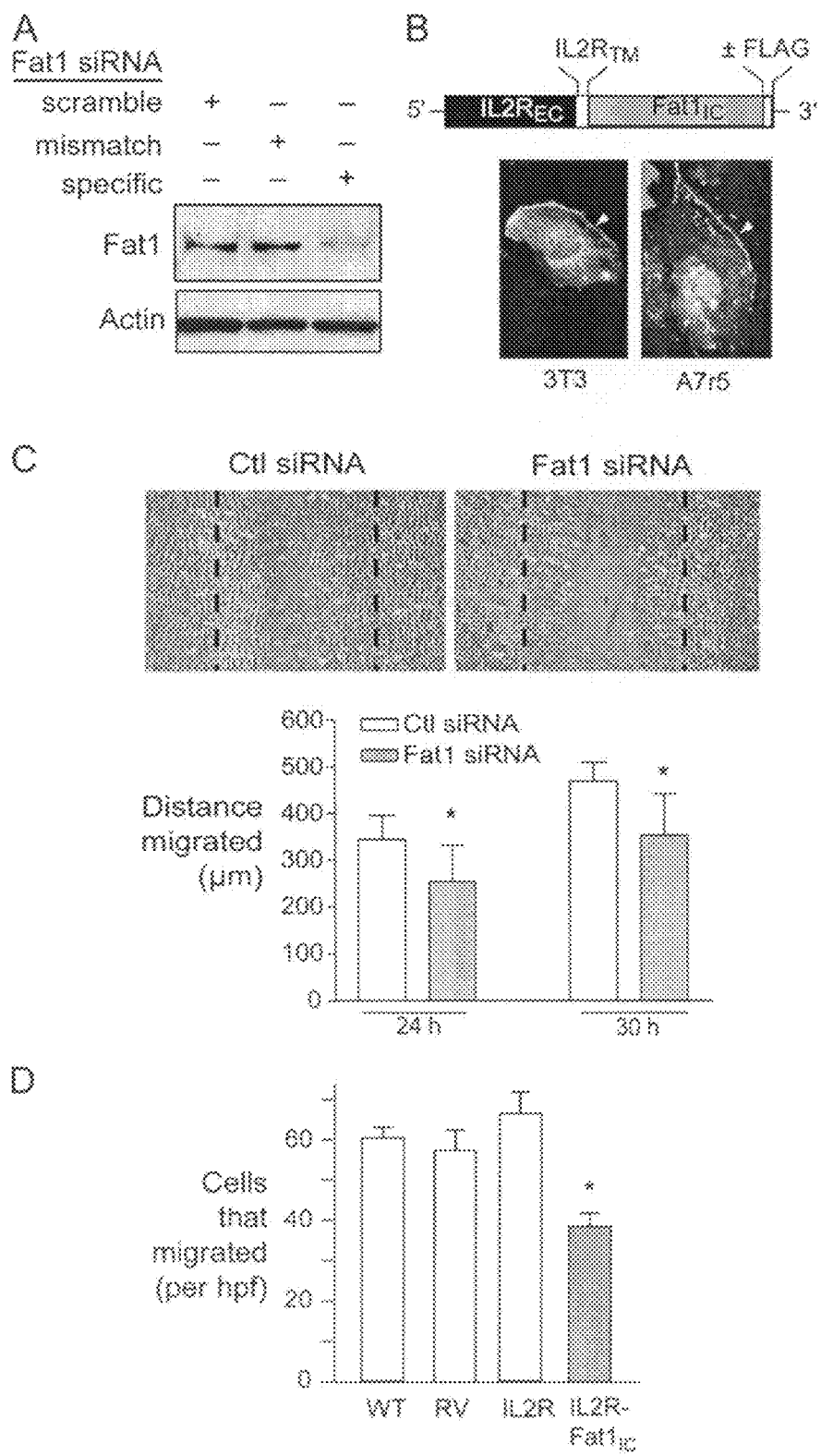
FIG. 3 is photographs of western blots, fluorescent and light micrographs of cells, and graphs showing the effect of decreased Fat1 expression on VSMC migration. Panel A shows a western analysis of Fat1 specific and control siRNA efficacy, 48 h after transfection. Panel B shows a schematic diagram of IL2R-Fat1$_{IC}$. EC, extracellular; TM, transmembrane; IC, intracellular, with photomicrograph of subcellular localization of IL2R-Fat1$_{IC}$-3XFLAG in transfected cells stained with FITC-conjugated anti-FLAG antibody. Panel C shows MASMC migration 30 h after wounding of monolayer. Dashed lines indicate extent of initial denudation. The graphs shows quantitative analysis of MASMC migration after control (Ctl) and specific Fat1 siRNA transfection. For 10 matched fields, the area of the wounded monolayer covered by cells at the indicated timepoints was determined by planimetry using NIH Image, and distance migrated calculated according to the difference from time 0. *, $P<0.05$ vs. Ctl siRNA. Panel D shows results of a transwell migration assay of A7r5 cells transduced with the indicated retroviruses. Six fields were counted per condition, and the values were averaged for each filter. *, $P<0.05$ vs. other groups.
Figure 4:
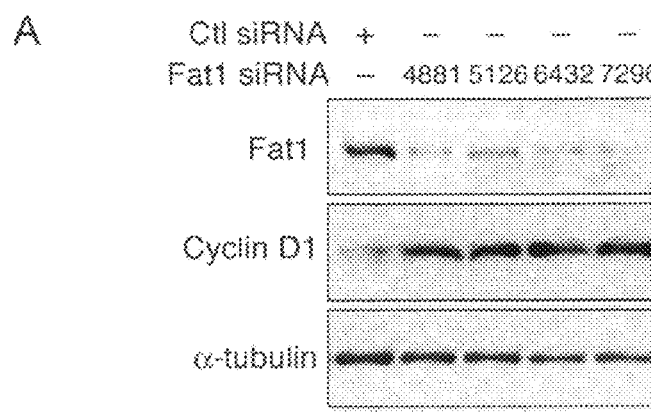
FIG. 4 is photographs of western blots and a graph showing the effect of decreased Fat1 expression on VSMC cell cycle progression. Panels A and B show a western analyses of Fat1 and cyclin D1 expression with control (Ctl) or Fat1-specific siRNAs. Panel A shows results when four distinct Fat1-specific siRNAs were transfected 48 h prior to protein extraction. Loading reference, α-tubulin. Panel B shows the efficacy of Ctl or Fat1-specific siRNA 7296 over time. Actin and O-catenin expression were also tested. Panel C shows the effect of Fat1 inhibition on DNA synthesis assessed by BrdU incorporation. Cells were transfected with Ctl or Fat1 siRNA, serum-deprived for 48 h, and stimulated with 10% FBS. BrdU incorporation was assessed as described in Materials and Methods. The graph depicts the means±S.E. of three independent experiments in which a total of 219-874 cells were counted each time for each group. *, $P<0.05$ vs. Ctl siRNA.
Figure 4:
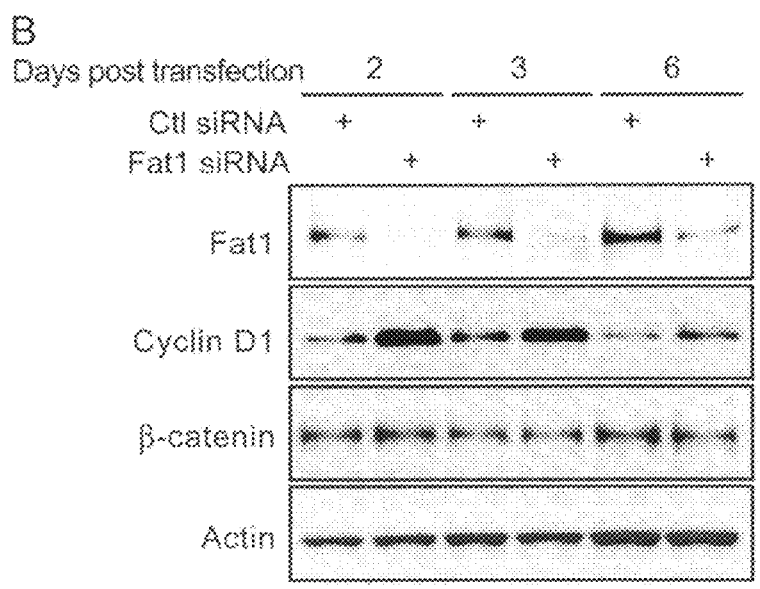
Figure 4:
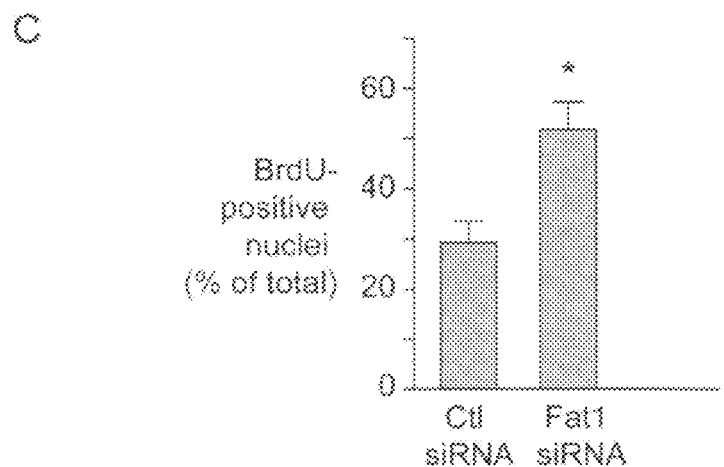

To localize Fat1 protein expression in injured arteries, we characterized rabbit antisera raised against a GST-Fat1$_{IC}$ immunogen. Immunoblotting of VSMC lysates with one such antiserum, but not preimmune serum, yielded a single high molecular weight band of ~500 kD, in accord with the predicted size of full length Fat1 (FIG. 1B). Further specificity was demonstrated in RNA interference experiments directed against multiple separate targets in the mouse Fat1 sequence (FIGS. 3 and 4). The antiserum was then used for immunohistochemical studies. As shown in FIG. 1C, prominent Fat1 staining appeared in the media 3 days after injury, while at 7 days and 14 days after injury, Fat1 staining was less evident in the media, but clearly present in the developing neoinitima.

Western analysis of Fat1 expression in the carotid artery injury model, like our qPCR findings, showed a clear induction after injury (data not shown). To correlate Fat1 expression with the proliferative status of specific cells, we co-stained sections for Fat1 and the proliferation marker PCNA. While some cells appeared positive for both, we also noted some spatial separation of the signals, particularly evident in areas with limited neointimal formation, which showed prominent Fat1 staining without PCNA (FIG. 1C, upper right). The latter observation raised the possibility that, despite its overall induction after injury, increased Fat1 expression might have negative effects on VSMC growth in vivo (FIG. 1C, upper right).

Serum and Growth Factors Induce Fat1 Expression in VSMCs.

To identify factors that might contribute to Fat1 induction after arterial injury, its expression was characterized in primary cultured VSMCs. Quiescent rat aortic smooth muscle cells (RASMCs) (time 0 h) were treated with 10% FBS for 2, 6, 12, 18, 24, and 36 h, and the level of Fat1 protein was determined by Western analysis. The Fat1 signal increased strongly between 2 and 12 h and remained elevated through 36 h (FIG. 2A). To assess cell cycle status, we also checked cyclin D1 expression in these lysates. Interestingly, Fat1 induction preceded the increase of cyclin D1, a mediator of progression through the G1 phase of the cell cycle (FIG. 2A).

We then assessed Fat1 expression in response to several factors known to affect the vascular response to injury. Western analyses showed that expression of Fat1 increased in response to Angiotensin II (ATII), basic FGF (bFGF), and PDGF-BB (FIG. 2B). Increased Fat1 expression was apparent by 2 h and sustained at high levels from 12 to 36 h after stimulation with each of these factors. Thus, Fat1 expression is regulated consistently and strongly by multiple factors known to promote VSMC growth and migration.

Inhibition of Fat1 Expression Limits VSMC Migration.

Two recent studies have described a role for Fat1 in regulation of epithelial cytoskeletal actin dynamics, planar polarity, and migration, mediated through interactions of the Fat1 cytoplasmic domain with proteins of the Ena/VASP family (Moeller et al., 2004; Tanoue and Takeichi, 2004). Fat1 induction by known VSMC chemotactic factors (FIG. 2) suggested that Fat1 might also be involved in VSMC migration. To test this and other potential Fat1 functions, we developed reagents to effectively manipulate Fat1 expression. Transfection of mouse aortic smooth muscle cells (MASMCs) with Fat1 specific small interfering RNAs (siRNAs), but not scrambled or mismatch derivatives, resulted in significantly decreased levels of Fat1 protein (FIG. 3A). To isolate and augment signals mediated by the Fat1$_{IC}$, we generated a cDNA construct, IL2R-Fat1$_{IC}$, in which the entire Fat1 cytoplasmic domain was fused to the extracellular domain and transmembrane region of the interleukin 2 receptor x-chain (IL2R), with or without a C-terminal FLAG epitope tag (FIG. 3B). Subcellular localization of this fusion protein was tested in 3T3 cells, which do not express detectable Fat1, and A7r5 VSMCs, which express moderate amounts of endogenous Fat1; both transfected 3T3 and A7r5 cells showed an appropriate cell surface signal when stained with anti-FLAG epitope antibody (FIG. 3B and data not shown). Cell migration in monolayers treated with specific Fat1 siRNA was modestly but significantly decreased compared with control siRNA (FIG. 3C), which indicates that Fat1 expression is required for optimal VSMC migration. Surprisingly, we also found decreased migration of VSMCs expressing the IL2R-Fat1$_{IC}$ protein in a Transwell assay using FBS as a stimulant in the lower chamber (FIG. 3D). Both expression of Ena/VASP proteins in VSMCs, and the ability of the IL2R-Fat1$_{IC}$ protein to interact with these signaling intermediates was confirmed (data not shown). It is surmised that although the IL2R-Fat1$_{IC}$ construct may increase intracellular Fat1 signaling, it also dissociates Fat1 extracellular interactions from this intracellular signaling, and thus interferes with directional migration. Altogether, these findings indicate that Fat1 promotes VSMC migration; it is likely that, as described in epithelial cells, interactions with Ena/VASP proteins link Fat1 expression to VSMC cytoskeletal actin reorganization, polarization, and migration.

Inhibition of Fat1 Expression Promotes VSMC Growth.

In addition to increased migration, the VSMC response to injury is characterized by cell cycle entry and increased proliferation (Clowes et al., 1983a). To evaluate how Fat1 induction after injury might affect VSMC growth, the effect of Fat1 knockdown on expression of cyclin D1 (a marker of cell cycle activation) was tested. Four distinct mouse Fat1 siRNA duplexes attenuated endogenous Fat1 levels in MASMCs; with each duplex, a significant increase in cyclin D1 expression over control levels was also observed (FIG. 4A and data not shown). The similarity of effect achieved by multiple distinct siRNAs argues strongly that increased cyclin D1 expression results from decreased Fat1, and not an off-target effect. The duration of Fat1 inhibition was more than 90% at 2 and 3 days after transfection, with persistent and strong inhibition still apparent after 6 days (FIG. 4B). Decreased Fat1 expression corresponded to increased cyclin D1 signal at each time point (2.0-2.5-fold increase of cyclin D1/actin ratio vs. control), suggesting that endogenous Fat1 exerts a tonic inhibitory effect on cyclin D1 expression (FIG. 4B). The level of total β-catenin in these cells, by contrast, showed little change.

The effect of Fat1 knockdown on DNA synthesis was also examined. Cells were transfected with Fat1 or control siRNA, and then serum deprived for 48 h prior to stimulation with 10% FBS and evaluation of BrdU incorporation. In Fat1 knockdown cultures, the fraction of BrdU positive cells was significantly higher than in control siRNA cells (52±7% vs. 30±8%, P<0.05) (FIG. 4C). These findings indicate that decreased Fat1 expression promotes cell cycle progression and DNA synthesis in VSMCs.

The Fat1$_{IC}$ is Sufficient to Inhibit VSMC Growth.

Classical cadherins interact with intracellular signaling pathways through their cytoplasmic domains (Wheelock and Johnson, 2003a). To establish cell populations differing primarily in their expression of the Fat1$_{IC}$, the IL2R (without cytoplasmic domain) and IL2R-Fat1$_{IC}$ constructs were transferred into the GFP-RV retroviral vector (Ranganath et al., 1998). Viral supernatants were produced and used to transduce A7r5 and primary MASMCs. Additional control cells, denoted RV, were produced using the unmodified GFP-RV vector. Western analysis confirmed IL2R-Fat1$_{IC}$ expression in A7r5 and MASMCs (FIG. 5A). Interestingly, endogenous cyclin D1 levels were lower in both A7r5 and MASMCs expressing IL2R-Fat1$_{IC}$ (FIG. 5A). In cell growth assays over 7 days, A7r5 cells expressing IL2R showed no significant change from control RV cells, but decreased cell numbers were evident in the IL2R-Fat1$_{IC}$ at all timepoints after 3 days (FIG. 5B). In addition, both A7r5 and MASMCs expressing the IL2R-Fat1$_{IC}$ construct showed significantly lower fractions of BrdU-positive nuclei, indicating that this decrease in cell number reflected growth inhibition rather than decreased survival (FIG. 5C). Fat1 and β-Catenin co-localize and interact in VSMCs. In epithelial cells, classical cadherins such as E-cadherin regulate Wnt signaling activity by physically associating with β-catenin at points of cell-cell contact (Nathke et al., 1994). The sequences, interacting proteins, and functions of protocadherin cytoplasmic domains are typically thought to be divergent from those of the classical cadherins (Yagi and Takeichi, 2000), and Fat1 is not regarded as part of the classical cadherin system (Tanoue and Takeichi, 2005). Nevertheless, we found that the Fat1$_{IC}$ has growth inhibitory activity, and that expression of cyclin D1, a known target of the canonical Wnt signaling pathway, correlated negatively with Fat1$_{IC}$ expression. Together these findings suggested that growth inhibition by Fat1 might involve β-catenin. In our immunofluorescent analyses of RASMCs (FIG. 6), Fat1 localized to both cell-cell junctions and cellular free edges, while β-catenin was concentrated at sites of cell-cell contact. By two color immunofluorescence analysis, we found areas along cell-cell junctions where the two signals overlapped (FIG. 6A). This overlap did not include the cellular free edges, where Fat1 alone was seen (FIG. 6B).

Junctional β-catenin and Fat1 have been identified in epithelial cells that display apical-basal polarity, but it is thought that the two proteins occupy distinct domains, with β-catenin at apical adherens junctions and Fat1 at basolateral points of cell-cell contact (Tanoue and Takeichi, 2004; Tanoue and Takeichi, 2005). VSMCs are non-polarized (Muller and Gimbrone, 1986), so this model of apical-basal domain specialization may not apply. To test directly if Fat1 and O-catenin can interact at physiologic levels of expression in VSMCs, endogenous Fat1 was immunoprecipitated. Recovery of O-catenin was also determined. Both this assay and reciprocal co-immunoprecipitations of β-catenin followed by immunoblotting for Fat1 demonstrated interaction of the two proteins (FIG. 6C). This finding suggests that the non-polarized nature of VSMCs allows for protein-protein interactions not found in polarized cell types such as epithelial cells. Further immunoblotting of Fat1 immunoprecipitates with a pan-cadherin antibody did not reveal associated (classical) cadherins that might associate with both Fat1 and β-catenin (data not shown).

To characterize the Fat1-β-catenin interaction further, co-immunoprecipitation assays were used in co-transfected 293T cells to map the sequences required for interaction. A series of constructs bearing deletions within the Fat1$_{IC}$ portion of the IL2R-Fat1$_{IC}$-3XFLAG were generated (FIG. 7A). IL2R-E-cadherin$_{IC}$-3XFLAG and IL2R-3XFLAG (containing no Fat1 sequences) constructs served as positive and negative controls, respectively. The expression of Myc-tagged β-catenin and FLAG-tagged fusion proteins was confirmed, as was immunoprecipitation of transfected Myc-tagged β-catenin (FIG. 7B, lower panels). Interaction of β-catenin with the IL2R-Fat1$_{IC}$-3XFLAG derivatives was assessed by immunoblotting with FLAG antibody (FIG. 7B, upper panel). A robust FLAG signal was obtained with the IL2R-Fat1$_{IC}$-3XFLAG construct containing the complete Fat1$_{IC}$ domain and with derivatives 1, III, and V. Weaker signals were seen with constructs II and IV, which lack the FC1 and both FC1 and FC2 domains, respectively. While these findings based on overexpressed proteins must be interpreted with caution, they suggest that β-catenin interacts with the Fat1$_{IC}$ principally through the FC1 domain, but leave open the possibility that the FC2 domain or additional sequences also contribute to the interaction. Interestingly, the E-cadherin-based positive control yielded a comparatively strong band, despite input of substantially less protein.

Expression of the Fat1$_{IC}$ Affects β-Catenin Cellular Distribution and Transcriptional Activity.

Figure 8:
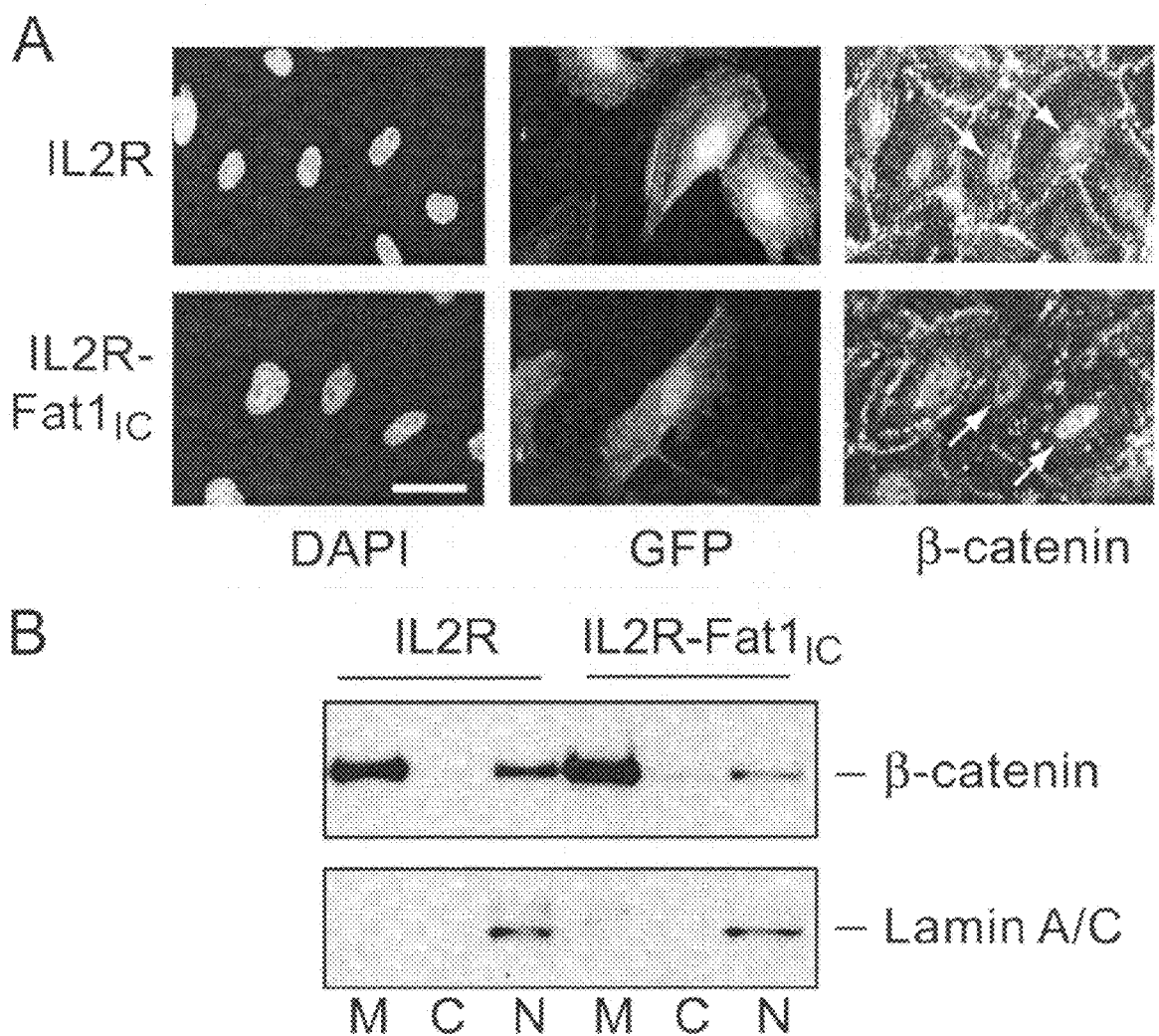
FIG. 8 is fluorescence micrographs and photographs of western blots showing the effect of Fat1$_{IC}$ overexpression on β-catenin nuclear localization in VSMCs. Panel A shows immunofluorescence analysis of β-catenin subcellular localization in IL2R-GFP-RV (upper) and IL2R-Fat1$_{IC}$-GFP-RV (lower) transduced RASMCs. Cells were treated with LiCl (20 mmol/L) for 6 h, and then stained with anti-β-catenin antibody and DAPI. Transduced cells were identified by co-expressed GFP. Arrows indicate nuclear β-catenin signal of untransduced and transduced cells within each panel (see text). Scale bar, 10 μm. Panel B shows western analysis of β-catenin in membrane (M), cytoplasmic (C), and nuclear (N) fractions extracted from IL2R-GFP-RV and IL2R-Fat1$_{IC}$-GFP-RV transduced A7r5 cells treated with LiCl, as above. The blot was probed for lamin A/C to assess fractionation and loading.

As noted above, changes in Fat1 or Fat1$_{IC}$ expression affected expression of a O-catenin target gene, cyclin D1, but had little effect on overall β-catenin levels (FIG. 4B). Having found evidence for co-localization and interaction of β-catenin and Fat1 in VSMCs, it was postulated that Fat1 might be acting like a classical cadherin to affect the subcellular localization and activity of β-catenin. This was first examined using immunocytochemistry. Expression plasmids encoding IL2R or IL2R-Fat1$_{IC}$ were introduced into VSMCs, which were subsequently treated with LiCl (20 mM) for 6 h to activate Wnt signaling and promote nuclear translocation of β-catenin (Hedgepeth et al., 1997). The intensity of nuclear β-catenin staining did not appear to be affected by expression of IL2R (arrows, FIG. 8A, upper panel). In contrast, nuclear accumulation of β-catenin appeared decreased in the IL2R-Fat1$_{IC}$-expressing cells (arrows, FIG. 8A, lower panel), as compared with untransfected cells. To assess this effect in a more quantitative way, the distribution of β-catenin was determined in the membrane, cytoplasmic, and nuclear fractions of IL2R-GFP-RV and IL2R-Fat1$_{IC}$-GFP-RV transduced VSMC cultures treated with LiCl. As shown in FIG. 8B, immunoblotting showed a relative decrease in nuclear β-catenin accumulation in cells expressing IL2R-Fat1$_{IC}$, as compared with those expressing IL2R (respective nuclear β-catenin/lamin A/C ratios 0.8 (IL2R-Fat1$_{IC}$) vs 1.65 (IL2R)).

To assess further the functional significance of the Fat1-β-catenin interaction in VSMCs, we tested the effect of Fat1$_{IC}$ overexpression on β-catenin-mediated transcription. A7r5 cells were co-transfected with β-catenin and/or IL2R-Fat1$_{IC}$, along with the TCF-luciferase reporter construct Topflash or its negative control, Fopflash (FIG. 9A). Topflash reporter activity reflects activation of the canonical Wnt signaling pathway, β-catenin nuclear translocation, and formation of TCF/β-catenin heterodimers; Fopflash contains mutated TCF binding sites and serves as a control for non-specific activation (Korinek et al., 1997). A full-length N-cadherin cDNA and the IL2R-E-cadherin$_{IC}$ construct were also tested as controls. Specific activation of Topflash by β-catenin was ~10-fold above basal levels, and the three test constructs all inhibited this activation significantly. Interestingly, the inhibition due to both IL2R-Fat1$_{IC}$ (40%) and N-cadherin (55%) was less complete than that resulting from co-transfection of IL2R-E-cadherin$_{IC}$, which abolished all β-catenin-mediated transactivation. We also evaluated the effect of decreased Fat1 expression. Immunocytochemistry of LiCl-stimulated MASMCs suggested a relative enhancement of nuclear O-catenin staining in Fat1-depleted cells (FIG. 9B). To assess this observation more quantitatively, we transfected MASMCs first with control or Fat1-specific siRNA and then with the Topflash reporter. As shown in FIG. 9C, LiCl-stimulated TCF/β-catenin transcriptional activation was ~30% higher in Fat1 knockdown cells compared with control.

Figure 5:
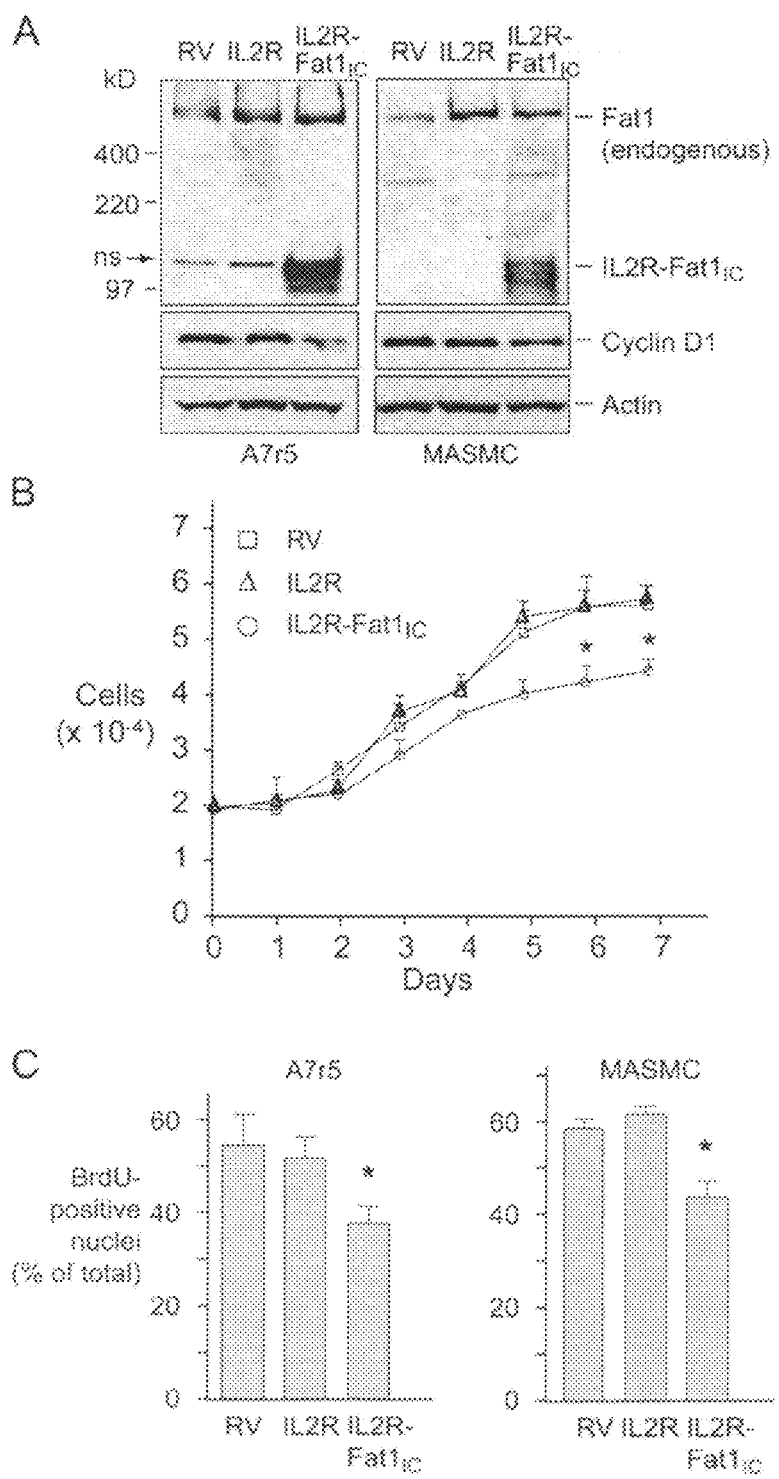
FIG. 5 is photographs of western blots and graphs showing the effect of IL2R-Fat1$_{IC}$ expression on VSMC growth. RV, IL2R, and IL2R-Fat1$_{IC}$ designate A7r5 or MASMCs transduced with the corresponding retroviral constructs. Panel A shows a western analyses of IL2R-Fat1$_{IC}$ expression in A7r5 and MASMC stable transfectants. A non-specific band (ns) near the IL2R-Fat1$_{IC}$ protein is indicated. The blots were also probed for cyclin D1 and actin. Panel B shows the effect of IL2R-Fat1$_{IC}$ on A7r5 cell growth. Cell number was calculated by CyQuant fluorescence assay by reference to a standard curve. Panel C shows the effect of IL2R-Fat1$_{IC}$ on DNA synthesis in A7r5 and MASMCs, evaluated by BrdU incorporation. *, $P<0.05$ vs. control.
Figure 6:
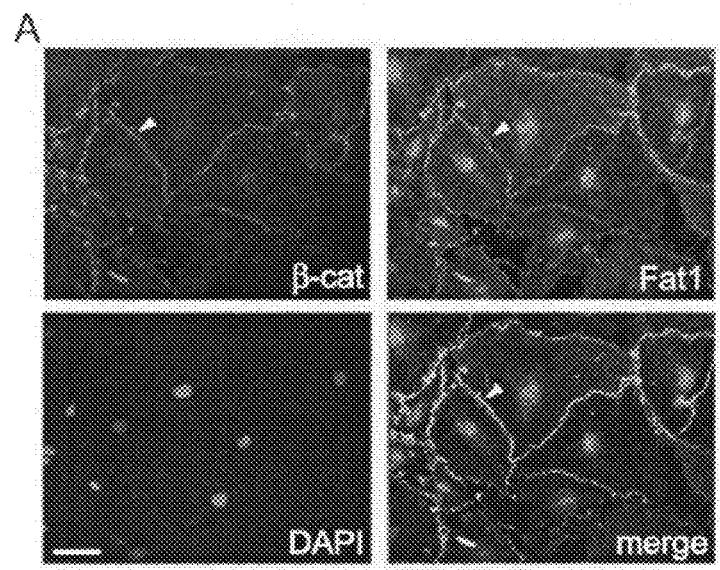
FIG. 6 is fluorescence micrographs and photographs of western blots showing the co-localization and interaction of endogenous β-catenin and Fat1 in VSMCs. Panel A shows an immunofluorescence analysis of β-catenin (β-cat), Fat1, and areas of co-localization ("merge"). Nuclei were stained with DAPI as indicated. β-catenin and Fat1 co-localization at cell-cell junctions is indicated by an arrowhead. Scale bar (10 μm) applies to all panels. Panel B shows detail from the panels in A, showing staining for Fat1 (right micrograph), but not β-catenin (left), at the cellular free edge. Scale bar, 10 μm. Panel C shows the co-immunoprecipitation of endogenous β-catenin and Fat1. Cell lysates were incubated with antibodies specific for Fat1 (upper panels) or β-catenin (lower panels) or normal rabbit or mouse IgG, and the immunoprecipitated complexes were analyzed by western blot for Fat1 and β-catenin, as indicated.
Figure 6:
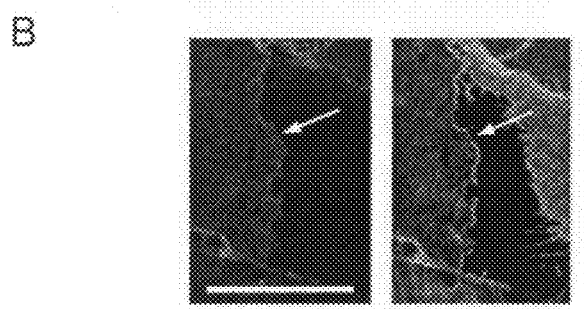
Figure 6:
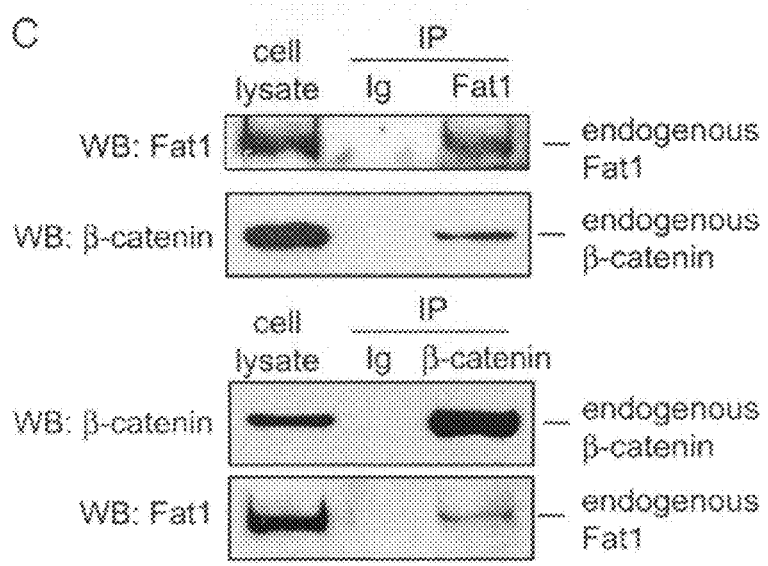

As shown in FIGS. 4 and 5, cyclin D1 levels varied inversely with the level of Fat1$_{IC}$ expression. The cyclin D1 promoter is a known transcriptional target of Wnt signaling and activated TCF/β-catenin complexes (Shutman et al., 1999; Tetsu and McCormick, 1999), so we postulated that Fat1$_{IC}$ might also inhibit the native cyclin D1 promoter. VSMCs were co-transfected with β-catenin and/or IL2R-Fat1$_{IC}$, along with the cyclin D1 promoter-luciferase reporter construct (Herber et al., 1994). N-cadherin and the IL2R-E-cadherin$_{IC}$ fusion protein were also tested. Most of the β-catenin-mediated activation of the cyclin D1 promoter reporter was eliminated by IL2R-Fat1$_{IC}$ or N-cadherin expression (FIG. 9D). Consistent with the Topflash results, IL2R-E-cadherin$_{IC}$ was more effective, as it decreased promoter activity to a level below baseline.

Inhibition of β-Catenin Activity Depends on Extranuclear Localization of the Fat1$_{IC}$.

Figure 10:
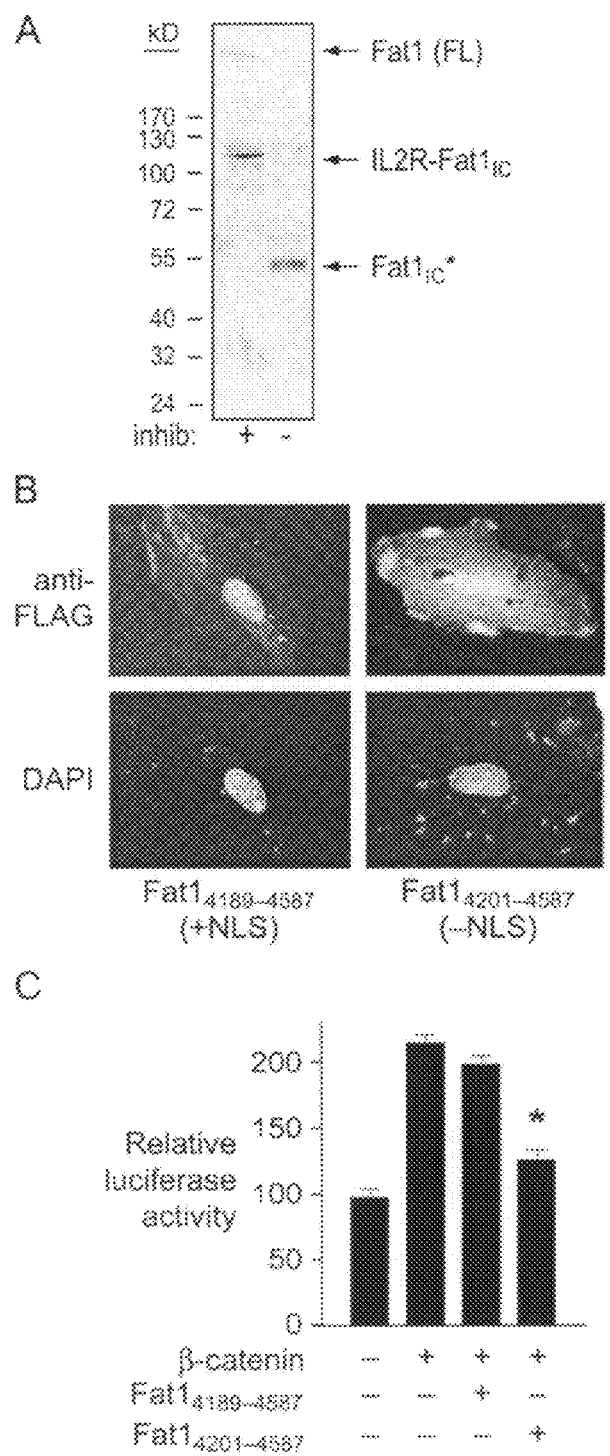
FIG. 10 is a photograph of a western blot, fluorescent micrographs, and a graph showing cleavage, localization, and activity of Fat1 cytoplasmic sequences in VSMC protein extracts. Panel A shows western analysis of A7r5 extracts transduced with IL2R-Fat1$_{IC}$ retrovirus. Total cellular protein was incubated at 37° C. for 15 min with or without proteinase inhibitors (inhib). Both full length (FL) Fat1 and the fusion protein (IL2R-Fat1$_{IC}$), are apparent with proteinase inhibition; only a single band (Fat1$_{IC}$*) of ~50 kD is seen without inhibition. Panel B shows subcellular localization of the FLAG-tagged Fat1 cytoplasmic domain with (Fat1$_{4189-4587}$) or without (Fat1$_{4201-4587}$) the putative NLS in transfected A7r5 cells. Anti-FLAG immunofluorescence and DAPI nuclear stains are shown. Panel C shows the effect of the NLS on Fat1$_{IC}$-mediated inhibition of β-catenin activation of the cyclin D1 promoter. Luciferase activity was assessed 24 h after transfection of A7r5 cells with the indicated expression constructs and the cyclin D1 promoter reporter. *, P<0.01 vs. activity with β-catenin alone.

Fat1 is a type I transmembrane protein, and immunofluorescence studies with antiserum specific for Fat1$_{IC}$ sequences showed expression at the cell surface, as expected (FIG. 6). We also noted consistent signals in the cell nucleus with this antiserum. This observation, together with a recent report of localization of Fat1 cytoplasmic sequences to the nucleus (Magg et al., 2005), raised the possibility that inhibition of β-catenin by Fat1 might result from a nuclear (transcriptional repressor) function of a cleaved Fat1$_{IC}$ fragment, rather than sequestration of O-catenin outside the nucleus. Indeed, incubation without proteinase inhibitors of extracts of A7r5 cells expressing both native Fat1 and the IL2R-Fat1$_{IC}$ fusion protein showed the disappearance of these full length proteins and rapid appearance of a single, relatively stable species of ~50 kD (FIG. 10A). Because the N-terminus of this cleaved product is not yet defined, we designate it as Fat1$_{IC}$*; its apparent size in SDS-PAGE suggests that it contains most, if not all, of the ~400 aa Fat1$_{IC}$ domain.

Like human Fat1$_{IC}$ (Magg et al., 2005), the mouse Fat1$_{IC}$ contains a potential nuclear localizing sequence (NLS) (RK-MISRKKKR) near its N-terminus. The effect of this sequence on Fat1$_{IC}$ localization was tested by immunocytochemical analysis of A7r5 cells transfected with FLAG-tagged expression constructs that retain (Fat1$_{4189-4587}$) or exclude (Fat1$_{4201-4587}$) the NLS motif. Fat1$_{4189-4587}$ localized almost exclusively to the nucleus, while Fat1$_{4201-4587}$ was apparent in the nucleus and prominent throughout the cytoplasm (FIG. 10B).

To evaluate these findings in the context of Fat1-mediated VSMC growth inhibition, these Fat1$_{IC}$ derivatives were tested for effects on cyclin D1 promoter activity. The IL2R-Fat1$_{IC}$ fusion protein yielded significant inhibition of β-catenin-mediated cyclin D1 promoter activation (FIG. 9D, above); Fat1$_{4201-4587}$, but not Fat1$_{4189-4587}$, retained this inhibitory effect (FIG. 10C). Both Fat1$_{4201-4587}$ and Fat1$_{4189-4587}$ are present in the nucleus, but the former has a cytoplasmic distribution not shared by Fat1$_{4189-4587}$; hence, we attribute this inhibitory effect on β-catenin to the extranuclear presence of Fat1$_{4201-4587}$.

Discussion

Fat1 is expressed widely during mouse and rat development (Cox et al., 2000; Ponassi et al., 1999), notably in areas with high levels of cellular proliferation. Although in situ hybridization of rat embryos demonstrated expression of fat1 mRNA in the developing aortic outflow tract (Ponassi et al., 1999), the significance of Fat1 in vascular tissues has not been explored previously.

Figure 2:
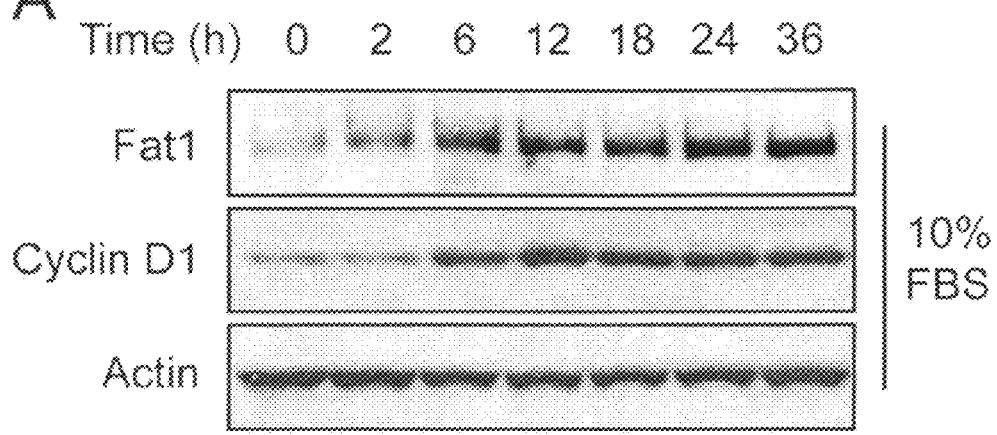
FIG. 2 shows photographs of western blots showing a western analysis of Fat1 expression in RASMCs. Cells were serum-deprived, stimulated as described, and harvested for protein extraction at the indicated time points. Actin expression is shown as a loading reference. Data are representative of three independent experiments. Panel A shows induction by 10% FBS for 0-36 h prior to protein extraction. The blot was also probed for cyclin D1. Panel B shows induction by specific factors. Cells were stimulated with ATII, $10^{-6}$ mol/L, bFGF, 20 ng/mL, or PDGF-BB, 20 ng/mL.
Figure 2:
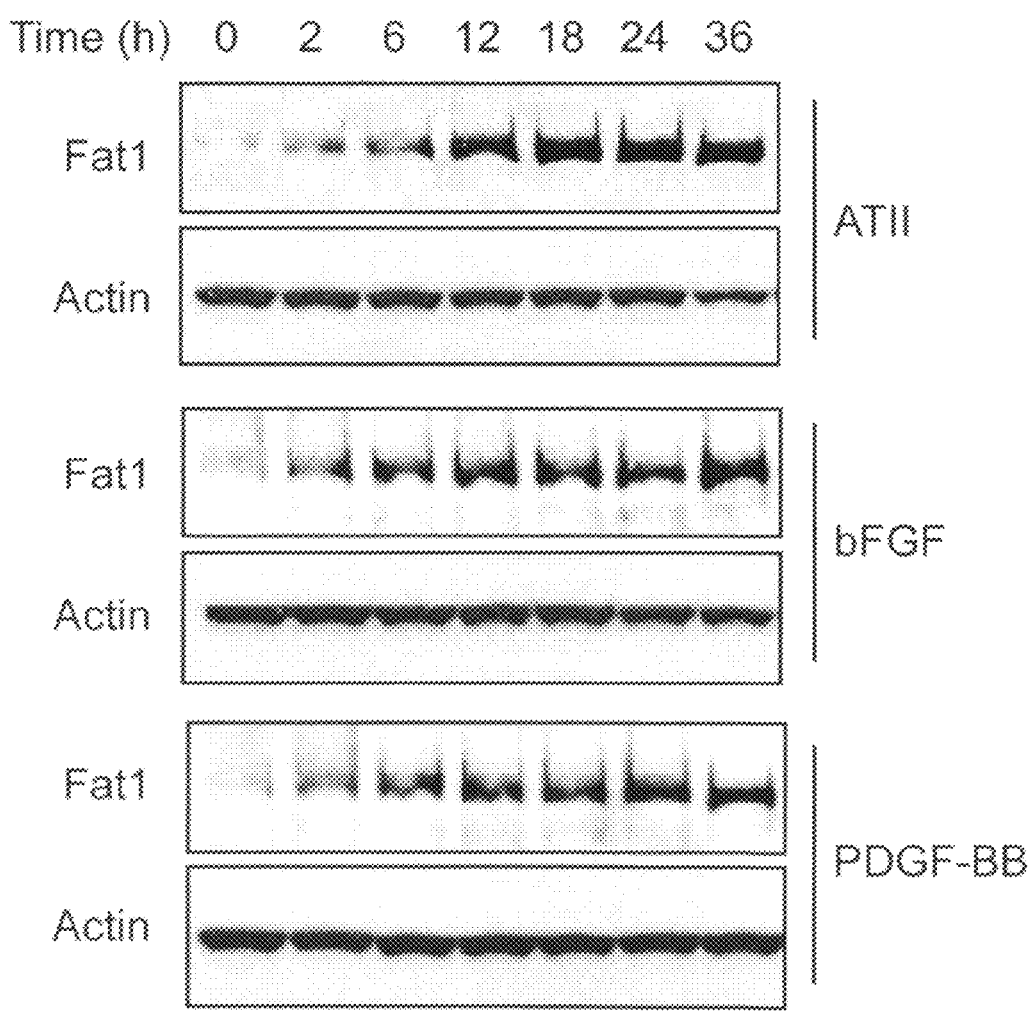

We found relatively low expression of Fat1 in normal adult rat carotid arteries, and substantially increased levels during the first few days after injury (FIG. 1A). Immunohistochemical analyses (FIG. 1C) showed prominent Fat1 staining first in the injured arterial media, and subsequently in the neointima, a pattern of expression similar to that of VSMC proliferation in this model (Clowes et al., 1983b). Interestingly, areas of attenuated neointimal formation showed prominent Fat1 and decreased PCNA staining, providing an initial suggestion that Fat1 might act to limit VSMC proliferation in vivo (FIG. 1C). Nevertheless, Fat1 levels in cultured VSMCs increased in response to serum and several factors known to promote VSMC activation and neointimal formation, including ATII (Powell et al., 1990), PDGF-BB (Ferns et al., 1991), and bFGF (Lindner and Reidy, 1991) (FIG. 2). This expression pattern contrasts with that described for N-cadherin, which decreases after stimulation of VSMC with serum or PDGF- BB (Uglow et al., 2003), and that of R-cadherin, which decreases substantially in the first few days after injury (Slater et al., 2004).

To evaluate how induction of this very large protocadherin might affect the response to vascular injury, we tested the effect of Fat1 on VSMC migration and proliferation, two of the key cellular functions activated in this setting. Both loss of Fat1 expression and expression of the IL2R-Fat1$_{IC}$ fusion protein attenuated VSMC migration (FIG. 3). In the context of recent reports regarding Fat1 function in epithelial cells (Moeller et al., 2004; Tanoue and Takeichi, 2004), these findings suggest that increased Fat1 expression facilitates VSMC migration by providing directional cues and stimulating actin cytoskeletal remodeling through its interactions with proteins of the Ena/VASP family. Together with the Fat1 knockdown results, inhibition of migration by the IL2R-Fat1$_{IC}$ fusion protein suggests that dissociation of Fat1 extracellular interactions from Fat1$_{IC}$-mediated intracellular signaling interferes with directional migration.

Despite the induction of Fat1 in the proliferative phase after injury and in response to growth factor stimulation of cultured cells, our results in both loss- and gain-of-function studies (FIGS. 4, 5) suggest that Fat1 opposes VSMC proliferation. Loss of growth suppression resulting in imaginal disc overgrowth in Drosophila led to identification of Fat (Mahoney et al., 1991), the founding member of the cadherin subfamily that includes mammalian Fat1. While recent analyses indicates that mammalian Fat1 is more closely related to Drosophila Ftl (Castillejo-Lopez et al., 2004) than to Fat, a growth regulatory function has yet to be described for Ftl. Altered growth characteristics were also not identified in mouse Fat1−/− neural progenitors and embryonic skin (Ciani et al., 2003). Thus, our findings in VSMCs may reflect cell type-specific differences in the expression of cadherins or other protocadherins functionally redundant with Fat1, or differences in the level of β-catenin expression. In either case, the results of Fat1 knockdown studies indicate that in VSMCs, endogenous levels of Fat1 expression are sufficient to limit cyclin D1 expression (FIG. 4) and β-catenin-mediated transcription (FIG. 9), while our gain-of-function studies (FIG. 5) suggest that decreased cyclin D1 expression and cell growth are likely physiologic consequences of Fat1 induction. Cyclin D1, a known TCF/β-catenin target gene (Shtutman et al., 1999; Tetsu and McCormick, 1999), plays a critical role in regulation of G1 phase progression and G1/S cell cycle transition (Jiang et al., 1993; Resnitzky et al., 1994), and the level of its expression is closely controlled. Increased Fat1 expression in response to injury probably acts to slow VSMC proliferation, at least in part by decreasing cyclin D1 expression.

Signaling by classical cadherins has been studied extensively, but the mechanisms of protocadherin signaling are not well understood. The intracellular portion of Fat1 shows limited similarity to classical cadherin cytoplasmic domains, with 30 of 137 (22%) residues matching consensus in the FC1 domain and 28 of 84 (33%) residues matching consensus in the FC2 domain (Dunne et al., 1995). Although Tanoue and Takeichi described partial co-localization of Fat1 and β-catenin in immortalized epithelial cell lines, they found more O-catenin in apical lateral cell contacts and more Fat1 in basal lateral cell contacts (Tanoue and Takeichi, 2004), and concluded that Fat1 does not participate in the classical cadherin system (Tanoue and Takeichi, 2005). Interestingly, these findings are consistent with the observation that in polarized epithelial cells, complexes forming between adjacent cells vary in composition according to their apical vs. basal position (Johnston and Gallant, 2002). Thus our findings in VSMCs, which are morphologically and biochemically non-polarized (Muller and Gimbrone, 1986), may differ because of the lack of apical-basal specialization in this cell type. In immunocytochemical studies, we found that β-catenin and Fat1 co-localized in a junctional pattern at points of contact between VSMCs (FIG. 5); Fat1 staining was also observed at cellular free edges, while O-catenin was not.

Figure 7:
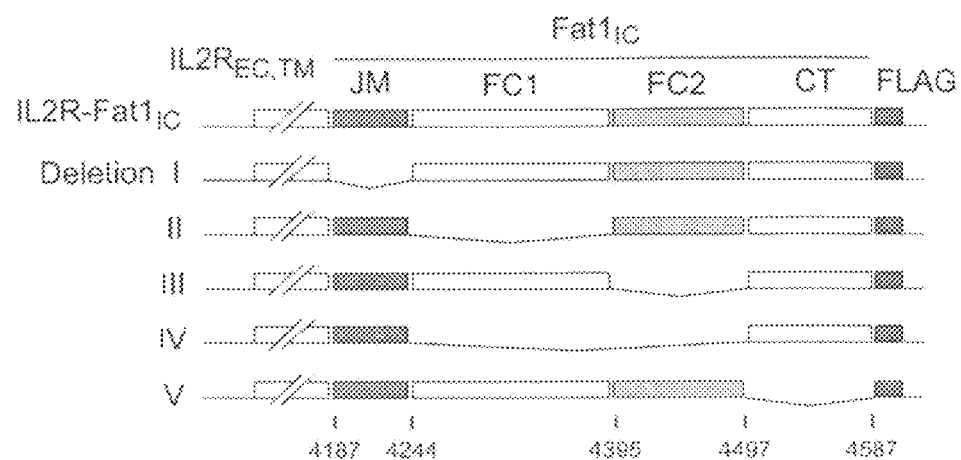
FIG. 7 is a diagram and photographs of western blots showing the identification of β-catenin-interacting residues in the Fat1$_{IC}$ domain by co-immunoprecipitation of epitope-tagged proteins. Panel A is a schematic depiction of FLAG-tagged IL2R-Fat1$_{IC}$ deletion constructs. Fat1$_{IC}$ domains indicated: juxtamembrane (JM), FC1, FC2, carboxy-terminus (CT). Panel B shows a western analysis of immunoprecipitated protein complexes. The indicated constructs were transfected into 293T cells. Upper blots: after 24 h, total cellular protein (400 μg) was harvested and analysed by immunoprecipitation and western blotting (WB) with antibodies against the epitope tags, as indicated. Lower blots: protein input (7.5%). An analogous E-cadherin-derived construct (IL2R-E-cad$_{IC}$-FLAG) was used as a positive control.
Figure 7:
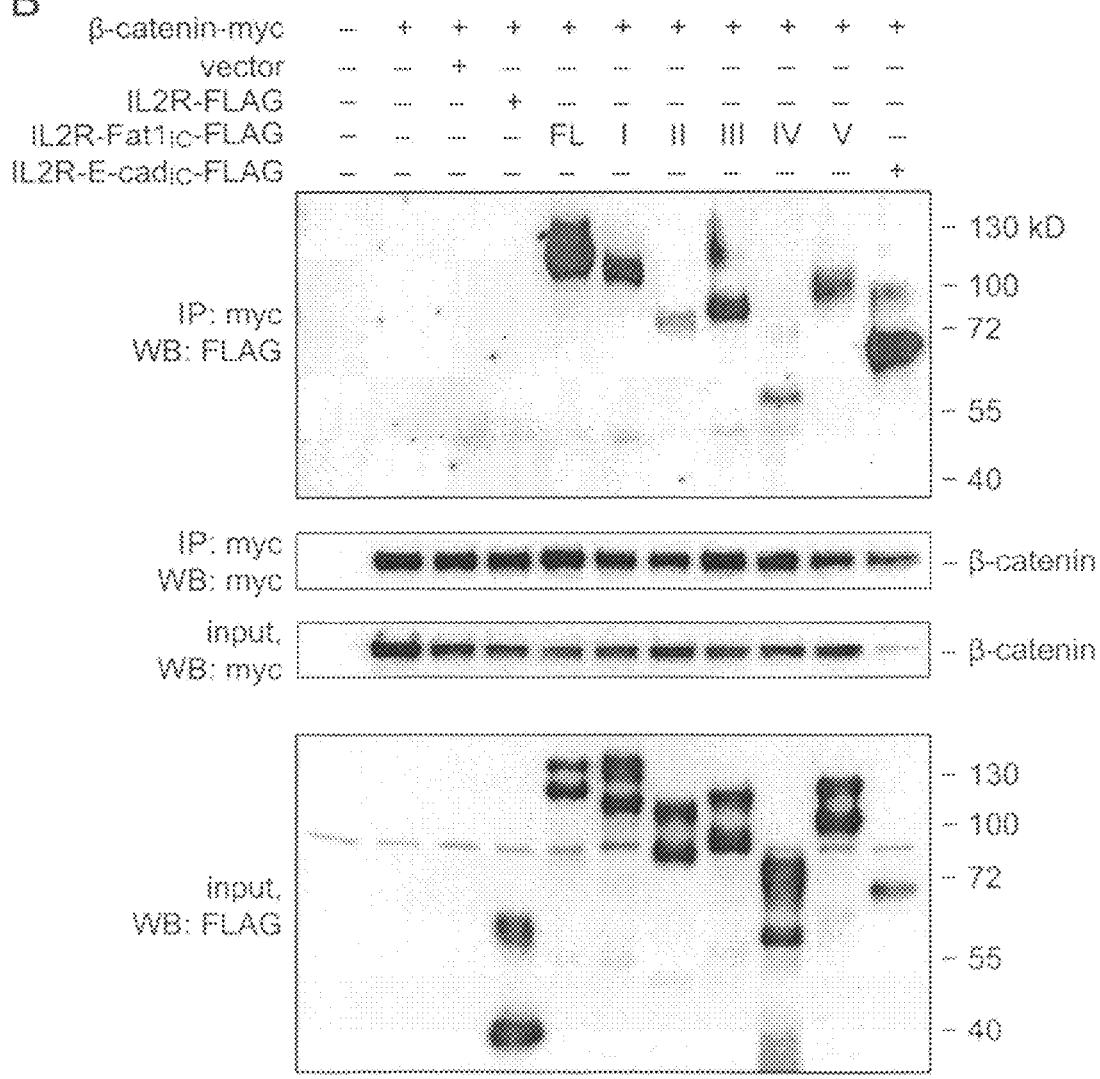

It is believed that a physical interaction between endogenous Fat1 and O-catenin has not been demonstrated previously. Clear evidence was found that these proteins interact at physiologic levels of expression. Transfection studies with the IL2R-Fat1$_{IC}$ fusion protein indicated that, despite limited similarity to the β-catenin-interacting domains of classical cadherins, the Fat1$_{IC}$ domain was sufficient for this interaction (FIG. 7). While mapping studies suggested that the Fat1 FC1 domain was most important for the β-catenin-Fat1 interaction, deletion of other domains within the Fat1$_{IC}$ also decreased the amount of protein co-immunoprecipitation, indicating that sequences both within and outside of the relatively conserved FC1 and FC2 domains may contribute to β-catenin-Fat1 interaction. Interestingly, the FC1 domain corresponds to the area of greatest similarity (54/196 aa identity, (27%)) with the Drosophila Ftl cytoplasmic domain; its role in the O-catenin-Fat1 interaction described here suggests that Ftl may be capable of interaction with armadillo, the Drosophila homologue of β-catenin.

Figure 9:
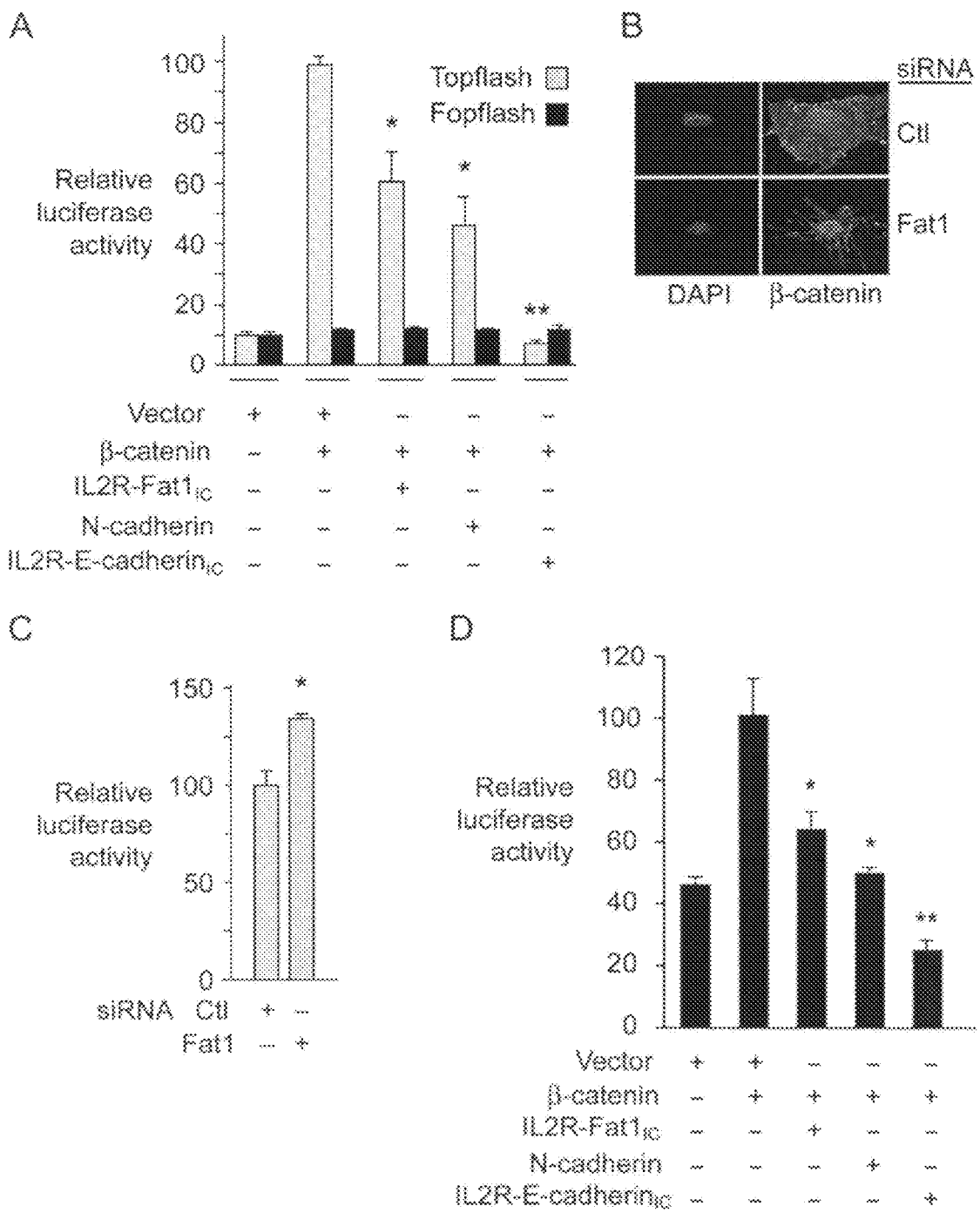
FIG. 9 is graphs and fluorescent micrographs showing the effect of altered Fat1 expression on β-catenin transcriptional activity in VSMCs. Panel A shows Topflash (TCF-luciferase reporter) activation. Topflash or Fopflash control was transfected into A7r5 cells along with expression constructs for β-catenin, IL2R-Fat1$_{IC}$, N-cadherin, and/or IL2R-E-cadherin$_{IC}$. The maximal reporter activity was set to 100. *, P<0.05, **, P<0.01, vs. activity with β-catenin alone. Panel B shows β-catenin localization in MASMCs transfected with control (Ctl, scrambled) or Fat1-specific (7296) siRNAs and stimulated with LiCl (20 mM) for 12 h. Panel C shows Topflash activity with decreased Fat1 expression. MASMCs transfected with the indicated siRNAs and the Topflash reporter were stimulated with LiCl (20 mM) for 12 h prior to assay for luciferase activity. *, P<0.05, vs. activity with Ctl siRNA. Panel D shows Cyclin D1 promoter activation. The cyclin D1 promoter-luciferase construct was transfected into A7r5 cells along with test constructs, as in A. *, P<0.05, **, P<0.01, vs. activity with β-catenin alone.

The IL2R-Fat1$_{IC}$ chimera allowed functional analyses without confounding effects attributable to increased expression of the Fat1 extracellular domain. Expression of IL2R-Fat1$_{IC}$, but not a control protein lacking the Fat1$_{IC}$ domain, decreased nuclear translocation of O-catenin (FIG. 8), and inhibited β-catenin transactivation of both synthetic (Topflash) and native (cyclin D1) TCF-dependent promoters (FIG. 9). Although we found evidence of Fat1 cleavage resulting in a Fat1$_{IC}$* fragment that may localize to the nucleus (FIG. 10), only a defined Fat1$_{IC}$ fragment lacking the NLS (aa 4189-4198) reproduced the inhibitory effect of the IL2R-Fat1$_{IC}$ fusion protein. This result suggests that inhibition of β-catenin transcriptional activity is mediated by Fat1$_{IC}$ outside the nucleus, and is not due to Fat1$_{IC}$ peptides in the nucleus. Thus, it remains to be determined if cleavage and nuclear translocation of Fat1$_{IC}$ underlies a specific function, perhaps as a chaperone or transcriptional regulator, or if it is important as a means to inactivate Fat1-mediated inhibition of β-catenin. Our studies to date indicate that the interaction of Fat1 cytoplasmic sequences with β-catenin has consequences for overall regulation of VSMC growth. The underlying mechanism appears similar to that described for classical cadherin-mediated sequestration of β-catenin in epithelial cells (Orsulic et al., 1999), but in the case of the protocadherin Fat1, this mechanism may be operative only in non-polarized cells such as VSMCs.

These findings suggest that increased expression of Fat1 after vascular injury facilitates migration and opposes proliferation of VSMCs. The former effect likely involves Fat1 interaction with Ena/VASP proteins, as described in other cell types (Moeller et al., 2004; Tanoue and Takeichi, 2004), while the latter effect relies on decreased nuclear accumulation of β-catenin (this study). Interestingly, Fat1$_{IC}$ interaction with, and inhibition of O-catenin both appeared less robust than that observed with classical cadherin sequences (FIGS. 7, 9), suggesting that Fat1 may be less efficient than the classical cadherins at sequestering β-catenin. Fat1 induction after injury and by growth factors contrasts with the expression pattern of other cadherins found in VSMCs. Together, these observations suggest that Fat1 may guide VSMC migration while remaining relatively permissive of growth in settings when VSMC proliferation is necessary for vascular repair.

Drosophila Ftl is thought to use its exceptionally large extracellular domain to promote epithelial cell separation during formation of tubular organs in embryogenesis (Castillejo-Lopez et al., 2004); it may be that mammalian Fat1, by virtue of its similar structure, may expedite circumferential distribution of VSMCs around the injured artery. Altogether, it is tempting to speculate that Fat1 limits VSMC proliferation while providing directional migration cues important during vascular remodeling, providing an integrative function that may oppose the formation of hyperproliferative cellular clusters. Finally, though expression of Fat1 in human vascular disease has not yet been evaluated, it is possible that loss of Fat1-mediated negative regulation could contribute to VSMC hyperplastic syndromes such as restenosis, transplant arteriopathy, or vein graft disease.

Materials and Methods

Rat Carotid Artery Balloon Injury.

All procedures were in accordance with institutional guidelines. The rat carotid artery balloon injury model was implemented as described (Sibinga et al., 1997). Briefly, male Sprague-Dawley rats (20 in total, Zivic-Miller) weighing 350 to 400 g were anesthetized with ketamine (40 mg/kg) and xylazine (5 mg/kg). The left common carotid artery was denuded of endothelium and stretched by three passages of a 2F embolectomy catheter according to standard protocols. At 3, 7 and 14 days after injury, animals were reanesthetized and killed, and carotid arteries were harvested and snap-frozen in liquid nitrogen for RNA and protein extraction, or fixed with 4% PFA and processed for paraffin embedding for immunohistochemical analysis.

qPCR.

A cDNA fragment identified in differential mRNA display analysis of the rat carotid artery injury model (Sibinga et al., 1997) was cloned, sequenced, and subjected to BLAST analysis, which revealed homology of the sequence fragment with the 3' end of the rat Fat1 ORF (Genbank NM_031819). Total RNA was extracted from vascular tissues by homogenization in TRIzol (Invitrogen), treated with DNase 1 (1 U/μl, Promega), and used for first-strand cDNA synthesis. The mRNA levels were quantified in triplicate by qPCR in the Mx3000P Real-Time PCR System with the Brilliant SYBR Green qPCR kit (Stratagene). Rat Fat1 specific primers for qPCR were 5'-CCCCTTCCAACTCTCCCTCA-3' (forward) (SEQ ID NO:3) and 5'-CAGGCTCTCCCGGGCACTGT-3' (reverse) (SEQ ID NO:4). PCR cycling conditions included 10 min at 95° C. for 1 cycle followed by 45 cycles at 95° C. for 30 s, 60° C. for 30 s, and 72° C. for 60 s. Dissociation curve analysis confirmed that signals corresponded to unique amplicons. Expression levels were normalized by glyceraldehyde-3-phosphate dehydrogenase (GAPDH) in RNA levels for each sample, obtained from parallel assays and analyzed using the comparative $\Delta\Delta C_t$ method (Bustin, 2000).

Western Analysis.

Fat1-specific antisera were raised in rabbits. A cDNA fragment encoding mouse Fat1 aa 4434-4587 was generated by PCR and cloned in frame with GST in the pGEX-2T plasmid. The resultant fusion protein was expressed in bacteria, purified by GST-sepharose affinity chromatography (Pharmacia), and used as an immunogen in a standard rabbit injection protocol (Cocalico Labs). Fat1-specific antiserum was purified by affinity chromatography performed sequentially on a GST column and a GST-Fat1 column. Antiserum specificity was evaluated by Western analysis of GST-Fat1 fusion protein and whole cell lysates from RASMCs (1:5000 dilution). Other mouse antibodies used were anti-β-catenin (1:100, E-5, Santa Cruz), anti-cyclin D1 (1:100, DCS-6, NeoMarkers), anti-FLAG M2 (1:5000, Sigma), and anti-c-myc (1:250, 9E10).

For protein analyses, cells or vascular tissue samples were homogenized and extracted in RIPA buffer with or without protease inhibitors. Whole cell lysate (30 μg) was separated by electrophoresis through 3-8% Novex Tris-acetate or 4-12% Bis-Tris polyacrylamide gels (Invitrogen) and transferred to Immobilon-P membrane (Millipore). After blocking in TBST (Tris pH 8.0, NaCl 150 mmol/L, and 0.1% Tween-20) plus 4% (w/v) non-fat milk, blots were incubated overnight at 4° C. with primary antibodies. The blots were then incubated with HRP-conjugated secondary antibody and activity was visualized by enhanced chemiluminescence (ECL, Amersham). Equivalent protein loading was evaluated with anti-α-tubulin (1:500, NeoMarkers), anti-lamin A/C (1:100, N-18, Santa Cruz) or anti-actin (1:100, C-11, Santa Cruz) antibodies.

Immunohistochemistry.

Rat carotid arterial sections (5 μm) were incubated overnight with anti-Fat1 antiserum (1:2000), washed extensively, and incubated with a 1:500 dilution of secondary antibody (biotinylated goat anti-rabbit IgG, DAKO). Slides were incubated with avidin and biotinylated HRP, developed with a peroxidase substrate solution (DAKO), and counterstained with hematoxylin (Fisher). Specificity of staining was confirmed by omission of the primary antibody. PCNA staining was performed with anti-PCNA (1:100, PC 10, LabVision), alkaline phosphatase-conjugated goat anti-mouse secondary antibody (1:200), and visualization with BM Purple substrate (Roche). Images were obtained using an Eclipse E600 microscope, 40×/NA 0.75 Plan objective, and Coolpix 5400 camera (Nikon).

Cell Culture.

Primary culture RASMCs were prepared as described (Sibing a et al., 1997) and maintained in Dulbecco's MEM (DMEM, Invitrogen) containing 10% FBS (HyClone), 100 U/mL penicillin, 100 μg/mL streptomycin, and 10 mmol/L HEPES (pH 7.4, Sigma). RASMCs were passaged every 3 to 5 days, and used between 4 and 8 passages from harvest. Primary culture MASMCs were harvested from the aortas of 12 week old male FVB mice by enzymatic dissociation, evaluated by immunocytochemical analysis by using α smooth muscle actin antibody (1:400, Clone 1A4, NeoMarkers) and maintained in DMEM containing 10% FBS, 100 U/mL penicillin, and 100 μg/mL streptomycin. MASMCs were passaged every 2 to 4 days, and used between 4 and 8 passages from harvest. The A7r5 embryonic RASMC, 3T3, and 293T cell lines (American Tissue Type Collection) were cultured in DMEM containing 10% FBS. ATII was obtained from Sigma, and bFGF and PDGF-BB from Collaborative Biomedical. In stimulation experiments, the cells were made quiescent by incubation in medium containing 0.4% horse serum for 72 h prior to addition of the FBS or growth factor. Control cultures received an equivalent amount of vehicle. Whole cellular protein was extracted at designed time points.

RNA Interference.

The mouse Fat1 short interfering RNA (siRNA) templates were comprised of 19 bp sense sequences derived from GenBank Accession AJ250768 (position 4881, 5'-GGACCGAAGTCACCAAGTA-3' [SEQ ID NO:5]; position 5126, 5'-GCGACGCATTTAACATTAA-3' [SEQ ID NO:6]; position 6432, 5'-GCATGACACTTTAAATAAA-3' [SEQ ID NO:7]; position 7296; 5'-GTCTGGCAATGATCATAAA-3') [SEQ ID NO:8] followed by a 9 bp loop sequence, a 19 bp antisense sequence, and a T7 promoter sequence. Control siRNAs included scrambled (GTAACCATAAACAG-GCATT—SEQ ID NO:9) and mismatched (GTCTGATAATGCGCATAAA—SEQ ID NO:10) derivatives of the 7296 sequence, and an unrelated siRNA based on the Renilla luciferase sequence. siRNA was transcribed in vitro using the T7-MEGAshortscript™ kit (Ambion), and transfected with X-tremeGENE Reagent (Roche) according to manufacturer recommendations. Fat1 knockdown efficiency was assessed by Western analysis.

cDNA Constructs.

The mouse Fat1$_{IC}$ cDNA was generated by RT-PCR with primers containing HindIII and XbaI sites (underlined) to facilitate cloning: forward 5'-AAGCTTCTCTGCCGGAAGATGATCAGTCGG-3' (SEQ ID NO:11) and reverse 5'-TCTAGACACTTCCGTATGCTGCTGGGA-3' (SEQ ID NO:12). The product was subcloned into the p3XFLAG-CMV-14 expression vector (Sigma). The IL2R expression construct (LaFlamme et al., 1994) was used to construct a chimeric cDNA encoding the IL2R extracellular and transmembrane domains and the Fat1$_{IC}$, with or without an in frame 3XFLAG tag (IL2R-Fat1$_{IC}$-3XFLAG and IL2R-Fat1$_{IC}$, respectively). The IL2R-E-cadherin$_{IC}$-3XFLAG construct was produced using a similar strategy. The truncated FLAG-tagged Fat1$_{IC}$ constructs, Fat1$_{4189-4587}$ and Fat1$_{4201-4587}$, were generated by PCR from the IL2R-Fat1$_{IC}$-3XFLAG template using forward primers 5'-CCATGGGC-CTCTGCCGGAAGATGATCAGT-3' (SEQ ID NO:13) and 5'-CCATGGGCCAGGCTGAACCTGAAGACAAAC-3' (SEQ ID NO:14) and the CMV24 reverse primer; the resulting fragments were cloned into pcDNA3.1v5 (Invitrogen). The FLAG-tagged N-cadherin and Myc-tagged β-catenin constructs were gifts from R. Hazan and R. Kemler, respectively. All constructs were confirmed by sequencing.

Retrovirus Preparation and Transduction.

The retrovirus system used is based on the IRES-GFP-RV constructs developed by K. Murphy (Washington University, St. Louis) and Phoenix ecotropic packing cells provided by G. Nolan (Stanford University). The IL2R-Fat1$_{IC}$ cDNA was inserted upstream of the encephalomyocarditis virus internal ribosomal entry sequence (IRES) and green fluorescent protein (GFP) ORF in the GFP-RV vector. A7r5 cells, MASMCs, or RASMCs ($5 \times 10^5$) were infected with virus-containing supernatant in the presence of polybrene (8 µg/mL). Control cells transduced with virus encoding GFP alone or IL2R and GFP were generated in parallel, and FACS analysis of retroviral transduced cell lines indicated similar levels of GFP expression.

Cell Migration Assays.

Cell migration was assessed by 1) scratch wounding of monolayers and 2) with Transwell 24-well cell culture inserts with 8-µm pores (Costar). For the former, MASMCs transfected with control or Fat1-specific siRNA were grown to confluence, and monolayers were denuded similarly using a 1000 µl pipette tip. Photomicrographs of the same fields were obtained sequentially at 24 and 30 h after injury using a Nikon TMS microscope, Plan 4×/NA 0.13 DL objective, and Coolpix 5400 camera, and cellular progress was quantitated by planimetry of the denuded area and converted to distance migrated using NIH Image 1.63 software. For Transwell assays, quiescent cells were harvested, counted, and added ($5 \times 10^4$/well) to the insert. Culture medium containing 10% FBS as chemotactic agent was added to the lower chamber. After 4 h, non-migrating cells were removed from upper filter surfaces, and the filter was washed, fixed, and stained. Six randomly selected 200× fields were then photographed and cells that had migrated to the underside of the filter were counted.

Cell Proliferation Assays.

Cell number was evaluated with the CyQUANT Assay (Molecular Probes). Cells ($2 \times 10^4$ per well) were plated in 6-well plates in DMEM containing 2% FBS, medium was replaced every other day, and at each time point, triplicate wells were washed with PBS and frozen at −80° C. Net sample fluorescence was determined on a Victor 2 plate reader (Wallac) and enumerated by reference to a standard curve. For the bromodeoxyuridine (BrdU) incorporation assay, cells plated on chamber slides (Becton-Dickinson) were serum-starved (0.4% horse serum) for 48 h and then stimulated with 10% FBS. BrdU (10 µM, Sigma) was added to cells for 6 h prior to harvest at 24 h. Cells were washed in PBS, fixed in 4% PFA, treated with HCl, and stained sequentially with anti-BrdU antibody (1:200, Abcam) and Alexa Fluor 555 conjugated secondary antibody (1:2000, Molecular Probes). Cells were counterstained with DAPI (Molecular Probes). Signals were visualized by fluorescence microscopy, and the numbers of BrdU-positive and total nuclei per field calculated.

Immunocytochemistry.

Cells were plated on chamber slides 24 h prior to staining, and then washed with PBS, fixed with PFA, blocked with 3% normal goat serum, and incubated with anti-β-catenin (1:100) and anti-Fat1 (1:1000) antibodies. Specific staining was identified with goat anti-mouse and chicken anti-rabbit IgG (Alexa Fluors, Molecular Probes). Expression of FLAG-tagged proteins was detected using FITC-conjugated anti-FLAG M2 antibody (8 µg/ml, Sigma). After counterstaining with DAPI, samples were mounted (Supermount medium, Biogenex) on glass slides and signals were visualized using an Olympus IX70 inverted fluorescent microscope equipped with 20×/NA 0.4 and 40×/NA 0.6 LWD objectives and standard fluorescent filter sets, a Cooke Sensicam CCD camera, and IPLab software (Scanalytics). Subsequent image processing was performed using Photoshop 7.0 and Illustrator 10.0 (Adobe Systems). Routine control experiments included omission of the primary antibodies. For Wnt pathway activation, cells were treated with LiCl (20 mmol/L) for 6-12 h, and then stained with anti-β-catenin antibody and DAPI nuclear stain.

Co-Immunoprecipitation.

Deletions within the Fat1$_{IC}$ portion of the IL2R-Fat1$_{IC}$-3XFLAG construct were engineered using the vector XbaI site and introducing NheI restriction sites (Quikchange mutagenesis, Stratagene) in frame at the following positions in the mouse Fat1 aa sequence: 4187, 4244, 4395, and 4497. The sequences between selected pairs of restriction sites were excised, plasmids recircularized, and constructs confirmed by sequencing. Plasmids were introduced into 293T cells using Lipofectamine 2000 (Invitrogen). Whole cell lysates were harvested 24 Ii after transfection in lysis buffer containing 50 mM Tris (pH7.4), 150 mM NaCl, 1 mM EDTA, 0.5% Nonidet P-40, 0.1% sodium deoxycholate, 1 mM $Na_3VO_4$, 1 mM NaF, with protease inhibitors. Myc-tagged β-catenin was immunoprecipitated by incubating 400 µg of precleared lysate with 2 µg of c-Myc antibody for 2 h at 4° C., followed by incubation with protein G agarose (Invitrogen) at 4° C. overnight. For immunoprecipitation of endogenous proteins, RASMC whole cell lysates were precleared and then incubated with anti-Fat1 antiserum, anti-β-catenin antibody, or normal rabbit or mouse IgG for 2 h at 4° C., followed by incubation with protein G agarose overnight. The beads were washed and immune complexes recovered by boiling in sample buffer.

Fat1 and β-catenin were detected by Western analysis, as described above.

Cell Fractionation.

Membrane, cytoplasmic, and nuclear fractions were prepared using the Compartment Protein Extraction Kit (Chemicon) according to the manufacturer's instructions. Fractionation and loading of proteins was evaluated by western analysis with anti-lamin A/C antibody (Santa Cruz).

Analysis of Reporter Gene Activation.

A7r5 cells growing in DMEM supplemented with 10% FBS were transfected transiently using Lipofectamine 2000 with β-catenin, IL2R-Fat1$_{IC}$, Fat1$_{4189-4587}$, Fat1$_{4201-4587}$ or control expression constructs, along with the TCF wild type (Topflash) and mutated control (Fopflash) luciferase reporter plasmids (Upstate Biotechnology), or cyclin D1 promoter luciferase reporter (Herber et al., 1994). MASMCs were transfected by Amaxa electroporation according to the manufacturer's instructions. The total amount of transfected DNA was kept constant. Cell lysates were harvested 24 h after transfection, and luciferase activity was determined using the Glo-lysis buffer system (Promega) and the Victor 2 plate reader. Luciferase activities were normalized to protein levels for each well. The data shown represent transfections repeated at least three times each.

Statistical Analysis.

Experiments were repeated at least three times. Data are presented as mean±SEM. Comparisons between 2 groups were analyzed by Student's t test, and comparisons between 3 or more groups were assessed by analysis of variance (ANOVA) with a Bonferroni/Dunn post hoc test. Significance was accepted for values of $P<0.05$.

Abbreviations List:

IC, intracellular; MASMC, mouse aortic smooth muscle cell; qPCR, quantitative PCR; RASMC, rat aortic smooth muscle cell; siRNA, small interfering RNA; VSMC, vascular smooth muscle cell.

SEQ ID NOs

```
SEQ ID NO: 1. Mouse Fat1 amino acid sequence - deduced from Refseq
Genbank accession NM_001081286 (see also Genbank NP_001074755.1)
   1 mqrhltllll lllflqqfgd sdgsqrlept ppiqfthfqy nvtvhensaa ktyvqhprkm
  61 giyildpswe irykivsgds enlfkaeeyv lgdfcflrir tkggntailn revrdhytli
 121 vkavekatda earakvrvqv ldtndlrplf sptsysvslp entairtsia rvsatdadig
 181 tngefyysfk drtdvfaihp tsgvvvltgr ldfletqlye leilaadrgm klygssgvss
 241 lakltvhveq anecapiita vtlspseldk dptyaiitve dcdqgangei aslsivagdl
 301 lqqfktvrsf pgskafkvka vgavdwdshp ygynltlqak dkqtppqfsp vkvvhiispq
 361 fragpvkfem dvyraeisef apphtpvvlv kaipsyshlr yvfksapgkp kfglnhntgl
 421 isilepirrq htshfelevt tsdkrasarv vvkvlgtnsn ppeftqtsyk asidenapig
 481 aavtrvsamd pdegengyvt ysianlnhvp fvidhftgtv stsenldyel mprvytlrir
 541 asdwglpyrr evevlatitl nnlndntplf erincegtip rdlgvgeqit tvsaidadel
 601 qlvryqieag neldlfglnp ssgvlslkhs ltdglgakvs fhslritatd genfatplyi
 661 nltvaasrkp vnlqceetgv akmlaekllq ankihsqgdv ediffdsysv nthtpqfgvt
 721 lptgievken lpvganilfm natdldsgfn gklvyaisgg nddscftidm etgvlkvlsp
 781 ldrevmdkyt lnitvydlgi pqraawrlld vtvldandna peflqesyfv evsedkevns
 841 eiiqveatdk dlgpsghvty ailtdtekfs idsmtgvvki iqpldrevqp vhylkieard
 901 qateeprlfs tvllkvsldd vndnpprfip pnysvkvred lpegtiimwl eaydpdvgqs
 961 sqvryslldh geghfdvdkl sgavrivqql dfekkqlynl tvrakdkgkp vslsstcyve
1021 vevvdvnenl htpvfssfve kgvvkedvpt gssvmtvsah dedtgrdgei rysirdgsgi
1081 gvfrideetg vietsdrldr estshywltv yatdqgvvpl ssfievyiev edvndnapqt
1141 sepvyypeim enspkdvsvv qieafdpdss sndkltyrit sgnpqgffsi hpktglittt
1201 srkldreqqd ehilevtvtd ngvpprstia rvivkilden dnrpqflqkf ykirlperek
1261 adgdrsaskr eplyrviaad kdegpnaels ysieeqnehg rfsiepktgv vsskkfsaag
1321 eydilsikav dngrpqksst trlhiewisk pkpssepisf eesvfsftvm esdpvahmig
1381 visveppgmp lwfdiiggny dshfdvdkgt gtiivakpld aeqkssynlt veatdgttti
1441 ltqvlikvid tndhrpqfst skyevavped tepeveliqi savdrdeknk liytlqssid
1501 paslkkfrld patgalytae kldheaihqh vltvmvrdqd vpvkrnfari vvnvsdkndh
1561 apwftspsyd grvyesaavg svvlqvtald kdkgrnaevl ysiesgnign sftidpilgs
```

```
1621  iktareldrs  hqvdydlmvk  atdkgdppms  emtsvriavt  vadnaspkft  skeysaeise
1681  airigsfvgm  vsahsqssvm  yeirdgnmgd  afninphsgs  iitqraldfe  tlpmysltvq
1741  gtnmaglstn  ttvvvhvrde  ndnppvftqa  eysgfisesa  svnsvvltdr  nvplviratd
1801  adresnallv  yqivepsvhn  yfaidpttga  irtvlsldye  ethafhftvq  vhdmgtprlf
1861  aeyaanvtvh  vidindcppv  fskslyevsl  llptyrgvnv  itvnatdads  kafsqvmysi
1921  tegnigekfs  mdhktgtiai  qnttqlrsry  eltvrasdgr  ftsmasvkin  vkesresplk
1981  ftqdaysavv  kensteartl  avitaignpl  neplfyriln  pdrrfkisht  sgvlsttgip
2041  fdreqqetfd  vvvevtkehe  psavahvvvk  vtvedqndna  pvfvnlpyya  vvkvdaevgh
2101  viryvtaidr  dsgrngdihy  ylkehhdhfq  igpsgdislk  kqfehdtlnk  eylvtvvakd
2161  ggspafsaev  lvpitvmnka  mpvfekafys  aeipeniqmh  spvvhiqans  peglkvfysi
2221  tdgdpfsqft  infntgvvnv  iapldfeshp  ayklsvratd  sltgahaevf  vdiivedind
2281  nppvfvqpsy  sttlseasvi  gtpvlqvrat  dsdsepnrgi  syqlignhsk  shdhfhidsn
2341  tglislvral  dyeqsqqhri  fvravdggmp  alssdvvvtv  avtdlndnpp  lfeqqvyear
2401  isehaahghf  vmcvracdad  ssdldkleys  ilsgndhksf  iidretgiit  lsnlrrhtlk
2461  pfyslnvsvs  dgvfrssarv  nvtvmggnlh  spvfhqneye  velaenaplh  tlvvqvkasd
2521  rdsgiyshvt  yhivndfakd  rfyvndrgqi  ftlekldret  paekvisirl  makdaggkva
2581  fctvnviltd  dndnapqfrs  tkyevnigss  aakgtsvvkv  fasdadegsn  advtyaiead
2641  sesvkenlei  nkltglittk  esliglenef  ftffvravds  gsppresvvp  vyikilppev
2701  qlprfsepfy  tytisedtpi  gteidlirve  hggavlyilv  kgntpesnrd  effvidrqng
2761  rlkleksldh  ettkwyqfsi  larctlddye  vvasidvsiq  vkdandnspv  lesspyeafi
2821  venlpggsrv  iqirasdlds  gangqvmysl  dqsqdadiie  sfainmetgw  ittlkeldhe
2881  erasyqikvv  asdhgekvql  sstaivgvtv  tdvndspprf  taeiykgtvs  eddppggvia
2941  ilsttdadte  einrqvsyfi  tggdalgqfa  venvqsdwrv  yvkkpldreq  kdsylltvta
3001  tdgtfsskar  vevkvldand  nspvcektsy  sdtipedalp  qklvmqvsat  dadirsnaei
3061  tytlfgsgae  kfklnpdtge  lrtlalldre  eqavynllvk  atdgggrscq  aaivltledv
3121  ndnapeftae  pytitvfent  epgtpltrvq  atdadtglnr  kisysivesa  dgqfsiners
3181  giiqlekhld  relqavytlt  lkavdqglpr  rltatgtvvv  svldindnpp  vfeyreygas
3241  vsedivigte  vlqvyaasrd  ieanaeitya  iisgnehgkf  sidsktgaif  iiesldyess
3301  heyyltveat  dggtpslsdv  atvninvtdi  ndnspvfsqd  tyttvvseda  aleqpvitim
3361  addadgpsns  hihysiiegn  qgspftidpv  rgevkvtkpl  dretisgytl  tvqaadngnp
3421  prvntttvni  dvsdvndnap  lfsrdnysvi  iqenkpvgfs  vlklvvtdkd  sshngppfff
3481  tivsgndena  fevnqhgvll  taatikrkvk  dhyllhvkva  dsgkpqlssm  thidirviee
3541  sihppailpl  eififatfgee  ysggvigkih  atdqdvydtl  mysldphmdg  lfsvsstggk
3601  liahrkldig  qyllnvsvtd  gkfttvadit  vhiqqvtqem  lnhtvairfa  nltpeefvgd
3661  ywrnfqralr  nilgvrkndi  qivslqpsep  hshldvllfv  ersggthvst  kqllhkinss
3721  vtdveeiigv  rilevfqklc  agldcpwkfc  dekvsvdenv  msthstarls  fvtprhhrta
3781  vclckdgtcp  pvhhgcednp  cpagsecvad  preekyscvc  pgggfgkcpg  sssitftgns
3841  fvkyrllene  nrlemklsmr  lrtysshavv  myargtdysi  pgivsvqsiq  vndgqwhavs
3901  levegnyakl  vldevhtasg  tapgalktln  ldnyvffggh  lrqqgtkhgr  gaqvasgfrg
3961  cmdsiylngq  elplnnkpra  yahieewvdl  shgclltate  dcssspcqng  gvcnpsptgg
4021  yyckcsalyv  gtfcevsvnp  cssnpclygg  tcmvdnggfv  cqcrglytgl  vlffsfcmcf
```

```
4081  slfrcqlspy ckddpckngg tcfdsldgav cqcdsgfrge rcqsdideca qnpcrngalc
4141  enthgsyhcn csqeyrgkhc edaspnhyvs tpwniglaeg igiivfiagi vllvmvfvlc
4201  rkmisrkkkr qaepedkrlg pttaflqrpy fdsklnkniy sdippqvpvr pisytpsips
4261  dsrnnldrns fegsaipehp efstfnpesm hghrkavavc svapnlpppp psnspsdsds
4321  iqkpswdfdy dakvvdldpc lskkpleekp sqpysaresl sevqslssfq sescddnesl
4381  aapdlskprg yhwdtsdwmp svplpdiqef pnyeaideht plysadpnai dtdyypggyd
4441  iesdfpppppe dfpapdelpp lppefsdqfe sihpprdmpa agslgsssrs rqrfnlnqyl
4501  pnfypadmse pqkqgagens pcrepytpyp pgyqrnfeap tienmmnsvy astascsdvs
4561  accevesevm msdyesgddg hfeevtippl dsqqhtev
```

SEQ ID NO:2. Human Fat1 amino acid sequence - deduced from Refseq
Genbank accession NM_005245.3 (see also Genbank NP_005236.2)

```
   1  mqrhlallll llllfqhfgd sdgsqrleqt plqfthleyn vtvqensaak tyvghpvkmg
  61  vyithpawev rykivsgdse nlfkaeeyil gdfcflrirt kggntailnr evkdhytliv
 121  kaleknthve artkvrvqvl dtndlrplfs ptsysvslpe ntairtsiar vsatdadigt
 181  ngefyysfkd rtdmfaihpt sgvivltgrl dyletklyem eilaadrgmk lygssgissm
 241  akltvhieqa necapvitav tlspseldrd payaivtvdd cdqgangdia slsivagdll
 301  qqfrtvrsfp gskeykvkai ggidwdshpf gynltlqakd kgtppqfssv kvihvtspqf
 361  kagpvkfekd vyraeisefa ppntpvvmvk aipayshlry vfkstpgkak fslnyntgli
 421  silepvkrqq aahfelevtt sdrkastkvl vkvlgansnp peftqtayka afdenvpigt
 481  tvmslsavdp degengyvty sianlnhvpf aidhftgavs tsenldyelm prvytlrira
 541  sdwglpyrre vevlatitln nlndntplfe kincegtipr dlgvgeqitt vsaidadelq
 601  lvqyqieagn eldffslnpn sgvlslkrsl mdglgakvsf hslritatdg enfatplyin
 661  itvaashklv nlgceetgva kmlaekllga nklhnqgeve diffdshsvn ahipqfrstl
 721  ptgiqvkenq pvgssvifmn stdldtgfng klvyavsggn edscfmidme tgmlkilspl
 781  drettdkytl nitvydlgip qkaawrllhv vvvdandnpp eflqesyfve vsedkevhse
 841  iiqveatdkd lgpnghvtys ivtdtdtfsi dsvtgvvnia rpldrelqhe hslkieardq
 901  areepqlfst vvvkvsledv ndnpptfipp nyrvkvredl pegtvimwle ahdpdlgqsg
 961  qvryslldhg egnfdvdkls gavrivqqld fekkqvynlt vrakdkgkpv slsstcyvev
1021  evvdvnenlh ppvfssfvek gtvkedapvg slvmtvsahd edarrdgeir ysirdgsgvg
1081  vfkigeetgv ietsdrldre stshywltvf atdqgvvpls sfieiyieve dvndnapqts
1141  epvyypeime nspkdvsvvq ieafdpdsss ndklmykits qnpqgffsih pktglittts
1201  rkldreqqde hilevtvtdn gsppkstiar vivkildend nkpqflqkfy kirlperekp
1261  drernarrep lyhviatdkd egpnaeisys iedgnehgkf fiepktgvvs skrfsaagey
1321  dilsikavdn grpqkssttr lhiewiskpk pslepisfee sfftftvmes dpvahmigvi
1381  sveppgiplw fditggnyds hfdvdkgtgt iivakpldae qksnynltve atdgtttilt
1441  qvfikvidtn dhrpqfstsk yevvipedta peteilqisa vdqdeknkli ytlqssrdpl
1501  slkkfrldpa tgslytsekl dheavhqhtl tvmvrdqdvp vkrnfarivv nvsdtndhap
1561  wftassykgr vyesaavgsv vlqvtaldkd kgknaevlys iesgnignsf midpvlgsik
1621  takeldrsnq aeydlmvkat dkgsppmsei tsvrifvtia dnaspkftsk eysvelsetv
1681  sigsfvgmvt ahsqssvvye ikdgntgdaf dinphsgtii tqkaldfetl piytliiqgt
1741  nmaglstntt vlvhlqdend napvfmqaey tglisesasi nsvvltdrnv plviraadad
```

```
1801 kdsnallvyh ivepsvhtyf aidsstgaih tvlsldyeet sifhftvqvh dmgtprlfae
1861 yaanvtvhvi dindcppvfa kplyeasll1 ptykgvkvit vnatdadssa fsqliysite
1921 gnigekfsmd yktgaltvqn ttqlrsryel tvrasdgrfa gltsvkinvk eskeshlkft
1981 qdvysavvke nsteaetlav itaignpine plfyhilnpd rrfkisrtsg vlsttgtpfd
2041 reqqeafdvv vevteehkps avahvvvkvi vedqndnapv fvnlpyyavv kvdtevghvi
2101 ryvtavdrds grngevhyyl kehhehfqig plgeislkkq feldtlnkey lvtvvakdgg
2161 npafsaeviv pitvmnkamp vfekpfysae iaesiqvhsp vvhvqanspe glkvfysitd
2221 gdpfsqftin fntgvinvia pldfeahpay klsiratdsl tgahaevfvd iivddindnp
2281 pvfaqqsyav tlseasvigt svvqvratds dsepnrgisy qmfgnhsksh dhfhvdsstg
2341 lisllrtldy eqsrqhtifv ravdggmptl ssdvivtvdv tdlndnpplf eqqiyearis
2401 ehaphqhfvt cvkaydadss didklqysil sgndhkhfvi dsatgiitls nlhrhalkpf
2461 yslnlsvsdg vfrsstqvhv tviggnlhsp aflqneyeve laenaplhtl vmevkttdgd
2521 sgiyghvtyh ivndfakdrf yinergqift lekldretpa ekvisvrlma kdaggkvafc
2581 tvnviltddn dnapqfratk yevnigssaa kgtsvvkvla sdadegsnad ityaieadse
2641 svkenleink lsgvittkes liglenefft ffvravdngs pskesvvlvy vkilppemql
2701 pkfsepfytf tvsedvpigt eidliraehs gtvlyslvkg ntpesnrdes fvidrqsgrl
2761 kleksldhet tkwyqfsila rctqddhemv asvdvsiqvk dandnspvfe sspyeafive
2821 nlpggsrviq irasdadsgt ngqvmysldq sqsveviesf ainmetgwit tlkeldhekr
2881 dnyqikvvas dhgekiqlss taivdvtvtd vndspprfta eiykgtvsed dpqggviail
2941 sttdadseei nrqvtyfitg gdplgqfave tiqnewkvyv kkpldrekrd nylltitatd
3001 gtfsskaive vkvldandns pvcektlysd tipedvlpgk limqisatda dirsnaeity
3061 tllgsgaekf klnpdtgelk tstpldreeq avyhllvrat dgggrfcqas ivltledvnd
3121 napefsadpy aitvfentep qtlltrvqat dadaglnrki lyslidsadg qfsinelsgi
3181 iqlekpldre lqavytlslk avdqglprrl tatgtvivsv ldindnppvf eyreygatvs
3241 edilvgtevl qvyaasrdie anaeitysii sgnehgkfsi dsktgavfii enldyesshe
3301 yyltveatdg gtpslsdvat vnvnvtdind ntpvfsqdty ttvisedavl eqsvitvmad
3361 dadgpsnshi hysiidgnqg ssftidpvrg evkvtklldr etisgytltv qasdngsppr
3421 vntttvnidv sdvndnapvf srgnysviiq enkpvgfsvl qlvvtdedss hngppfffti
3481 vtgndekafe vnpqgvllts saikrkekdh yllqvkvadn gkpqlsslty idirvieesi
3541 yppailplei fitssgeeys ggvigkihat dqdvydtlty sldpqmdnlf svsstggkli
3601 ahkkldigqy llnvsvtdgk fttvaditvh irqvtqemln htiairfanl tpeefvgdyw
3661 rnfqralrni lgvrrndiqi vslqssephp hldvllfvek pgsaqistkq llhkinssvt
3721 dieeiigvri lnvfqklcag ldcpwkfcde kvsvdesvms thstarlsfv tprhhraavc
3781 lckegrcppv hhgceddpcp egsecvsdpw eekhtcvcps grfgqcpgss smtltgnsyv
3841 kyrltenenk lemkltmrlr tysthavvmy argtdysile ihhgrlqykf dcgsgpgivs
3901 vqsiqvndgq whavalevng nyarlvldqv htasgtapgt lktlnldnyv ffgghirqqg
3961 trhgrspqvg ngfrgcmdsi ylngqelpln skprsyahie esvdvspgcf ltatedcasn
4021 pcqnggvcnp spaggyyckc salyigthce isvnpcsskp clyggtcvvd nggfvcqcrg
4081 lytgqrcqls pyckdepckn ggtcfdsldg avcqcdsgfr gercqsdide csgnpclhga
4141 lcenthgsyh cncsheyrgr hcedaapnqy vstpwnigla egigivvfva gifllvvvfv
4201 lcrkmisrkk khqaepkdkh lgpataflqr pyfdsklnkn iysdippqvp vrpisytpsi
```

```
4261  psdsrnnldr  nsfegsaipe  hpefstfnpe  svhghrkava  vcsvapnlpp  pppsnspsds 4321  dsiqkpswdf  dydtkvvdld  pclskkplee  kpsqpysare  slsevqslss  fqsescddng 4381  yhwdtsdwmp  svplpdiqef  pnyevideqt  plysadpnai  dtdyypggyd  iesdfppppe 4441  dfpaadelpp  lppefsnqfe  sihpprdmpa  agslgsssrn  rqrfnlnqyl  pnfypldmse 4501  pqtkgtgens  tcrephapyp  pgyqrhfeap  avesmpmsvy  astascsdvs  accevesevm 4561  msdyesgddg  hfeevtippl  dsqqhtev SEQ ID NO:3. Rat Fat1-specific forward primer
CCCCTTCCAACTCTCCCTCA SEQ ID NO:4. Rat Fat1-specific reverse primer
CAGGCTCTCCCGGGCACTGT SEQ ID NO:5. Mouse Fat1 siRNA template
GGACCGAAGTCACCAAGTA SEQ ID NO:6. Mouse Fat1 siRNA template
GCGACGCATTTAACATTAA SEQ ID NO:7. Mouse Fat1 siRNA template
GCATGACACTTTAAATAAA SEQ ID NO:8. Mouse Fat1 siRNA template
GTCTGGCAATGATCATAAA SEQ ID NO:9. Control siRNA
GTAACCATAAACAGGCATT SEQ ID NO:10. Control siRNA
GTCTGATAATGCGCATAAA SEQ ID NO:11. Mouse Fat1$_{IC}$ RT-PCR forward primer. Restriction site
is underlined.
AAGCTTCTCTGCCGGAAGATGATCAGTCGG SEQ ID NO:12. Mouse Fat1$_{IC}$ RT-PCR reverse primer. Restriction site
is underlined.
TCTAGACACTTCCGTATGCTGCTGGGA SEQ ID NO:13. Fat$_{4189-4587}$ PCR forward primer. Restriction site
is underlined.
CCATGGGCCTCTGCCGGAAGATGATCAGT. Restriction site is underlined.

SEQ ID NO:14. Fat$_{4201-4587}$ PCR forward primer
CCATGGGCCAGGCTGAACCTGAAGACAAAC. Restriction site is underlined.
```

REFERENCES

Angst, B. D., C. Marcozzi, and A. I. Magee. 2001. The cadherin superfamily: diversity in form and function. *J Cell Sci.* 114:629-41.

Bhanot, P., M. Fish, J. A. Jemison, R. Nusse, J. Nathans, and K. M. Cadigan. 1999. Frizzled and Dfrizzled-2 function as redundant receptors for Wingless during *Drosophila* embryonic development. *Development.* 126:4175-86.

Bustin, S. A. 2000. Absolute quantification of mRNA using real-time reverse transcription polymerase chain reaction assays. *J Mol Endocrinol.* 25:169-93.

Castillejo-Lopez, C., W. M. Arias, and S. Baumgartner. 2004. The fat-like gene of *Drosophila* is the true orthologue of vertebrate fat cadherins and is involved in the formation of tubular organs. *J Biol Chem.* 279:24034-43.

Ciani, L., A. Patel, N. D. Allen, and C. ffrench-Constant. 2003. Mice lacking the giant protocadherin mFAT1 exhibit renal slit junction abnormalities and a partially penetrant cyclopia and anophthalmia phenotype. *Mol Cell Biol.* 23:3575-82.

Clowes, A., M. Reidy, and M. Clowes. 1983a. Mechanisms of stenosis after arterial injury. *Lab Invest.* 49:208-215.

Clowes, A. W., M. A. Reidy, and M. M. Clowes. 1983b. Kinetics of cellular proliferation after arterial injury. 1. Smooth muscle growth in the absence of endothelium. *Lab Invest.* 49:327-33.

Cox, B., A. K. Hadjantonakis, J. E. Collins, and A. I. Magee. 2000. Cloning and expression throughout mouse development of mfat1, a homologue of the *Drosophila* tumour suppressor gene fat. *Dev Dyn.* 217:233-40.

Dunne, J., A. M. Hanby, R. Poulsom, T. A. Jones, D. Sheer, W. G. Chin, S. M. Da, Q. Zhao, P. C. Beverley, and M. J. Owen. 1995. Molecular cloning and tissue expression of FAT, the human homologue of the *Drosophila* fat gene that is located on chromosome 4q34-q35 and encodes a putative adhesion molecule. *Genomics.* 30:207-23.

Ferns, G., E. Raines, K. Sprugel, A. Motani, M. Reidy, and R. Ross. 1991. Inhibition of neointimal smooth muscle accumulation after angioplasty by an antibody to PDGF. *Science.* 253:1129-32.

Gallin, W. J. 1998. Evolution of the "classical" cadherin family of cell adhesion molecules in vertebrates. *Mol Biol Evol.* 15:1099-107.

Hedgepeth, C. M., L. J. Conrad, J. Zhang, H. C. Huang, V. M. Lee, and P. S. Klein. 1997. Activation of the Wnt signaling pathway: a molecular mechanism for lithium action. *Dev Biol.* 185:82-91.

Herber, B., M. Truss, M. Beato, and R. Muller. 1994. Inducible regulatory elements in the human cyclin D1 promoter. *Oncogene.* 9:2105-7.

Hou, R., L. Liu, S. Anees, S. Hiroyasu, and Nicholas E. S. Sibing a. 2006. The Fat1 cadherin integrates vascular smooth muscle cell growth and migration signals. *J Cell Biol.* 173:417-29.

Huber, A. H., and W. I. Weis. 2001. The structure of the beta-catenin/E-cadherin complex and the molecular basis of diverse ligand recognition by beta-catenin. *Cell.* 105:391-402.

Jamora, C., R. DasGupta, P. Kocieniewski, and E. Fuchs. 2003. Links between signal transduction, transcription and adhesion in epithelial bud development. *Nature.* 422:317-22.

Jiang, W., S. M. Kahn, P. Zhou, Y. J. Zhang, A. M. Cacace, A. S. Infante, S. Doi, R. M. Santella, and I. B. Weinstein. 1993. Overexpression of cyclin D1 in rat fibroblasts causes abnormalities in growth control, cell cycle progression and gene expression. *Oncogene.* 8:3447-57.

Johnston, L. A., and P. Gallant. 2002. Control of growth and organ size in *Drosophila*. *Bioessays.* 24:54-64.

Jones, M., P. J. Sabatini, F. S. Lee, M. P. Bendeck, and B. L. Langille. 2002. N-cadherin upregulation and function in response of smooth muscle cells to arterial injury. *Arterioscler Thromb Vasc Biol.* 22:1972-7.

Kaplan, D. D., T. E. Meigs, and P. J. Casey. 2001. Distinct regions of the cadherin cytoplasmic domain are essential for functional interaction with Galpha 12 and beta-catenin. *J Biol Chem.* 276:44037-43.

Korinek, V., N. Barker, P. J. Morin, D. van Wichen, R. de Weger, K. W. Kinzler, B. Vogelstein, and H. Clevers. 1997. Constitutive transcriptional activation by a beta-catenin-Tcf complex in APC-/- colon carcinoma. *Science.* 275:1784-7.

LaFlamme, S. E., L. A. Thomas, S. S. Yamada, and K. M. Yamada. 1994. Single subunit chimeric integrins as mimics and inhibitors of endogenous integrin functions in receptor localization, cell spreading and migration, and matrix assembly. *J Cell Biol.* 126:1287-98.

Lindner, V., and M. Reidy. 1991. Proliferation of smooth muscle cells after vascular injury is inhibited by an antibody against basic fibroblast growth factor. *Proc Nat Acad Sci USA* 88:3739-43.

Magg, T., D. Schreiner, G. P. Solis, E. G. Bade, and H. W. Hofer. 2005. Processing of the human protocadherin Fat1 and translocation of its cytoplasmic domain to the nucleus. *Exp Cell Res.* 307:100-8.

Mahoney, P. A., U. Weber, P. Onofrechuk, H. Biessmann, P. J. Bryant, and C. S. Goodman. 1991. The fat tumor suppressor gene in *Drosophila* encodes a novel member of the cadherin gene superfamily. *Cell.* 67:853-68.

Moeller, M. J., A. Soofi, G. S. Braun, X. Li, C. Watzl, W. Kriz, and L. B. Holzman. 2004. Protocadherin FAT1 binds Ena/VASP proteins and is necessary for actin dynamics and cell polarization. *Embo J.* 23:3769-79.

Muller, W. A., and M. A. Gimbrone, Jr. 1986. Plasmalemmal proteins of cultured vascular endothelial cells exhibit apical-basal polarity: analysis by surface-selective iodination. *J Cell Biol.* 103:2389-402.

Nathke, I. S., L. Hinck, J. R. Swedlow, J. Papkoff, and W. J. Nelson. 1994. Defining interactions and distributions of cadherin and catenin complexes in polarized epithelial cells. *J Cell Biol.* 125:1341-52.

Nelson, W. J., and R. Nusse. 2004. Convergence of Wnt, beta-catenin, and cadherin pathways. *Science.* 303:1483-7.

Orsulic, S., O. Huber, H. Aberle, S. Arnold, and R. Kemler. 1999. E-cadherin binding prevents beta-catenin nuclear localization and beta-catenin/LEF-1-mediated transactivation. *J Cell Sci. II* 2 (Pt 8):1237-45.

Owens, G. K., M. S. Kumar, and B. R. Wamhoff. 2004. Molecular regulation of vascular smooth muscle cell differentiation in development and disease. *Physiol Rev.* 84:767-801.

Ponassi, M., T. S. Jacques, L. Ciani, and C. ffrench Constant. 1999. Expression of the rat homologue of the *Drosophila* fat tumour suppressor gene. *Mech Dev.* 80:207-12.

Powell, J., R. Muller, M. Rouge, H. Kuhn, F. Hefti, and H. Baumgartner. 1990. The proliferative response to vascular injury is suppressed by angiotensin-converting enzyme inhibition. *J Cardiovasc Pharm.* 16:S42-9.

Ranganath, S., W. Ouyang, D. Bhattarcharya, W. C. Sha, A. Grupe, G. Peltz, and K. M. Murphy. 1998. GATA-3-dependent enhancer activity in IL-4 gene regulation. *J Immunol.* 161:3822-6.

Resnitzky, D., M. Gossen, H. Bujard, and S. I. Reed. 1994. Acceleration of the G1/S phase transition by expression of cyclins D1 and E with an inducible system. *Mol Cell Biol.* 14:1669-79.

Sadot, E., I. Simcha, M. Shtutman, A. Ben-Ze'ev, and B. Geiger. 1998. Inhibition of beta-catenin-mediated transactivation by cadherin derivatives. *Proc Natl Acad Sci USA.* 95:15339-44.

Shanahan, C. M., and P. L. Weissberg. 1998. Smooth muscle cell heterogeneity: patterns of gene expression in vascular smooth muscle cells in vitro and in vivo. *Arterioscler Thromb Vasc Biol.* 18:333-8.

Shtutman, M., J. Zhurinsky, I. Simcha, C. Albanese, M. D'Amico, R. Pestell, and A. Ben-Ze'ev. 1999. The cyclin D1 gene is a target of the beta-catenin/LEF-1 pathway. *Proc Natl Acad Sci USA.* 96:5522-7.

Sibing a, N. E., L. C. Foster, C. M. Hsieh, M. A. Perrella, W. S. Lee, W. O. Endege, E. H. Sage, M. E. Lee, and E. Haber. 1997. Collagen VIII is expressed by vascular smooth muscle cells in response to vascular injury. *Circ Res.* 80:532-41.

Sincha, I., C. Kirkpatrick, E. Sadot, M. Shtutman, G. Polevoy, B. Geiger, M. Peifer, and A. Ben-Ze'ev. 2001. Cadherin sequences that inhibit beta-catenin signaling: a study in yeast and mammalian cells. *Mol Biol Cell.* 12:1177-88.

Slater, S. C., E. Koutsouki, C. L. Jackson, R. C. Bush, G. D. Angelini, A. C. Newby, and S. J. George. 2004. R-cadherin: beta-catenin complex and its association with vascular smooth muscle cell proliferation. *Arterioscler Thromb Vasc Biol.* 24:1204-10.

Suzuki, S. T. 2000. Recent progress in protocadherin research. *Exp Cell Res.* 261:13-8.

Takeichi, M. 1995. Morphogenetic roles of classic cadherins. *Curr Opin Cell Biol.* 7:619-27.

Tanoue, T., and M. Takeichi. 2004. Mammalian Fat1 cadherin regulates actin dynamics and cell-cell contact. *J Cell Biol.* 165:517-28.

Tanoue, T., and M. Takeichi. 2005. New insights into Fat cadherins. *J Cell Sci.* 118:2347-53.

Tetsu, O., and F. McCormick. 1999. Beta-catenin regulates expression of cyclin D1 in colon carcinoma cells. *Nature.* 398:422-6.

Uglow, E. B., S. Slater, G. B. Sala-Newby, C. M. Aguilera-Garcia, G. D. Angelini, A. C. Newby, and S. J. George.

2003. Dismantling of cadherin-mediated cell-cell contacts modulates smooth muscle cell proliferation. *Circ Res.* 92:1314-21.

Wheelock, M. J., and K. R. Johnson. 2003a. Cadherin-mediated cellular signaling. *Curr Opin Cell Biol.* 15:509-14.

Wheelock, M. J., and K. R. Johnson. 2003b. Cadherins as modulators of cellular phenotype. *Annu Rev Cell Dev Biol.* 19:207-35.

Yagi, T., and M. Takeichi. 2000. Cadherin superfamily genes: functions, genomic organization, and neurologic diversity. *Genes Dev.* 14:1169-80.

Yap, A. S., W. M. Brieher, and B. M. Gumbiner. 1997. Molecular and functional analysis of cadherin-based adherens junctions. *Annu Rev Cell Dev Biol.* 13:119-46

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A method of inhibiting vascular smooth muscle cell (VSMC) proliferation in a patient having a bypass surgery vascular repair or an angioplasty vascular repair, the method comprising administering to the patient having the vascular repair an amount of a fusion protein consisting essentially of the sequence of residues 4202-4588 of SEQ ID NO:2 fused to the amino acid sequence of an extracellular domain and transmembrane region of an interleukin 2 receptor α-chain which localizes to a cell membrane effective to inhibit (VSMC) proliferation.

2. The method of claim 1, wherein the vascular repair is an angioplasty vascular repair.

3. The method of claim 1, wherein the patient is at risk of restenosis.

4. The method of claim 1, wherein the vascular repair is a bypass surgery vascular repair.

5. The method of claim 1, wherein the vascular repair is of a coronary artery.

* * * * *